(12) United States Patent
Agresta

(10) Patent No.: US 10,980,788 B2
(45) Date of Patent: Apr. 20, 2021

(54) THERAPY FOR TREATING MALIGNANCIES

(71) Applicant: Agios Pharmaceuticals, Inc., Cambridge, MA (US)

(72) Inventor: Samuel V. Agresta, Lexington, MA (US)

(73) Assignee: Agios Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 16/434,307

(22) Filed: Jun. 7, 2019

(65) Prior Publication Data

US 2019/0374522 A1 Dec. 12, 2019

Related U.S. Application Data

(60) Provisional application No. 62/682,808, filed on Jun. 8, 2018.

(51) Int. Cl.
*A61K 31/444* (2006.01)
*A61K 9/00* (2006.01)

(52) U.S. Cl.
CPC ......... *A61K 31/444* (2013.01); *A61K 9/0053* (2013.01)

(58) Field of Classification Search
CPC .................................................. A61K 31/444
USPC ........................................................ 514/333
See application file for complete search history.

(56) References Cited

U.S. PATENT DOCUMENTS

| | | | |
|---|---|---|---|
| 2,390,529 A | 12/1945 | Friedheim | |
| 3,755,322 A | 8/1973 | Winter et al. | |
| 3,867,383 A | 2/1975 | Winter | |
| 4,084,053 A | 4/1978 | Desai et al. | |
| 5,021,421 A | 6/1991 | Nino et al. | |
| 5,489,591 A | 2/1996 | Kobayashi et al. | |
| 5,807,876 A | 9/1998 | Armistead et al. | |
| 5,834,485 A | 11/1998 | Dyke et al. | |
| 5,965,559 A | 10/1999 | Faull et al. | |
| 5,965,569 A | 10/1999 | Camps Garcia et al. | |
| 5,984,882 A | 11/1999 | Rosenschein et al. | |
| 6,262,113 B1 | 7/2001 | Widdowson et al. | |
| 6,274,620 B1 | 8/2001 | Labrecque et al. | |
| 6,313,127 B1 | 11/2001 | Waterson et al. | |
| 6,399,358 B1 | 6/2002 | Williams et al. | |
| 6,576,235 B1 | 6/2003 | Williams et al. | |
| 6,723,730 B2 | 4/2004 | Bakthavatchalam et al. | |
| 6,783,965 B1 | 8/2004 | Sherman et al. | |
| 6,979,675 B2 | 12/2005 | Tidmarsh | |
| 7,173,025 B1 | 2/2007 | Stocker et al. | |
| 7,858,782 B2 | 12/2010 | Tao et al. | |
| 8,133,900 B2 | 3/2012 | Hood et al. | |
| 8,257,741 B2 | 9/2012 | Curatolo et al. | |
| 8,263,128 B2 | 9/2012 | Curatolo et al. | |
| 8,337,899 B2 | 12/2012 | Curatolo et al. | |
| 8,367,118 B2 | 2/2013 | Curatolo et al. | |
| 8,431,159 B2 | 4/2013 | Curatolo et al. | |
| 8,465,673 B2 | 6/2013 | Yasuda et al. | |
| 8,957,068 B2 | 2/2015 | Caferro et al. | |
| 9,474,779 B2 * | 10/2016 | Lemieux | A61P 1/04 |
| 9,850,277 B2 * | 12/2017 | Popovici-Muller | A61P 11/00 |
| 9,968,595 B2 * | 5/2018 | Gu | A61K 9/146 |
| 10,111,882 B2 | 10/2018 | Abella et al. | |
| 10,653,710 B2 * | 5/2020 | Agresta | A61P 35/02 |
| 10,717,764 B2 * | 7/2020 | Popovici-Muller | C07D 413/04 |
| 2002/0049310 A1 | 4/2002 | Tateishi et al. | |
| 2002/0188027 A1 | 12/2002 | Robinson et al. | |
| 2003/0095958 A1 | 5/2003 | Bhisetti et al. | |
| 2003/0109527 A1 | 6/2003 | Jin et al. | |
| 2003/0207882 A1 | 11/2003 | Stocker et al. | |
| 2003/0213405 A1 | 11/2003 | Harada et al. | |
| 2004/0067234 A1 | 4/2004 | Einat et al. | |
| 2004/0248221 A1 | 12/2004 | Stockwell | |
| 2005/0261268 A1 | 11/2005 | Arnost et al. | |
| 2006/0084645 A1 | 4/2006 | Pal et al. | |
| 2006/0281122 A1 | 12/2006 | Bryant et al. | |
| 2007/0244088 A1 | 10/2007 | Brickmann et al. | |
| 2008/0132490 A1 | 6/2008 | Bergman et al. | |
| 2008/0300208 A1 | 12/2008 | Einat et al. | |
| 2009/0093526 A1 | 4/2009 | Miller et al. | |
| 2009/0163508 A1 | 6/2009 | Kori et al. | |
| 2009/0163545 A1 | 6/2009 | Goldfarb | |
| 2009/0281089 A1 | 11/2009 | Gunzner et al. | |
| 2009/0286752 A1 | 11/2009 | Etter et al. | |
| 2010/0129350 A1 | 5/2010 | Zacharie et al. | |
| 2010/0144722 A1 | 6/2010 | Alexander et al. | |
| 2010/0273808 A1 | 10/2010 | Armitage et al. | |
| 2010/0331307 A1 | 12/2010 | Salituro et al. | |
| 2011/0073007 A1 | 3/2011 | Yasuda et al. | |
| 2011/0086088 A1 | 4/2011 | Berry | |
| 2011/0288065 A1 | 11/2011 | Fujihara et al. | |

(Continued)

FOREIGN PATENT DOCUMENTS

| | | |
|---|---|---|
| CN | 101296909 A | 10/2008 |
| CN | 101575408 A | 11/2009 |

(Continued)

OTHER PUBLICATIONS

Wolff, Burger's medicinal Chemistry and Drug Discovery, vol. 1, Principles and Practice, John Wiley & sons, New York, 1997.*
West, Solid State Chemistry and its Applications, john Wiley & Sons, 1984.*
DiNardo, N Engl J Med 2018; 378:2386-98.*
Fan, Presentation at the 23rd Congress of the European Hematology Association, Jun. 14-17, 2018, Stockholm, Sweden.*
"Study of orally administered AG-120 in subjects with advanced hematologic malignancies with an IDH1 mutation," clinicaltrials. gov retrieved Feb. 6, 2017.
Aghili et al. "Hydroxyglutaric aciduria and malignant brain tumor: a case report and literature review", Journal of Neuroncology, 2008. 91:233-236.

(Continued)

*Primary Examiner* — Nizal S Chandrakumar
(74) *Attorney, Agent, or Firm* — Goodwin Procter LLP

(57) ABSTRACT

Provided are methods and compositions for treating cancers in patients carrying an IDH1 mutation using an inhibitor of a mutant IDH1 enzyme.

19 Claims, 7 Drawing Sheets

(56) References Cited

U.S. PATENT DOCUMENTS

| | | |
|---|---|---|
| 2012/0121515 A1 | 5/2012 | Dang et al. |
| 2012/0129865 A1 | 5/2012 | Wang et al. |
| 2012/0164143 A1 | 6/2012 | Teeling et al. |
| 2012/0202818 A1 | 8/2012 | Tao et al. |
| 2012/0238576 A1 | 9/2012 | Tao et al. |
| 2012/0277233 A1 | 11/2012 | Tao et al. |
| 2013/0035329 A1 | 2/2013 | Saunders et al. |
| 2013/0109643 A1 | 5/2013 | Riggins et al. |
| 2013/0183281 A1 | 7/2013 | Su et al. |
| 2013/0184222 A1 | 7/2013 | Popovici-Muller et al. |
| 2013/0190249 A1 | 7/2013 | Lemieux et al. |
| 2013/0190287 A1 | 7/2013 | Cianchetta et al. |
| 2013/0197106 A1 | 8/2013 | Fantin et al. |
| 2014/0094503 A1 | 4/2014 | Ma et al. |
| 2014/0187435 A1 | 7/2014 | Dang et al. |
| 2014/0206673 A1 | 7/2014 | Cao et al. |
| 2014/0213580 A1 | 7/2014 | Cao et al. |
| 2015/0018328 A1 | 1/2015 | Konteatis et al. |
| 2015/0031627 A1 | 1/2015 | Lemieux et al. |
| 2015/0031641 A1 | 1/2015 | Levine et al. |
| 2015/0044716 A1 | 2/2015 | Balss et al. |
| 2015/0087600 A1 | 3/2015 | Popovici-Muller et al. |
| 2015/0240286 A1 | 8/2015 | Dang et al. |
| 2015/0299115 A1 | 10/2015 | Popovici-Muller et al. |
| 2016/0130298 A1 | 5/2016 | Lemieux et al. |
| 2016/0264621 A1 | 9/2016 | Popovici-Muller et al. |
| 2016/0304556 A1 | 10/2016 | Popovici-Muller et al. |
| 2017/0007661 A1 | 1/2017 | Gu |
| 2017/0014396 A1 | 1/2017 | Gu |
| 2017/0015703 A1 | 1/2017 | Popovici-Muller et al. |
| 2017/0057994 A1 | 3/2017 | Lemieux et al. |
| 2018/0194802 A1 | 7/2018 | Popovici-Muller et al. |
| 2018/0296583 A1 | 10/2018 | Agresta et al. |
| 2018/0303808 A1 | 10/2018 | Agresta |
| 2018/0303840 A1 | 10/2018 | Chopra et al. |
| 2018/0311249 A1* | 11/2018 | Agresta .............. A61K 31/7048 |
| 2019/0023737 A1 | 1/2019 | Lemieux et al. |
| 2019/0046512 A1 | 2/2019 | Amatangelo et al. |

FOREIGN PATENT DOCUMENTS

| | | |
|---|---|---|
| CN | 102659765 A | 9/2012 |
| CN | 103097340 A | 5/2013 |
| DE | 2263878 A1 | 7/1973 |
| DE | 3314663 A1 | 10/1983 |
| DE | 3512630 A1 | 10/1986 |
| EP | 0022958 A1 | 1/1981 |
| EP | 0384228 A1 | 8/1990 |
| EP | 0385237 A2 | 9/1990 |
| EP | 901786 A2 | 3/1999 |
| EP | 0945446 A1 | 9/1999 |
| EP | 1391487 A2 | 2/2004 |
| EP | 1886673 A2 | 2/2008 |
| FR | 2735127 A1 | 12/1996 |
| GB | 1033266 A | 6/1966 |
| JP | H04099768 A | 3/1992 |
| JP | H05140126 A | 6/1993 |
| JP | H09291034 A | 11/1997 |
| JP | H11158073 A | 6/1999 |
| JP | 2004107220 A | 4/2004 |
| JP | 2005264016 A | 9/2005 |
| JP | 2009237115 A | 10/2009 |
| JP | 2010079130 A | 4/2010 |
| JP | 2010181540 A | 8/2010 |
| JP | 4753336 B2 | 8/2011 |
| JP | 2013519858 A | 5/2013 |
| MX | 2013/000614 A | 6/2013 |
| TW | 201028381 A | 8/2010 |
| WO | 1996030343 A1 | 10/1996 |
| WO | 9728128 A1 | 8/1997 |
| WO | 9728129 A1 | 8/1997 |
| WO | 1997044322 A1 | 11/1997 |
| WO | 9932463 A1 | 7/1999 |
| WO | 00002864 A1 | 1/2000 |
| WO | 2001016097 A1 | 3/2001 |
| WO | 2001019788 A2 | 3/2001 |
| WO | 2001019798 A2 | 3/2001 |
| WO | 0147897 A1 | 7/2001 |
| WO | 2001064642 A2 | 9/2001 |
| WO | 2001064643 A2 | 9/2001 |
| WO | 2002100822 A1 | 12/2002 |
| WO | 2002102313 A2 | 12/2002 |
| WO | 030016289 A1 | 2/2003 |
| WO | 2004009562 A1 | 1/2004 |
| WO | 2004046120 A2 | 6/2004 |
| WO | 2004050033 A2 | 6/2004 |
| WO | 2004073619 A2 | 9/2004 |
| WO | 2004074438 A2 | 9/2004 |
| WO | 2004089470 A2 | 10/2004 |
| WO | 2005035507 A2 | 4/2005 |
| WO | 2005060956 A1 | 7/2005 |
| WO | 2005065691 A1 | 7/2005 |
| WO | 2005103015 A1 | 11/2005 |
| WO | 2005120474 A2 | 12/2005 |
| WO | 2006034341 A2 | 3/2006 |
| WO | 2006038594 A1 | 4/2006 |
| WO | 2006070198 A1 | 7/2006 |
| WO | 2006079791 A1 | 8/2006 |
| WO | 2006/110761 A2 | 10/2006 |
| WO | 2007003934 A2 | 1/2007 |
| WO | 2007023186 A1 | 3/2007 |
| WO | 2008036835 A2 | 3/2008 |
| WO | 2008050168 A1 | 5/2008 |
| WO | 2008050186 A1 | 5/2008 |
| WO | 2008052190 A2 | 5/2008 |
| WO | 2008070661 A1 | 6/2008 |
| WO | 2008073670 A2 | 6/2008 |
| WO | 2008076883 A2 | 6/2008 |
| WO | 2008131547 A1 | 11/2008 |
| WO | 2008154026 A1 | 12/2008 |
| WO | 2009013126 A1 | 1/2009 |
| WO | 2009015254 A1 | 1/2009 |
| WO | 2009016410 A2 | 2/2009 |
| WO | 2009051910 A1 | 4/2009 |
| WO | 2009/126863 A2 | 10/2009 |
| WO | 2009118567 A2 | 10/2009 |
| WO | 2009150248 A1 | 12/2009 |
| WO | 2010007756 A1 | 1/2010 |
| WO | 2010028099 A1 | 3/2010 |
| WO | 2010105243 A1 | 9/2010 |
| WO | 2010129596 A1 | 11/2010 |
| WO | 2010130638 A1 | 11/2010 |
| WO | 2010144338 A1 | 12/2010 |
| WO | 2010144404 A1 | 12/2010 |
| WO | 201105210 A1 | 1/2011 |
| WO | 2011002817 A1 | 1/2011 |
| WO | 2011/027249 A2 | 3/2011 |
| WO | 2011032169 A2 | 3/2011 |
| WO | 2011047432 A1 | 4/2011 |
| WO | 2011050210 A1 | 4/2011 |
| WO | 2011072174 A1 | 6/2011 |
| WO | 2012006506 A1 | 1/2012 |
| WO | 2012009678 A1 | 1/2012 |
| WO | 2012074999 A1 | 6/2012 |
| WO | 2012078288 A2 | 6/2012 |
| WO | 2012092442 A1 | 7/2012 |
| WO | 2012151452 A1 | 11/2012 |
| WO | 2012160034 A1 | 11/2012 |
| WO | 2012171337 A1 | 12/2012 |
| WO | 2012171506 A1 | 12/2012 |
| WO | 2012173682 A2 | 12/2012 |
| WO | 2013004332 A1 | 1/2013 |
| WO | 2013007708 A1 | 1/2013 |
| WO | 2013016206 A1 | 1/2013 |
| WO | 2013102431 A1 | 7/2013 |
| WO | 2013107291 A1 | 7/2013 |
| WO | 2013107405 A1 | 7/2013 |
| WO | 2013133367 A1 | 9/2013 |
| WO | 2014015422 A1 | 1/2014 |
| WO | 2015/003360 A2 | 1/2015 |
| WO | 2015127172 A1 | 8/2015 |
| WO | 2015127173 A1 | 8/2015 |
| WO | 2015138837 A1 | 9/2015 |
| WO | 2015138839 A1 | 9/2015 |

(56) References Cited

FOREIGN PATENT DOCUMENTS

| WO | 2017066566 A1 | 4/2017 |
|---|---|---|
| WO | 2017066571 A1 | 4/2017 |
| WO | 2017096309 A1 | 6/2017 |
| WO | 2017/146795 A1 | 8/2017 |

OTHER PUBLICATIONS

Amary et al. "Ollier disease and Maffucci syndrome are caused by somatic mosiac mutations of IDH1 and IDH2," Nature Genetics Letters, 2011, 43(12):1262-1266.
Ansell et al. "The interactions of artificial coenzymes with alcohol dehydrogenase and other NAD(P)(H) dependent enzymes" Journal of Molecular Catalysis B: Enzymatic (1999) vol. 6, No. 1-2, pp. 111-123.
Astellas, "Dose escalation study investigating the safety, tolerability, pharmacokinetics, pharmacodynamics of ASP2215 in patients with relapsed or refractory acute myeloid leukemia," (Astellas Pharma Global Development, Inc., https://clinicaltrials.gov/ct2/history/NCT02014558?V_11=View#StudyPageTop, Dec. 12, 2013 (v1), obtained from the internet Jun. 21, 2019).
Balss, "Analysis of the IDH1 codon 132 mutation in brain tumors", Acata Neuropathol (2008) vol. 116, pp. 597-602.
Benner et al, "Evolution, language and analogy in functional genomics", Trends in Genetics (2001) vol. 17, pp. 414-418.
Bhushan et al. "Reversed-phase liquid chromatographic resolution of diastereomers of protein and non-protein amino acids prepared with newly synthesized chiral derivatizing reagents based on cyanuric chloride" Amino Acids (2011) vol. 40, pp. 403-409.
Birendra et al. "Evidence for clinical differentiation and differentiation syndrome in patients with acute myeloid eukemia and IDH1 mutations treated with the targeted mutant IDH1 inhibitor, AG-120," Clinical Lymphoma, Myeloma & Leukemia, 2016, 16(8):460-5.
Bleeker et al., "IDH1 mutations at residue p.R132 (IDH1 (R132)) occur frequently in high-grade 18-22 gliomas but not in other solid tumors." Hum Mutal., Jan. 2009, vol. 30, No. 1, pp. 7-11.
Braun et al. "Triazine-based polymers: 4. MALDI-MS of triazine-based polyamines" Polymer (1996) vol. 37, No. 5, pp. 777-783.
Burger et al. "Nuclear substituted 3,4-dihydroxyphenethylamines and related derivatives," Journal of American Chemical Society, 1956, 78(17):4419-4422.
Cairns et al. "Oncogenic Isocitrate Dehydrogenase Mutations: Mechanisms, Models, and Clinical Opportunities" Cancer Discovery (2013) vol. 3, Iss 7, pp. 730-741.
Caunt et al. "MEK1 and MEK2 inhibitors and cancer therapy: the long and winding road," Nature Reviews Cancer, 2015, 15(10):577-592.
Cecil Textbook of Medicine, edited by Bennet, J.C., and Plum F., 20th edition, vol. 1, 1004-1010, 1996.
Chan et al. "Multi-domain hydrogen-bond forming metal chelates: X-ray crystal structuresof dicyclopalladated 2,3-bis[6-(2-amino-4-phenylamino-1 ,3,5-triazinyl)]pyrazine(H2L) [Pd2Br2L] and 2,6-bis[6-(2-amino-4-phenylamino-1,3,5-triazinylium)]-pyridine dichloride" Chemical Communications (1996) No. 1, pp. 81-83.
Chapman et al. "Substituted aminopyrimidine protein kinase B (PknB) inhibitorsshow activity against *Mycobacterium tuberculosis*" Bioorganic & Medicinal Chemistry Letters (2012) vol. 22, pp. 3349-3353.
Chen et al. "Cytotoxicity, Hemolysis, and Acute in Vivo Toxicity of Dendrimers Based on Melamine, Candidate Vehicles for Delivery" J. Am. Chem. Soc. (2004) vol. 126, No. 32, pp. 10044-10048.
Cocco et al. "Synthesis of Triflouromethylated Pyridinecarbonitriles" Journal of Heterocyclic Chemistry, 1995. vol. 32 pp. 543-545.
Dai et al. "Effect of itraconazole, food, and ethnic origin on the pharmacokinetics of ivosidenib in healthy subjects," European Journal of Clinical Pharmacology, 2019 75:1099-1108.
Dang et al., "Cancer-associated IDH1 mutations produce 2-hydroxyglutarate." Nature, 10 29-32 Dec. 2009, vol. 462, No. 7274, pp. 739-744.

Dang et al. "IDH Mutations in Glioma and Acute Myeloid Leukemia" Trends in Molecular Medicine (2010) vol. 16, No. 9, pp. 387-397.
Database CA [Online] Chemical Abstracts Service, Columbus,Ohio, US; Ambartsumyan, E. N. et al: "Synthesis and transformations of chloropyrazolylazines", XP002764692, retrieved from STN Database accession No. 2012:876343 * abstract * & Ambartsumyan, E. N. et al: "Synthesis and transformations of chloropyrazolylazines", Hayastani Kimiakan Handes ( 2011 ), 64(4), 544-550 Coden: KZARF3; ISSN: 1561-4190, 2011.
Database CA [Online] Chemical Abstracts Service. Columbus.Ohio. US; Baibulova M. S. et al:Syntheses from pyridylguanamines_ XP002764691. retrieved from STN Database accession No. 1990:406282 *abstract* & Bai Bulova, M. S. et al: Syntheses from pyridylguanamines, Izvestiya Akademii Nauk Kazakhskoi SSR, Seriya Khimicheskaya, (5), 40-2 Coden: IKAKAK; ISSN: 0002-3205, 1989.
Database CA [Online] Chemical Abstracts Service. Columbus.Ohio. US; Krimmer. Hans Peter et al: "Reaction of .beta.-mercapto .alpha.-amino acids with nitriles".XP002764690.retrieved from STN Database accession No. 1988:529623* abstract* & Krimmer. Hans Peter et al: "Reaction of .beta.-mercapto .alpha.-amino acids with nitriles".Chemiker-Zeitung â€¢ 111(12). 357-61 Coden: CMKZAT; ISSN: 0009-2894.1987.
Davis et al. "Biochemical, Cellular, and Biophysical Characterization of a Potent Inhibitor of Mutant Isocitrate Dehydrogenase IDH1" The Journal of Biological Chemistry (2014) vol. 289, No. 20, pp. 13717-13725.
Dermer et al., "Another Anniversary for the War on Cancer", Bio/Technology, 1994, 12:320.
Dinardo et al. "Characteristics, clinical outcome, and prognostic significance of IDH mutations in AML," American Journal of Hematology, 2015, 90(8):732-736.
Dinardo et al. "Molecular profiling and relationship with clinical response in patients with IDH1 mutation-positive hematologic malignancies receiving AG-120, a first-in-class potent inhibitor of mutant IDH1, in addition to data from the completed dose escalation portion of the phase 1 study," Blood, 2015, 126:1306.
Docoslis et al., "Characterization of the Distribution, Polymorphism, and Stability of Nimodipine in its Solid Dispersions in Polyethylene Glycol by Micro-Raman Spectroscopy and Powder X-Ray Diffraction". The AAPS Journal 2007; 9 (3) Article 43, E361-E370.
Dohner et al. "Acute myeloid leukemia," New England Journal of Medicine, 2015, 373:1136-52.
Dohner et al. "Impact of Genetic Features on Treatment Decisions in AML" American Society of Hematology (2011) pp. 36-42.
Dohner et al. "Impact of genetic features on treatment decisions in AML," ASH Education Program Book, 2011, 1:36-42.
Drew, MGB, et al. "Solvent extraction and lanthanide complexation studies with new terdentate ligands containing two 1, 3, 5-triazine moieties." Dalton Transactions 2 (2004): 244-251.
Duanmu et al. "Dendron-Functionalized Superparamagnetic Nanoparticles with Switchable Solubility in Organic and Aqueous Media: Matriced for Homogeneous Catalysis and Potential MRI Contrast Agents" Chem. Mater. (2006) vol. 18, No. 25, pp. 5973-5981.
Emadi et al. "Presence of isocitrate dehydrogenase mutations may predict clinical response to hypomethylating agents in patients with acute myeloid leukemia," American Journal of Hematology, 2015, 90(5):E77-E79.
Enholm, EJ., Jed M. Hastings, and Chris Edwards. "Hydrogen-Bonded Arrays Coupled by Cross-Metathesis." Synlett Feb. 2008 (2008): 203-206.
Extended European Search Report for PCT/CN2014081957 dated Dec. 9, 2016.
Freshney et al.,Culture of Animal Cells, A Manual of Basic Technique, Alan R. Liss, Inc., 1983, New York, p. 4.
Friesen et al. "Hydroxypropyl Methylcellulose Acetate Succinate-Based Spray-Dried Dispersions: An Overview," Molecular Pharmaceutics, 2008, 5(6):1003-1019.
Genetics Home Reference. "L2HGDH." accessed at <http://ghr.nlm.nih.gov/gene/L2HGDH> on Sep. 4, 2015.

(56) References Cited

OTHER PUBLICATIONS

Gewald et al. "Discovery of triazines as potent, selective and orally active PDE4 inhibitors" Bioorganic & medicinal Chemistry Letters (2013) vol. 23, pp. 4308-4314.
Golub et al., "Molecular Classification of Cancer: Class Discovery and Class Prediction by Gene Expression Monitoring", Science, 286, 531-537, 1999.
Green et al. "The prognostic significance of IDH1 mutations in younger adult patients with acute myeloid leukemia is dependent on FLT3/ITD status," Blood, 2010, 116(15):2779-2782.
Gura. "Systems for identifying new drugs are often faulty," Science, 1997, 278(5340):1041-2.
Hansen et al. "AG-120, an oral, selective, first-in-class, potent inhibitor of mutant IDH1, reduces intracellular 2HG and induces cellular differentiation in TF-1 R132H cells and primary human IDH1 mutant AML patent samples treated ex vivo," Blood, 2014, 124(21):3734.
Hartmann et al. "Type and Frequency of IDH1 and IDH2 mutations are related to astrocytic and oligodendroglial differentiation and age: a study of 1010 diffuse gliomas" Acta Neuropathologica (2009) 118: 469-474.
Hashida, Design and Evaluation of Oral Administration Formulations, Jiho Inc., 1995, 172-185.
Hashida, Design and Evaluation of Oral Administration Formulations, Jiho Inc., 1995, 76-79.
Hemerly et al. "Identification of several novel non-p. R132 IDH1 variants in thyroid carcinomas," European Journal of Endocrinology, 2010, 163(5):747-755.
STN Tokyo, Registry No. 920847-34-3, Entered STN on Feb. 14, 2007, Chemical Abstracts Index Name "1,4-Benzodioxin-6-sulfonamide, 2,3-dihydro-N-[4-[[4-(2-methylphenyl)-1-piperazinyl]carbonyl]phenyl]-".
STN Tokyo, Registry No. 920875-39-4, Entered STN on Feb. 14, 2007, Chemical Abstracts Index Name "1,4-Benzodioxin-6-sulfonamide, 2,3-dihydro-N-[4-[[4-(2-hydroxyphenyl)-1-piperazinyl]carbonyl]phenyl]-".
STN Tokyo, Registry No. 920902-88-1, Entered STN on Feb. 14, 2007, Chemical Abstracts Index Name "1,4-Benzodioxin-6-sulfonamide, 2,3-dihydro-N-[4-[[4-(2-thienylmethyl)-I-piperazinyl]carbonyl]phenyl]-".
STN Tokyo, Registry No. 920921-09-1 Entered STN on Feb. 14, 2007, Chemical Abstracts Index Name "2H-1, 5-Benzodioxepin-7-sulfonamide, 3,4-dihydro-N-[4-[[4-(2pyridinyl)-1-piperazinyl]carbonyl]phenyl]-".
STN Tokyo, Registry No. 920924-42-1, Entered STN on Feb. 14, 2007, Chemical Abstracts Index Name "1,4-Benzodioxin-6-sulfonamide, 2,3-dihydro-N-[4-[[4-(2-pyridinylmethyl)-1-piperazinyl]carbonyl]phenyl]-".
STN Tokyo, Registry No. 941220-77-5, Entered STN on Jul. 4, 2007, Chemical Abstracts Index Name "2H-1, 5-Benzodioxepin-7-sulfonamide, 3,4-dihydro-N-[4-[(4-methyl-I-piperazinyl)carbonyl]phenyl]-".
Struys et al, Investigations by mass isotopomer analysis of the formation of D-2-hydroxyglutarate by cultured lymphoblasts from two patients with D-2-hydroxyglutaric aciduria, FEBS letters 92004 vol. 557, pp. 115-120.
Struys et al. "Mutations in the D-2-hydroxyglutarate dehydrogenase gene cause D-2-hydroxyglutaric aciduria" American Journal of Human Genetics, 2005. 76:358-360.
Struys, EA. et al. "Measurement of Urinary D- and L-2-Hydroxyglutarate Enantiomers by Stable-Isotope-Dilution LiquidChromatography-Tandem Mass Spectrometry after Derivatization with Diacetyi-L-Tartaric Anhydride." Clinical Chemistry (2004)501391-1395.
Supplementary European Search Report for EP15761216 dated Oct. 5, 2017.
Takagi et al. "Synthesis of poly(triazinylstyrene) containing nitrogen-bawed ligand and function as metal ion adsorbent and oxidation catalyst" Reactive & Functional Polymers (2006) vol. 31, pp. 1718-1724.

The radiation fact sheet published by the National Cancer Institute, http://www.cancer.gov/about-cancer/treatment/types/radiation-therapy/radiation-fact-sheet, reviewed Jun. 30, 2010.
Thompson, "Metabolic Enzymes as Oncogenes or Tumor Suppressors." The New England 18-22 Journal of Medicine, Feb. 19, 2009, vol. 360, No. 8, pp. 813-815; p. 813, p. 815, col. 1; Fig 1.
Van Schaftingen et al. "L-2-Hydroglutaric aciduria, a disorder of metabolite repair" J Inherit. Metab. Dis. (2009) vol. 32, pp. 135-142.
Wang et al "Facile Synthesis of 2,4-Dianiino-6-alkyi- or 6-Aryl-PyrimidineDerivatives" Journal of Heterocyclic Chemistry (2010) vol. 47 pp. 1056-1061.
Wang et al. "A novel ligand N,N?-di(2-pyridyl)-2,4-diamino-6-phenyl-1,3,5-triazine (dpdapt) and its complexes: [Cu(dpdapt)Cl2] and [Cu(dpdapt)(NO3)(H2O)] Â· NO3 Â· H2O" Polyhedron, 2006. vol. 25, Issue 1. pp. 195-202.
Ward, Patrick S, "The Common Feature of Leukemia-Associated IDH1 and IDH2 Mutations is a Neomorphic Enzyme Activity Converting [alpha]-Ketoglutarate to 2-Hydroxyglutarate" Cancer cell, vol:17,Nr:3,pp. 225-234, 2010.
Watanabe et al., "IDH1 Mutations Are Early Events in the Development of Astrocytomas and Oligodendrogliomas". American Journal of Pathology, Apr. 2009 (published online (Feb. 26, 2009), vol. 174, No. 4, pp. 1149-1153; Abstract, p. 1150, col. 1.
Wei Chao et al. Teaching Materials of the 12th Five-Year Paln for the Relevant Majors of Pharmacy in the Specialty and Polytechnic Colleges, Pharmacy (2nd edition), Henan Science and Technology Press, 2012.
Written Opinion of International Search Authority for PCT/CN2013/000009 dated Apr. 18, 2013.
Yampolsky et al. "The exchangeability of amino acids in proteins," Genetics, 2005, 170:1459-1472.
Yan et al., "IDH1 and IDH2 Mutations in Gliomas" The New England Journal of Medicine, 79 Feb. 18-22, 2009, vol. 360, No. 8, pp. 765-773.
Yrjola et al., "Discovery of novel cannabinoid receptor ligands by a virtual screening approach: Further development of 2,4,6-trisubstituted 1,3,5-triazines as CB2 agonists," European Journal of Pharmaceutical Sciences (2013) vol. 48, pp. 9-20.
Yuan et al. "Role of IDH1 gene mutation in the genesis of glioblastoma," Medical Journal of Wuhan University, 2011, 32(2):164-166.
Zhao et al: "Glioma-derived mutations in IDH1 dominantly inhibit IDH1 catalytic activity and induce HIF-1alpha", Science, vol. 324, No. 5924, Apr. 10, 2009 (Apr. 10, 2009), pp. 261-265.
Zheng et al. "Synthesis and antitumor evaluation of a novel series of triaminotriazine derivatives" Bioorganic & Medicinal Chemistry (2007) vol. 15, pp. 1815-1827.
Zuo et al. "Synthesis of 4-methyl-1,2,3-thiadiazole derivatives via ugi reaction and their biological activities," Journal of Agricultural and Food Chemistry, 2010, 58(5): 2755-2762.
Ho et al., "Triazine and pyrimidine based ROCK inhibitors with efficacy in spontaneous hypertensive rat model." Bioorganic & Medicinal Chemistry Letters (2009) vol. 19, pp. 6027-6031.
Holmes et al, 750 MHz 1H NMR spectroscopy characterisation of the complex metabolic pattern of urine from patients with inborn errors of metabolism: 2-hydroxyglutaric aciduria and maple syrup urine disease., Journal of Pharmaceutical and Biomedical Analysis (1997) vol. 15, pp. 1647-1659.
Huang et al., "N4-phenyl modifications of N2-(2-hydroxyl)ethyl-6-(pyrrolidin-1-yl)-1,3,5-triazine-2,4-diamines enhance glucocerebrosidase inhibition by small molecules with potential as chemical chaperones for Gaucher disease," Bioorganic & Medicinal Chemistry Letters (2007) vol. 12, pp. 5783-5789.
Im et al. "DNMT3A and IDH mutations in acute myeloid leukemia and other myeloid malignancies: Associations with prognosis and potential treatment strategies," Leukemia, 2014, 28:1774-1783.
International Search Report for PCT/CN2013/000068 dated Apr. 25, 2013.
International Search Report for PCT/US2010053624 dated Apr. 7, 2011.
International Search Report for PCT/US2016/057036 dated Jan. 12, 2017.

(56) References Cited

OTHER PUBLICATIONS

International Search Report for PCT/US2016/057042 dated Jan. 12, 2017.
International Search Report for PCT/US2016/064832 dated Feb. 16, 2017.
International Search Report for PCT/US2016/064845 dated May 4, 2017.
Irikura et al. "New s-Triazine Derivatives as Depressants for Reticuloendothelial Hyperfunction Induced by Bacterial Endotoxin" Journal of Medicinal Chemistry (2000) vol. 31, pp. 1081-1089.
Jana et al., "Synthesis and Antibacterial Activity of Some Novel 4-Benzyl-piperazinyl-s-triazine Derivatives." Asian Journal of Chemistry (2013) vol. 25, No. 1, pp. 186-190.
Jennings et al, Expression and mutagenesis of mammalian cytosolic NADP+-specific isocitrate dehydrogenase, Biochemistry (1997)vol. 36, pp. 13743-13747.
Johannessen et al. "Rapid conversion of mutant IDH1 from driver to passenger in model of human gliomagenesis," Molecular Cancer Resarch, 2016, 14(10): 976-83.
Johnson et al. "Relationships between drug activity in NCI preclinical in vitro and in vivo models and early clinical trials," British Journal of Cancer, 2001, 84(10): 1424-1431.
Kaila et al. "A convenient one-pot synthesis of trisubstituted 1,3,5-triazines through intermediary amidinothioureas" Tetrahedron Letters (2010) vol. 51, pp. 1486-1489.
Kelarev et al. "Synthesis and properties of sym-triazines. 10 Synthesis of 2,4-diamino-sym-triazines containing a sterically hindered phenol substituent" Chemistry of Heterocyclic Compounds (1992) vol. 28, No. 10, pp. 1189-1193.
Kim et al "Ser95, Asn97, and Thr78 are important for the catalytic function of porcine NADP-dependent isocitrate dehydrogenase" Protein Science (2005) 14: pp. 140-147.
Kim et al. "Identification and Functional Characterization of a Novel, Tissue-specific NAD1-dependent Isocitrate Dehydrogenase b Subunit Isoform" JBC. Dec. 24, 1999, vol. 274 No. 52 pp. 36866-36875.
Koshelev et al. "Synthesis of 1-3,7 N-substituted 2,4-diamino-1,3,5-triazines containing pyridyl groups" Russian Journal of Organic Chemistry (1995) vol. 31, No. 2, pp. 260-263.
Kranendijk et al. "IDH2 Mutations in Patients with D-2-Hydroxyglutaric Aciduria" Science (2010) vol. 330, p. 336.
Krell et al., "IDH mutations in tumorigenesis and their potential role as novel therapeutic targets" Future Oncology (2013) vol. 9, Iss 12, pp. 1923-1935.
Kumar et al. "Pharmaceutical solid dispersion technology: A strategy to improve dissolution of poorly water-soluable drugs," Recent Patents on Drug Delivery and Formulation, 2013, 7:111-121.
Kumar et al., "4-Anilinoquinoline triazines: A novel class of hybrid antimalarial agents" European Journal of Medicinal Chemistry (2011) vol. 46, pp. 676-690.
Kumar et al., "Synthesis and bioevaluation of hybrid 4-aminoquinoline triazines as a new class of antimalarial agents," Bioorganic & Medicinal chemistry Letters (2008) vol. 18, pp. 6530-6533.
Lazzarino et al. "Mitoxantrone and etoposide: An effective regimen for refractory or relapsed acute myelogenous leukemia," European Journal of Haematology, 1989, 43:411-416.
Lee et al. "Combinatorial Solid-Phase Synthesis of 6-Aryl-1,3,4-triazines via Suzuki Coupling" Aust. J. Chem. (2011) vol. 64, pp. 540-544.
Levis et al. "Results of a first-in-human, phase I/II trial of ASP2215, a selective, potent inhibitor of FLT3/Axl in patients with relapsed or refractory (R/R) acute myeloid leukemia," Journal of Clinical Oncology, 2015, 33(15 suppl):7003.
Liu et al. "Inhibition of Cancer-Associated Mutant Isocitrate Dehydrogenases: Synthesis, Structure—Activity Relationship, and Selective Antitumor Activity" Journal of Medicinal Chemistry (2014) vol. 57, pp. 8307-8318.
Lou. "IDH1: function follows form." SciBX, 2009, 1-2.
Lowe, "Good old medicinal chemistry: what can you get away with?," Blog "In the Pipeline," entry of Nov. 2, 2010.
Lutker et al, "Crystal Polymorphism in a Carbamazepine Derivative: Oxcarbazepine". NIH Public Access. J Pharm Sci. Feb. 2010 ; 99(2): 794-803. doi: 10.1002/jps.21873.
Madsen-Duggan et al. "Lead optimization of 5.6-diarylpyridines as CB1 receptor inverse agonists" Bioorganic & Medicinal Chemistry Letters (2007) vol. 17, pp. 2031-2035.
Maison, "Multicomponent synthesis of novel amino acid-nucleobase chimeras: a versatile approach to PNA-monomers," Bioorganic & Medicinal Chemistry (2000) vol. 8, pp. 1343-1360.
May et al, How many species are there on earth, Science (1988) vol. 241, p. 1441.
McRobbie et al. "MRI from Picture to Proton," Cambridge University Press, 2007, pp. 307-308.
Mikhailichenko, S. N., et al. "sym-triazines. 7. Hydrolysis and cyclization of 1, 3, 5-triazine series mononitriles." Chemistry of Heterocyclic Compounds 42.5 (2006): 642-647.
Mikhaylichenko, Svetlana, et al. "Synthesis and structure of new 1, 2, 3-triazolyl substituted 1, 3, 5-triazines." European Journal of Chemistry 3.1 (2012): 1-9.
Moreno et al. "Identification of diamine linkers with differing reactivity and their applicationin the synthesis of melamine dendrimers" Tetrahedron Letters (2008) vol. 49, pp. 1152-1154.
Moreno et al. "Molecular recognition in dendrimers based on melamine" Polymer Preprints (2005) vol. 46, No. 2, pp. 1127.
Pansuriya et al. "Somatic mosaic IDH1 and IDH2 mutations are associated with echondroma and spindle cell hemangioma in Ollier disease and Maffucci syndrome," Nature Genetics, 2011, 43(12):1256-1263.
Paronikyan et al. "Synthesis and biological activity of 3-piperazinylpyrano [3,4-C] pyridines" Armyanskii Khimicheskii Zhurnal (1990) vol. 43, No. 8, pp. 518-523.
Parsons et al. "An Integrated Genomic Analysis of Human Glioblastoma Multiforme" Science vol. 321 (2008) pp. 1807-1812 and Supplemental Data.
Pitts et al., "Rapid Synthesis of Triazine Inhibitors of Inosine Monophosphate Dehydrogenase," Bioorganic & Medicinal Chemistry Letters (2002) vol. 12, pp. 2137-2140.
Pollard et al, "Cancer. Puzzling patterns of predisposition." Science. Apr. 10, 2009, vol. 324, 1-5,15-16, 18-22,35-38 No. 5924, pp. 192-194.
Popovici-Muller, Janeta et al. Discovery of the First Potent Inhibitors of Mutant IDH1 That Lower Tumor2-HG in Vivo. ACS Medicinal Chemistry Letters. Sep. 17, 2012 (Sep. 17, 2012), vol. 3, No. 10, 850-855.
Pubchem CID 4078245 [online]; Sep. 13, 2005 [retrieved on Feb. 4, 2012]; retrieved from http://pubchem.ncbi.nlm.nih.gov/; 2d-structure.
Pubchem CID 4854170 [online]; Sep. 17, 2005 [retrieved on Feb. 4, 2012]; retrieved from http://pubchem.ncbi.nlm.nih.gov/; 2d-structure.
Ramos et al. "Current approaches in the treatment of relapsed and refractory acute myeloid leukemia," Journal of Clinical Medicine, 2015, 4(4):665-695.
Rao et al., "Polymorphism in Drugs and its Significance in Therapeutics". Journal of Scientific & Industrial Research vol. 46 Oct. 1987 pp. 450-455.
Dai et al. "Effect of itraconazole, food, and ethnic origin on the pharmacokinetics of ivosidenib in healthy subjects," ClinicalTrials. gov: NCT03071770, NCT02579707, and NCT02831972.
Deng et al. "A review of food-drug interactions on oral drug absorption," Drugs, 2017, 77:1833-1855.
Raynaud et al. "Absence of R140Q Mutation of Isocitrate Dehydrogenase 2 in Gliomas and Breast Cancers" Oncology Letters (2010) vol. 1, No. 5, pp. 883-884.
Registry (STN) [online], Aug. 23, 2006 [Retrieved on Jan. 29, 2016] CAS Registration No. 903862-76-0.
Registry (STN) [online], Aug. 23, 2006 [Retrieved on Jan. 29, 2016] CAS Registration No. 903869-26-1.
Registry (STN) [online], Apr. 13, 2007 [Retrieved on Jan. 29, 2016] CAS Registration No. 929819-92-1.
Registry (STN) [online], Apr. 13, 2007 [Retrieved on Jan. 29, 2016] CAS Registration No. 929971-43-7.

(56) References Cited

OTHER PUBLICATIONS

Registry (STN) [online], Jul. 3, 2008, CAS Registration No. 1032461-94-1.
Registry (STN) [online], Jul. 3, 2008, CAS Registration No. 1032470-22-6.
Registry (STN) [online], Jul. 4, 2008, CAS Registration No. 1032747-65-1.
Registry (STN) [online], Apr. 19, 2009 [Retrieved on Jan. 29, 2016] CAS Registration No. 1136498-70-8.
Registry (STN) [online], Aug. 27, 2009 [Retrieved on Jan. 29, 2016] CAS Registration No. 1176756-98-1.
Registry (STN) [online], Apr. 16, 2010, CAS Registration No. 1219379-97-1.
Reitman et al. "Isocitrate Sehydrogenase 1 and 2 Mutations in Cancer: Alterations at a Crossroads of Cellular Metabolism" Journal of the National Cancer Institute, vol. 102, No. 13, pp. 932-941 (2010).
Rohle et al. "An Inhibitor of Mutant IDH1 Delays Growth and Promotes Differentiation of Glioma Cells" Science, vol. 340, No. 6132 pp. 626-630 (2013).
Rzem et al. "A gene encoding a putative FAD-dependent L-2-hydroxyglutarate dehydrogenase is mutated in L-2-hydroxyglutaric aciduria," PNAS, 2004, 101(48):16849-16854.
Scharn et al. "Spatially Addressed Synthesis of Amino- and Amino-Oxy-Substituted 1,3,5-Triazine Arrays on Polymeric Membranes" Journal of Combinatorial Chemistry (2000) vol. 2, No. 4, pp. 361-369.
Search Report for SG 11201600185U dated Nov. 16, 2016.
Serajuddin et al. "Solid dispersion of poorly water-soluable drugs: early promises, subsequent problems, and recent breakthroughs," Journal of Pharmaceutical Sciences, 1999, 88(10):1058-1066.
Shafer et al. "Update on rational tareted therapy in AML," Blood Reviews, 2016, 30:275-283.
Shahin et al., "Elaborate ligand-based modeling and subsequent synthetic exploration unveil new nanomora Ca2+/Calmodulin-dependent protein kinase II inhibitory leads" Bioorganic & Medicinal Chemistry (2012) vol. 20, pp. 377-400.
Shin et al. "The Role of Mutations in Epigenetic Regulators in Myeloid Malignancies" Nature Reviews Cancer (2012) vol. 12, No. 9, pp. 599-612.
Shuichi et al. "Long-term follow-up of the randomized JALSG AML 201 study comparing high dose Ara-C therapy with conventional consolidation therapy in adult acute myeloid leukemia (AML)," Blood, 2008, 112(11):135.
Sirkanyan, S.N. et al Synthesis of new derivatives of piperazine-substituted pyrano[3,4-c]pyridines. Hayastani Kimiakan Handes 2009, vol. 62, No. 3-4 pp. 378-385. English Abstract Only.
Sonoda et al. "Analysis of IDH1 and IDH2 mutations in Japanese glioma patients" Cancer Science, vol. 100, No. 10, pp. 1996-1998.
Sosnovik et al. "Emerging concepts in molecular MRI." Curr. Op. Biotech., 2007, 18, 4-10.
STN file CA, Registry No. 1023444-33-8, entered STN on May 29, 2008, Chemical Abstracts Index Name "Benzenesulfonamide, 3-[[4-(1,3-benzodioxol-5-ylmethyl)-1-piperazinyl]carbonyl]-N-(4-butylphenyl)-4-methyl-".
STN File CA, Registry No. 1090629-29-0, entered STN on Dec. 28, 2008, Chemical Abstracts Index Name "Benzenesulfonamide, 3-[[4-[(2,5-dimethoxyphenyl)methyl]-1-piperazinyl]carbonyl]-N-(4-methoxyphenyl)-4-methyl-".
STN File CA, Registry No. 134538-28-6, entered STN on Jun. 28, 1991, Chemical Abstracts Index Name "1H-Pyrano[3,4-c]pyridine-5-carbonitrile,3,4-dihydro-3,3-dimethyl-6-[4-(1-oxobutyl)-1-piperazinyl]-8-phenyl-", disclosed in Paronikyan et al. Armyanskii Khimicheskii Zhurnal, 1990, vol. 43, No. 8.
STN File CA, Registry No. 134538-29-7, entered STN on Jun. 28, 1991, Chemical Abstracts Index Name "1H-Pyrano[3,4-c]pyridine-5-carbonitrile,3,4-dihydro-3,3-dimethyl-6-[4-(2-methyl-1-oxopropyl)-1-piperazinyl]-8-phenyl-", disclosed in Paronikyan et al. Armyanskii Khimicheskii Zhurnal, 1990, vol. 43, No. 8.

STN File CA, Registry No. 134538-30-0, entered STN on Jun. 28, 1991, Chemical Abstracts Index Name "1H-Pyrano[3,4-c]pyridine-5-carbonitrile,6-(4-benzoyl-1-piperazinyl)-3,4-dihydro-3,3-dimethyl-8-phenyl-", disclosed in Paronikyan et al. Armyanskii Khimicheskii Zhurnal, 1990, vol. 43, No. 8.
STN File CA, Registry No. 134538-31-1, entered STN on Jun. 28, 1991, Chemical Abstracts Index Name "1H-Pyrano[3,4-c]pyridine-5-carbonitrile,6-[4-(2-furanylcarbonyl)-1-piperazinyl]-3,4-dihydro-3,3-dimethyl-8-phenyl-", disclosed in Paronikyan et al. Armyanskii Khimicheskii Zhurnal, 1990, vol. 43, No. 8.
STN File CA, Registry No. 380466-24-0 entered STN on Jan. 4, 2002, Chemical Abstracts Index Name "Benzenesulfonamide, N-methyl-N-phenyl-3-[[4-(2-pyridinyl)-1-piperazinyl]carbonyl]".
STN file CA, Registry No. 713505-78-3, entered STN on Jul. 21, 2004, Chemical Abstracts Index Name "1-Piperazinecarboxylic acid, 4-[4-methyl-3-[(phenylamino)sulfonyl]benzoyl]-, ethyl ester".
STN File CA, Registry No. 736168-79-9 entered STN on Aug. 31, 2004, Chemical Abstracts Index Name "Benzenesulfonamide, 3,4-difluoro-N-[3-334-(phenylmethyl0-1-piperazinyl]carbonyl]phenyl".
STN File CA, Registry No. 847757-57-7, entered STN on Apr. 1, 2005, Chemical Abstracts Index Name "Benzenesulfonamide, 3-[[4-(1,3-benzodioxol-5-ylmethyl)-1-piperazinyl]carbonyl]-N-(4-ethoxyphenyl)-N,4-dimethyl-" or "Piperazine, 1-(1,3-benzodioxol-5-ylmethyl)-4-[5-[[(4-ethoxyphenyl)methylamino]sulfonyl]-2-methylbenzoyl]-".
STN Registry, L23 Answer 2 of 3 (CAS No. 1032450-21-7), Database: ASINEX Ltd.,Entered STN: Jul. 3, 2008 (Jul. 3, 2008).
STN Registry. L23 Answer 1 of 3 (CAS No. 1038821-72-5),Database: ChemDB (University of California Irvine), Entered STN: Aug. 5, 2008 (Aug. 5, 2008).
STN Tokyo, Registry No. 1001833-18-6, Entered STN on Feb. 6, 2008, Chemical Abstracts Index Name "1,4-Benzodioxin-6-sulfonamide, 2,3-dihydro-N-[4-[(4-methyl-I-piperazinyl)carbonyl]phenyl]-".
STN Tokyo, Registry No. 1030142-35-8, Entered STN on Jun. 24, 2008, Chemical Abstracts Index Name "1,4-Benzodioxin-6-sulfonamide, 2,3-dihydro-N-[4-[[4-[(5-methyl-3-isoxazolyl)methyl]-I-piperazinyl]carbonyl]phenyl]-".
STN Tokyo, Registry No. 1031531-78-8, Entered STN on Jun. 29, 2008 Chemical Abstracts Index Name "1,4-Benzodioxin-6-sulfonamide, N-4[4-[(4-acetyl-1-piperazinyl)carbonyl]phenyl]-2,3-dihydro-".
STN Tokyo, Registry No. 1057928-35-4, Entered STN on Oct. 7, 2008, Chemical Abstracts Index Name "1,4-Benzodioxin-6-sulfonamide, 2,3-dihydro-N-[4-[[4-(2-pyridinyl)-I-piperazinyl]carbonyl]phenyl]-".
STN Tokyo, Registry No. 1240875-00-6, entered STN on Sep. 14, 2010, Chemical Abstracts Index Name "1,4-Benzodioxin-6-sulfonamide, 2,3-dihydro-N-[4-[[4-(2-thiazolyl)-1-piperazinyl]carbonyl]phenyl]-".
STN Tokyo, Registry No. 748791-86-8, Entered STN on Sep. 21, 2004, Chemical Abstracts Index Name "1,4-Benzodioxin-6-sulfonamide, N-[4-[[4-(2-furanylcarbonyl)-1-piperazinyl]carbonyl]phenyl]-2,3-dihydro-".
STN Tokyo, Registry No. 878469-24-0, Entered STN on Mar. 29, 2006, Chemical Abstracts Index Name "1,4-Benzodioxin-6-sulfonamide, 2,3-dihydro-N-[4-[[4-(2-pyrimidinyl)-1-piperazinyl]carbonyl]phenyl]-".
STN Tokyo, Registry No. 878474-39-6, Entered STN on Mar. 29, 2006, Chemical Abstracts Index Name "1,4-Benzodioxin-6-sulfonamide, 2,3-dihydro-N-[4[(4-phenyl-1-piperazinyl)carbonyl]phenyl]-".
STN Tokyo, Registry No. 878590-33-1, Entered STN on Mar. 30, 2006, Chemical Abstracts Index Name "1,4-Benzodioxin-6-sulfonamide, 2,3-dihydro-N[4-{{4-(tetrahydro-2-furanyl)methyl]-1-piperazinyl]carbonyl]phenyl]-".
STN Tokyo, Registry No. 878943-66-9 Entered STN on Apr. 2, 2006, Chemical Abstracts Index Name "1,4-Benzodioxin-6-sulfonamide, 3,4-dihydro-N-[[4-(2-pyrimidinyl)-1-piperazinyl)carbonyl]phenyl]-".
STN Tokyo, Registry No. 878956-06-0, Entered STN on Apr. 2, 2006, Chemical Abstracts Index Name "1,4-Benzodioxin-6-

(56) References Cited

OTHER PUBLICATIONS sulfonamide, N-[4- [[4-(cyclopropylcarbonyl)-1-piperazinyl]carbonyl]phenyl]-2,3-dihydro-".
STN Tokyo, Registry No. 920679-46-5, Entered STN on Feb. 13, 2007, Chemical Abstracts Index Name "1,4-Benzodioxin-6-sulfonamide, 2,3-dihydro-N-[4-[[4-(4-pyridinyl)-1-piperazinyl]carbonyl]phenyl]-".
STN Tokyo, Registry No. 920822-52-2, Entered STN on Feb. 14, 2007, Chemical Abstracts Index Name "1,4-Benzodioxin-6-sulfonamide, N-[4-[[4-(4-fluoropheyl)-1-piperazinyl]carbonyl]phenyl]-2,3dihydro-".
STN Tokyo, Registry No. 920824-56-2, Entered STN on Feb. 14, 2007, Chemical Abstracts Index Name "1,4-Benzodioxin-6-sulfonamide, 2,3-dihydro-N-[4-[[4-(3-thienylmethyl)-1-piperazinyl]carbonyl]phenyl]-".
U.S. Appl. No. 13/810,410, filed Mar. 28, 2013, Janeta Popovici-Muller.
U.S. Appl. No. 15/064,874, filed Mar. 9, 2016, Janeta Popovici-Muller.
U.S. Appl. No. 13/745,005, filed Jan. 18, 2013, Rene M. Lemieux.
U.S. Appl. No. 14/988,661, filed Jan. 5, 2016, Rene M. Lemieux.
U.S. Appl. No. 15/279,146, filed Sep. 28, 2016, Janeta Popovici-Muller.
U.S. Appl. No. 15/809,325, filed Nov. 10, 2017, Janeta Popovici-Muller.
U.S. Appl. No. 16/427,691, filed May 31, 2019, Janeta Popovici-Muller.
U.S. Appl. No. 16/893,750, filed Jun. 5, 2020, Janeta Popovici-Muller.
U.S. Appl. No. 14/373,154, filed Jul. 18, 2014, Janeta Popovici-Muller.
U.S. Appl. No. 15/196,842, filed Jun. 29, 2016, Janeta Popovici-Muller.
U.S. Appl. No. 14/341,426, filed Jul. 25, 2014, Rene M. Lemieux.
U.S. Appl. No. 15/347,407, filed Nov. 9, 2016, Rene M. Lemieux.
U.S. Appl. No. 15/915,213, filed Mar. 8, 2018, Rene M. Lemieux.
U.S. Appl. No. 15/125,884, filed Sep. 13, 2016, Chong-Hui Gu.
U.S. Appl. No. 15/125,880, filed Sep. 13, 2016, Chong-Hui Gu.
U.S. Appl. No. 15/949,750, filed Apr. 10, 2018, Chong-Hui Gu.
U.S. Appl. No. 16/460,111, filed Jul. 2, 2019, Chong-Hui Gu.
U.S. Appl. No. 17/013,083, filed Sep. 4, 2020, Chong-Hui Gu.
U.S. Appl. No. 15/767,813, filed Apr. 12, 2018, Samuel V. Agresta.
U.S. Appl. No. 15/767,822, filed Apr. 12, 2018, Samuel V. Agresta.
U.S. Appl. No. 16/846,976, filed Apr. 13, 2020, Samuel V. Agresta.
U.S. Appl. No. 15/781,019, filed Jun. 1, 2018, Bin Wu.
U.S. Appl. No. 16/079,802, filed Aug. 24, 2018, Sung Eun Choe.
U.S. Appl. No. 16/869,238, filed May 7, 2020, Sung Eun Choe.
Garcia et al, "Effect of Food on the Bioavailability of Palbociclib" Cancer Chemother Pharmacol. Mar. 2017, 79(3): p. 527-533.
Lee et al, "Effects of Food Intake on the Pharmacokinetic Properties of Mirabegron Oral Controlled-Absorption System: a Singal-Dose, randomized, Crossover Study in Healthy Adults" Elsevier, Clin Ther. Mar. 2013, 35 (3) p. 333-41.
Narasimhan et al, "Effects of Food on the Pharmacokinetics of Ponatinib in Healthy Subjects" Journal of Clinical Pharmacy and Therapeutics, 2013, 38, p. 440-444.

* cited by examiner

THERAPY FOR TREATING MALIGNANCIES

CLAIM OF PRIORITY

This application claims priority from U.S. provisional patent application No. 62/682,808 filed Jun. 8, 2018, which is incorporated herein by reference in its entirety.

FIELD

Provided herein are methods of treating malignancies including hematological malignancies and solid tumors characterized by the presence of a mutant allele of IDH1. In one embodiment, the methods for treating a malignancy comprise orally administering an IDH1 inhibitor with or without food to a subject that has avoided a high-fat meal prior to the administration of the IDH1 inhibitor.

BACKGROUND

Isocitrate dehydrogenases (IDHs) catalyze the oxidative decarboxylation of isocitrate to 2-oxoglutarate (i.e., α-ketoglutarate). These enzymes belong to two distinct subclasses, one of which utilizes NAD(+) as the electron acceptor and the other NADP(+). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH1 (isocitrate dehydrogenase 1 (NADP+), cytosolic) is also known as IDH; IDP; IDCD; IDPC or PICD. The protein encoded by this gene is the NADP(+)-dependent isocitrate dehydrogenase found in the cytoplasm and peroxisomes. It contains the PTS-1 peroxisomal targeting signal sequence. The presence of this enzyme in peroxisomes suggests roles in the regeneration of NADPH for intraperoxisomal reductions, such as the conversion of 2, 4-dienoyl-CoAs to 3-enoyl-CoAs, as well as in peroxisomal reactions that consume 2-oxoglutarate, namely the alpha-hydroxylation of phytanic acid. The cytoplasmic enzyme serves a significant role in cytoplasmic NADPH production.

The human IDH1 gene encodes a protein of 414 amino acids. The nucleotide and amino acid sequences for human IDH1 can be found as GenBank entries NM_005896.2 and NP_005887.2 respectively. The nucleotide and amino acid sequences for IDH1 are also described in, e.g., Nekrutenko et al., Mol. Biol. Evol. 15:1674-1684 (1998); Geisbrecht et al., J. Biol. Chem. 274:30527-30533 (1999); Wiemann et al., Genome Res. 11:422-435 (2001); The MGC Project Team, Genome Res. 14:2121-2127 (2004); Lubec et al., Submitted (December 2008) to UniProtKB; Kullmann et al., Submitted (June 1996) to the EMBL/GenBank/DDBJ databases; and Sjoeblom et al., Science 314:268-274 (2006).

Non-mutant, e.g., wild type, IDH1 catalyzes the oxidative decarboxylation of isocitrate to α-ketoglutarate thereby reducing $NAD^+$ ($NADP^+$) to NADH (NADPH), e.g., in the forward reaction:

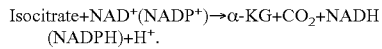

Isocitrate+$NAD^+$($NADP^+$)→α-KG+$CO_2$+NADH (NADPH)+$H^+$.

It has been discovered that mutations of IDH1 present in certain cancer cells result in a new ability of the enzyme to catalyze the NADPH-dependent reduction of α-ketoglutarate to R(–)-2-hydroxyglutarate (2HG). The production of 2HG is believed to contribute to the formation and progression of cancer (Dang, L et al, Nature 2009, 462:739-44).

The development of selective inhibitors of IDH1 mutant enzymes has provided the possibility of therapeutic benefit to cancer patients carrying the IDH1 mutations. COMPOUND 1, an inhibitor of IDH1 mutant enzymes described herein is a therapeutic agent for the treatment of malignancies characterized by the presence of a mutant allele of IDH1, e.g., hematologic malignancies (e.g., acute myelogenous leukemia (AML)), e.g., solid tumors (e.g., cholangiocarcinoma, glioma and chondrosarcoma). Although therapeutic agents can be administered via many routes of administration, the oral route is often preferred due to its convenience. Bioavailability after oral administration of therapeutic agents can be affected by a myriad of issues, including food effects, poor absorption or susceptibility to first pass metabolism. In order for COMPOUND 1 to be administered orally as a therapeutic agent for the treatment of malignancies characterized by the presence of a mutant allele of IDH1, a favorable bioavailability profile must be achieved.

SUMMARY

The disclosure provides methods for treating malignancies by the presence of a mutant allele of IDH1, comprising administering to a subject an oral dosage form comprising a therapeutically effective amount of a mutant isocitrate dehydrogenase 1 (IDH1) inhibitor wherein the mutant IDH1 inhibitor is (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide, having the following formula:

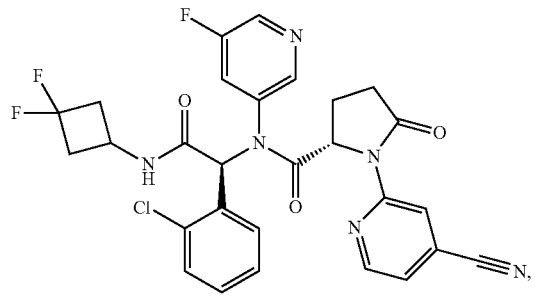 [SMILES: N#Cc1ccnc(N2C(=O)CC[C@H]2C(=O)N(c2cncc(F)c2)[C@H](C(=O)NC2CC(F)(F)C2)c2ccccc2Cl)c1]

or a pharmaceutically acceptable salt, solvate, tautomer, stereoisomer, isotopologue, prodrug, or a polymorph thereof (COMPOUND 1) wherein the compound is administered with or without food and wherein if the compound is administered with food, the food is not a high-fat meal.

In an embodiment, the oral dosage form is administered substantially contemporaneously with food. In certain embodiments, the therapeutically effective amount of the oral dosage form is administered within 10 minutes before or after ingesting food. In some embodiments, the therapeutically effective amount of the oral dosage form is administered within 30 minutes before or after ingesting food. In some embodiments, the therapeutically effective amount of the oral dosage form is administered within 60 minutes before or after ingesting food. In some embodiments, the therapeutically effective amount of the oral dosage form is administered within 90 minutes before or after ingesting food. In some embodiments, the therapeutically effective amount of the oral dosage form is administered within 120 minutes before or after ingesting food. In some embodiments, the therapeutically effective amount of the oral dosage form is administered within 180 minutes before or after ingesting food.

In an embodiment, the oral dosage form is administered without food. In some embodiments, the therapeutically effective amount of the oral dosage form is administered at least 60 minutes before ingesting food. In some embodiments, the therapeutically effective amount of the oral dosage form is administered at least 90 minutes before ingesting food. In some embodiments, the therapeutically effective amount of the oral dosage form is administered at least 120 minutes before ingesting food. In some embodiments, the therapeutically effective amount of the oral dosage form is administered at least 180 minutes before ingesting food. In further embodiments, the therapeutically effective amount of the oral dosage form is administered at least 60 minutes after ingesting food. In some embodiments, the therapeutically effective amount of the oral dosage form is administered at least 90 minutes after ingesting food. In some embodiments, the therapeutically effective amount of the oral dosage form is administered at least 120 minutes after ingesting food. In some embodiments, the therapeutically effective amount of the oral dosage form is administered at least 180 minutes after ingesting food.

In some embodiments the oral dosage form is administered to a subject that has not ingested a high-fat meal for at least 30 minutes before administration of the oral dosage form. In some embodiments the oral dosage form is administered to a subject that has not ingested a high-fat meal for at least 60 minutes before administration of the oral dosage form. In some embodiments the oral dosage form is administered to a subject that has not ingested a high-fat meal for at least 90 minutes before administration of the oral dosage form. In some embodiments the oral dosage form is administered to a subject that has not ingested a high-fat meal for at least 120 minutes before administration of the oral dosage form. In some embodiments the oral dosage form is administered to a subject that has not ingested a high-fat meal for at least 180 minutes before administration of the oral dosage form. In further embodiments the oral dosage form is administered to a subject that has not ingested a high-fat meal for at least 60 minutes after administration of the oral dosage form. In some embodiments the oral dosage form is administered to a subject that has not ingested a high-fat meal for at least 90 minutes after administration of the oral dosage form. In some embodiments the oral dosage form is administered to a subject that has not ingested a high-fat meal for at least 120 minutes after administration of the oral dosage form. In some embodiments the oral dosage form is administered to a subject that has not ingested a high-fat meal for at least 180 minutes after administration of the oral dosage form.

In certain embodiments, the $C_{max}$ of COMPOUND 1 is between 1500 ng/mL and 3100 ng/mL. In certain embodiments, the $C_{max}$ of COMPOUND 1 is between 1800 ng/mL and 2800 ng/mL. In one aspect of the invention, the oral dosage form comprises a therapeutically effective amount of COMPOUND 1 as part of a solid dispersion. In some embodiments, the solid dispersion comprises a partly water-soluble polymer. In some embodiments, the solid dispersion comprises a water-soluble polymer. In some embodiments, the polymer is a cellulose polymer. In some embodiments, the polymer is selected from hydroxypropylmethylcellulose acetate succinate (HPMCAS), polyvinyl acetate phthalate (PVAP), hydroxypropylmethylcellulose (HPMC) and hydroxypropylmethylcellulose phthalate (HPMCP). In some embodiments, the polymer is HPMCAS.

In one embodiment, the solid dispersion is a spray-dried dispersion.

In some embodiments, the solid dispersion comprises between about 30 and 70% w/w COMPOUND 1. In some embodiments, the solid dispersion comprises between about 40 and 60% w/w COMPOUND 1. In some embodiments, solid dispersion comprises about 50% w/w COMPOUND 1. In some embodiments, the solid dispersion comprises between about 15 and 35% w/w COMPOUND 1. In some embodiments, the solid dispersion comprises about 25% w/w COMPOUND 1.

In some embodiments, the dispersion is an amorphous dispersion.

In some embodiments, the oral dosage form further comprises a surfactant. In certain embodiments, the surfactant is vitamin E tocopheryl polyethylene glycol succinate (Vitamin E TPGS). In some embodiments, the oral dosage form further comprises a filler. In certain embodiments, the filler is microcrystalline cellulose. In some embodiments, the oral dosage form further comprises a disintegrant. In certain embodiments, the disintegrant is croscarmellose sodium. In some embodiments, the oral dosage form further comprises a wetting agent. In certain embodiments, the wetting agent is sodium lauryl sulfate. In some embodiments, the oral dosage form further comprises a glidant. In certain embodiments the glidant is colloidal silicon dioxide. In some embodiments, the oral dosage form further comprises a lubricant. In certain embodiments, the lubricant is magnesium stearate.

In one embodiment, the oral dosage form comprises from between about 25% w/w to about 35% w/w of COMPOUND 1, from between about 25% w/w to about 35% w/w of hypromellose acetate succinate (HPMCAS), from between about 25% w/w to about 35% w/w of microcrystalline cellulose, from between about 5% w/w to about 7% w/w croscarmellose sodium, from between about 0.5% w/w to about 1.5% w/w sodium lauryl sulfate, about from between about 1% w/w to about 3% w/w colloidal silicon dioxide, and rom between about 0.5% w/w to about 2.5% w/w of magnesium stearate, thereby totaling 100% by weight of the oral dosage form. In a further embodiment, the oral dosage form comprises about 30% w/w of COMPOUND 1, about 30% w/w of hypromellose acetate succinate (HPMCAS), about 29.5% w/w of microcrystalline cellulose, about 6% w/w croscarmellose sodium, about 1% w/w sodium lauryl sulfate, about 2% w/w colloidal silicon dioxide, and about 1.5% w/w of magnesium stearate.

In one embodiment, the oral dosage form is a tablet.

In one embodiment, the therapeutically effective amount of COMPOUND 1 is about 20 to 2000 mg. In a further embodiment, the therapeutically effective amount of COMPOUND 1 is about 50 to 1000 mg. In a further embodiment, the therapeutically effective amount of COMPOUND 1 is about 100-600 mg. In a further embodiment, the therapeutically effective amount of COMPOUND 1 is about 250-500 mg. In a further embodiment, the therapeutically effective amount of COMPOUND 1 is about 500 mg (e.g., is 500 mg).

In one embodiment, the oral dosage form is administered once a day. In another embodiment, the oral dosage form is administered twice a day.

In one embodiment, the therapeutically effective amount of COMPOUND 1 is administered as a single tablet comprising 500 mg COMPOUND 1. In another embodiment, the therapeutically effective amount of COMPOUND 1 is administered as two tablets comprising 250 mg COMPOUND 1 each. In another embodiment, the therapeutically effective amount of COMPOUND 1 is administered as four tablets comprising 125 mg COMPOUND 1 each. In another embodiment, the therapeutically effective amount of COMPOUND 1 is administered as five tablets comprising 100 mg COMPOUND 1 each.

In one aspect of the invention, the malignancy is a hematologic malignancy. In one embodiment, the hematologic malignancy is acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma. In one embodiment, the hematologic malignancy is advanced. In one embodiment, the hematologic malignancy is relapsed or refractory. In one embodiment, the malignancy is acute myelogenous leukemia (AML). In one embodiment the acute myelogenous leukemia (AML) is relapsed or refractory.

In another aspect of the invention, the malignancy is a solid tumor. In one embodiment, the solid tumor is selected from glioma, intrahepatic cholangiocarcinomas (IHCC), chondrosarcoma, prostate cancer, colon cancer, melanoma, and non-small cell lung cancer (NSCLC). In a further embodiment, the solid tumor is intrahepatic cholangiocarcinoma.

In one aspect of the invention, the malignancy (e.g., the solid tumor) is advanced.

In one aspect of the invention, the malignancy (e.g., the solid tumor) is relapsed or refractory.

In one aspect of the invention, the IDH1 mutation is an IDH1 R132X mutation. In one embodiment, the IDH1 mutation is an IDH1 R132H, R132C, R132L, R132V, R132S or R132GF mutation.

The disclosure also provides an article of manufacture comprising:

an oral dosage form comprising a therapeutically effective amount of a mutant isocitrate dehydrogenase 1 (IDH1) inhibitor wherein the mutant IDH1 inhibitor is (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide, having the following formula:

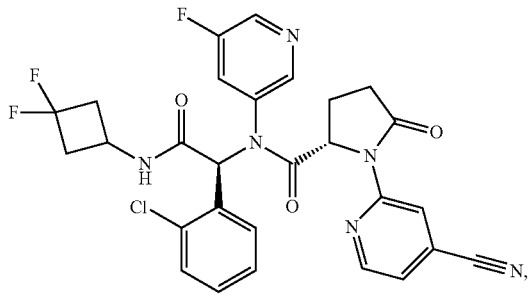 [SMILES: N#Cc1ccnc(N2C(=O)CC[C@H]2C(=O)N(c2cncc(F)c2)[C@H](C(=O)NC2CC(F)(F)C2)c2ccccc2Cl)c1]

or a pharmaceutically acceptable salt, solvate, tautomer, stereoisomer, isotopologue, prodrug, or a polymorph thereof (COMPOUND 1) in a packaging material; and
a package insert contained within the packaging material indicating that the oral dosage form should be taken with or without food and avoiding a high-fat meal.

The disclosure also provides an article of manufacture comprising: an oral dosage form comprising a therapeutically effective amount of a mutant isocitrate dehydrogenase 1 (IDH1) inhibitor wherein the mutant IDH1 inhibitor is (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide, having the following formula:

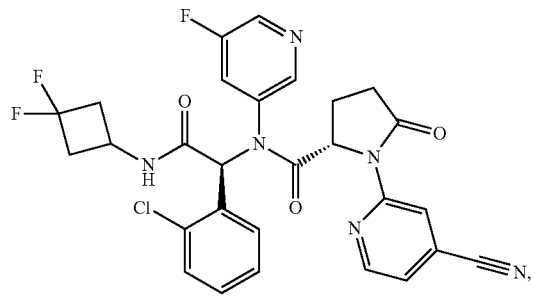 [SMILES: N#Cc1ccnc(N2C(=O)CC[C@H]2C(=O)N(c2cncc(F)c2)[C@H](C(=O)NC2CC(F)(F)C2)c2ccccc2Cl)c1]

or a pharmaceutically acceptable salt, solvate, tautomer, stereoisomer, isotopologue, prodrug, or a polymorph thereof (COMPOUND 1) in a packaging material; and
a label affixed to or printed on the packaging material indicating that the oral dosage form should be taken with or without food and avoiding a high-fat meal.

In one embodiment, the solid dosage form is a tablet.

In one embodiment, the label or package insert further indicates that the oral dosage form is administered once daily.

In one embodiment, the therapeutically effective amount of COMPOUND 1 is about 50 mg to about 2000 mg. In one embodiment, the therapeutically effective amount of COMPOUND 1 is about 100 mg to about 1000 mg. In one embodiment, the therapeutically effective amount of COMPOUND 1 is about 200 mg to about 600 mg. In one embodiment, the therapeutically effective amount of COMPOUND 1 is about 250 mg to about 500 mg. In a further embodiment, the therapeutically effective amount of COMPOUND 1 is about 500 mg, e.g., 500 mg.

In one embodiment, the label or the package insert further indicates that the oral dosage form is for treating malignancies associated with an IDH1 mutation. In one embodiment, the label or the package insert further indicates that the oral dosage form is for treating acute myelogenous leukemia (AML). In a further embodiment, the label or the package insert further indicates that the oral dosage form is for treating relapsed or refractory acute myelogenous leukemia (AML).

In one embodiment, COMPOUND 1 is part of a solid dispersion.

DETAILED DESCRIPTION

Figure 1:
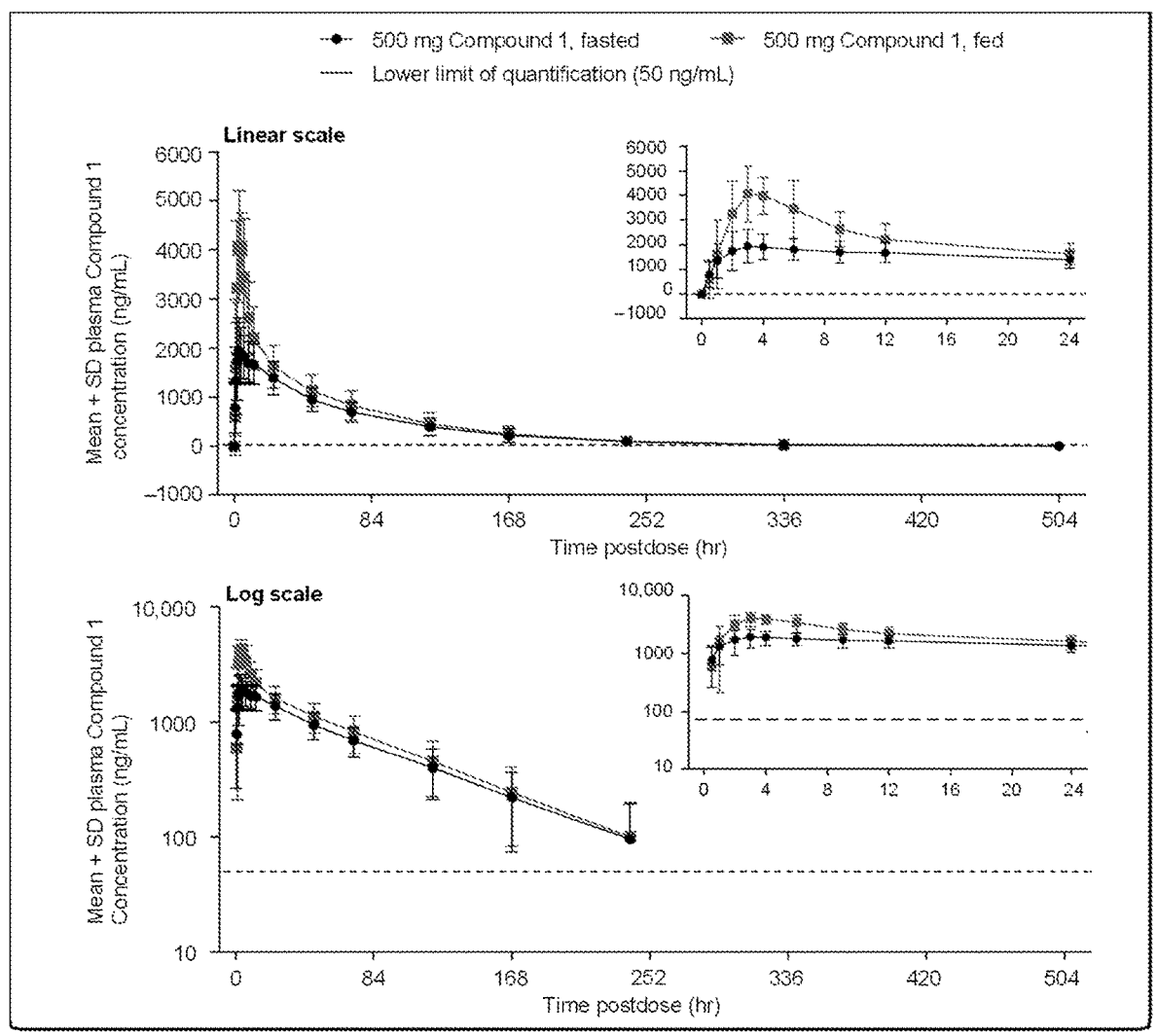
FIG. 1 depicts the mean (±SD) plasma concentrations of COMPOUND 1 over time following a single 500 mg oral dose under fasted and fed (high-fat meal) conditions.

The details of construction and the arrangement of components set forth in the following description or illustrated in the drawings are not meant to be limiting. Other embodiments and different ways to practice the invention are expressly included. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Definitions

The term a "mutant IDH1 inhibitor" or "inhibitor of IDH1 mutant(s)" means a molecule e.g., a polypeptide, peptide, or small molecule (e.g., a molecule of less than 1,000 daltons), or aptomer, that binds to an IDH1 mutant subunit and inhibits neoactivity, e.g., by inhibiting formation of a dimer, e.g., a homodimer of mutant IDH1 subunits or a heterodimer of a mutant and a wildtype subunit. In some embodiments, the neoactivity inhibition is at least about 60%, 70%, 80%, 90%, 95% or 99% as compared to the activity in the absence of the mutant IDH1 inhibitor. In one embodiment, the mutant IDH1 inhibitor is COMPOUND 1.

The term "elevated levels of 2HG" means 10%, 20% 30%, 50%, 75%, 100%, 200%, 500% or more 2HG is present in a subject that carries a mutant IDH1 allele than is present in a subject that does not carry a mutant IDH1 allele. The term "elevated levels of 2HG" may refer to the amount of 2HG within a cell, within a tumor, within an organ comprising a tumor, or within a bodily fluid.

The term "bodily fluid" includes one or more of amniotic fluid surrounding a fetus, aqueous humour, blood (e.g., blood plasma), serum, Cerebrospinal fluid, cerumen, chyme, Cowper's fluid, female ejaculate, interstitial fluid, lymph, breast milk, mucus (e.g., nasal drainage or phlegm), pleural fluid, pus, saliva, sebum, semen, serum, sweat, tears, urine, vaginal secretion, or vomit.

The terms "inhibit" or "prevent" include both complete and partial inhibition and prevention. An inhibitor may completely or partially inhibit the intended target.

The term "subject" is intended to include human and non-human animals. Exemplary human subjects include a human patient (referred to as a patient) having a disorder, e.g., a disorder described herein or a normal subject. The term "non-human animals" of one aspect of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

The term "treat" means decrease, suppress, attenuate, diminish, arrest, or stabilize the development or progression of a disease/disorder (e.g., an hematologic malignancy, including an advanced hematologic malignancy, such as acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma (e.g., T-cell lymphoma), or a solid tumor, including glioma, melanoma, chondrosarcoma, cholangiocarcinoma (including intrahepatic cholangiocarcinoma (IHCC), prostate cancer, colon cancer, or non-small cell lung cancer (NSCLC), each characterized by the presence of a mutant allele of IDH1), lessen the severity of the disease/disorder or improve the symptoms associated with the disease/disorder.

An amount of a compound, including a pharmaceutically acceptable salt, solvate, tautomer, stereoisomer, isotopologue, prodrug or a polymorph thereof, effective to treat a disorder, or a "therapeutically effective amount" or "therapeutically effective dose" refers to an amount of the compound, including a pharmaceutically acceptable salt, solvate, tautomer, stereoisomer, isotopologue, prodrug, or a polymorph thereof, which is effective, upon single or multiple dose administration to a subject, in treating a cell, or in curing, alleviating, relieving or improving a subject with a disorder beyond that expected in the absence of such treatment.

The term "co-administering" as used herein with respect to additional cancer therapeutic agents means that the additional cancer therapeutic agent may be administered together with a compound provided herein as part of a single dosage form (such as a composition comprising a compound and a second therapeutic agent as described above) or as separate, multiple dosage forms. Alternatively, the additional cancer therapeutic agent may be administered prior to, consecutively with, or following the administration of a compound provided herein. In such combination therapy treatment, both the compounds provided herein and the second therapeutic agent(s) are administered by conventional methods. The administration of a composition comprising both a compound provided herein and a second therapeutic agent, to a subject does not preclude the separate administration of that same therapeutic agent, any other second therapeutic agent or any compound provided herein to said subject at another time during a course of treatment. The term "co-administering" as used herein with respect to an additional cancer treatment means that the additional cancer treatment may occur prior to, consecutively with, concurrently with or following the administration of a compound provided herein.

The term "substantially free of other stereoisomers" as used herein means a preparation enriched in a compound having a selected stereochemistry at one or more selected stereocenters by at least about 60%, 65%, 70%, 75%, 80%, 85%, 90%, 95%, 96%, 97%, 98%, or 99%.

The term "enriched" means that at least the designated percentage of a preparation is the compound having a selected stereochemistry at one or more selected stereocenters.

The term "crystalline" refers to a solid having a highly regular chemical structure. In particular, a crystalline COMPOUND 1 may be produced as one or more single crystalline forms of COMPOUND 1. For the purposes of this application, the terms "crystalline form", "single crystalline form" and "polymorph" are synonymous; the terms distinguish between crystals that have different properties (e.g., different XRPD patterns and/or different DSC scan results). The term "polymorph" includes pseudopolymorphs, which are typically different solvates of a material, and thus their properties differ from one another. Thus, each distinct polymorph and pseudopolymorph of COMPOUND 1 is considered to be a distinct single crystalline form herein.

The term "substantially crystalline" refers to forms that may be at least a particular weight percent crystalline. Particular weight percentages are 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In some embodiments, substantially crystalline refers to a COMPOUND 1 that is at least 70% crystalline. In other embodiments, substantially crystalline refers to a COMPOUND 1 that is at least 90% crystalline.

The term "isolated" refers to forms that may be at least a particular weight percent of a particular crystalline form of a compound. Particular weight percentages are 90%, 91%, 92%, 93%, 94%, 95%, 96%, 97%, 98%, 99%, 99.5%, 99.9%, or any percentage between 90% and 100%.

The term "solvate or solvated" means a physical association of a compound, including a crystalline form thereof, of this invention with one or more solvent molecules. This physical association includes hydrogen bonding. In certain instances the solvate will be capable of isolation, for example when one or more solvent molecules are incorporated in the crystal lattice of the crystalline solid. "Solvate or solvated" encompasses both solution-phase and isolable solvates. Representative solvates include, for example, a hydrate, ethanolates or a methanolate.

The term "hydrate" is a solvate wherein the solvent molecule is $H_2O$ that is present in a defined stoichiometric amount, and may, for example, include hemihydrate, monohydrate, dihydrate, or trihydrate.

The term "mixture" is used to refer to the combined elements of the mixture regardless of the phase-state of the combination (e.g., liquid or liquid/crystalline).

The term "seeding" is used to refer to the addition of a crystalline material to initiate recrystallization or crystallization.

The term "antisolvent" is used to refer to a solvent in which compounds, including crystalline forms thereof, are poorly soluble.

The term "pharmaceutically acceptable carrier or adjuvant" refers to a carrier or adjuvant that may be administered to a subject, together with a compound of one aspect of this invention, and which does not destroy the pharmacological activity thereof and is nontoxic when administered in doses sufficient to deliver a therapeutic amount of the compound.

The term "a pharmaceutically-acceptable salt" as used herein refers to non-toxic acid or base addition salts of the compound to which the term refers. Examples of pharmaceutically acceptable salts are discussed in Berge et al., 1977, "Pharmaceutically Acceptable Salts." *J. Pharm. Sci.* Vol. 66, pp. 1-19.

The term "about" means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

The term "AUC" refers to the area under the time/plasma concentration curve after administration of the pharmaceutical composition. $AUC_{0-infinity}$ ($AUC_{0-\infty}$) denotes the area under the plasma concentration versus time curve from time 0 to infinity; $AUC_{0-t}$ denotes the area under the plasma concentration versus time curve from time 0 to time t. As used herein, $AUC_{0-t}$ is the area under the plasma concentration versus time curve from the time of dosing to the last quantifiable concentration. It should be appreciated that AUC values can be determined by known methods in the art.

The term "bioavailability" generally means the rate and extent to which the active ingredient, or active form thereof, is absorbed from a drug product and becomes available at the site of action. See U.S. Code of Federal Regulations, Title 21, Part 320.1 (2001 ed.). For oral dosage forms, bioavailability relates to the processes by which the active ingredient is released from the oral dosage form, e.g., a tablet, converted to the active form (if the active ingredient is not already the active form), and moved to the site of action, e.g., absorbed into the systemic circulation. For example, bioavailability is based on the area under the plasma concentration-time curves (e.g., $AUC_{0-t}$, $AUC_{0-\infty}$). To compare the bioavailability between different formulations comprising COMPOUND 1, the $AUC_{0-t}$ or $AUC_{0-\infty}$ values of each formulation would be compared (e.g., a comparison between a formulation of COMPOUND 1 in a tablet administered with a high-fat meal and a formulation of COMPOUND 1 in a tablet administered without food). It should be appreciated that AUC values may be compared as percent increase or percent decrease. It should further be appreciated that percent increase or percent decrease is calculated as known in the art.

The terms "without food" or "fasted" are defined to mean the condition of not having consumed food within a certain time period before and after the administration of COMPOUND 1 (e.g., 0.5-10 hours before and 0.5-10 hours after). For example, the time period can be 30 minutes, 60 minutes, 90 minutes, 2 hours, 3 hours, 4 hours, 5 hours, 6 hours, 7 hours, 8 hours, 9 hours or 10 hours before and 30 minutes, 60 minutes, 90 minutes, 2 hours, 3 hours, 4 hours, 5 hours, 6 hours, 7 hours, 8 hours, 9 hours or 10 hours after administration of COMPOUND 1.

As used herein, the term "unit dosage form" is defined to refer to the form in which COMPOUND 1 is administered to the subject. An "oral dosage form" represents one or more unit dosage forms that are orally administered to a subject. Specifically, the unit dosage form can be, for example, a pill, capsule, or tablet. Preferably, the unit dosage form is a tablet. The typical amount of COMPOUND 1 in an unit dosage form useful in the invention is about 50 mg to about 2000 mg, preferably about 100 mg to about 1000 mg, preferably about 200 mg to about 600 mg, preferably 250 to about 500 mg, preferably about 250 mg (e.g., 250 mg) or about 500 mg (e.g., 500 mg). In a preferred embodiment of the invention, the unit dosage form comprises about 500 mg, e.g., 500 mg, of COMPOUND 1 and is in the form of a tablet. In another preferred embodiment of the invention, the unit dosage form comprises about 250 mg, e.g., 250 mg, of COMPOUND 1 and is in the form of a tablet. Preferably, tablets which comprise about 500 mg, e.g., 500 mg, of COMPOUND 1, are administered to a subject once per day. In some embodiments, two tablets together comprise the 500 mg of COMPOUND 1. In some embodiments, one tablet comprises the 500 mg of COMPOUND 1. In some embodiments, four tablets together comprise 500 mg of COMPOUND 1. In some embodiments, five tablets together comprise 500 mg of COMPOUND 1.

As used herein, "with food", "substantially contemporaneously with food" or "substantially contemporaneous" means ingesting (or introducing) a substance containing food (e.g., high-fat meal, a standard meal or a regular meal, food comprising at least 50 calories, food comprising at least 100 calories, food comprising at least 200 calories, or food comprising at least 300 calories) within 5, 10, 15, 30, 45, 60, 75 or 90 minutes before or after ingesting a composition of the invention, e.g., an oral dosage form comprising COMPOUND 1.

The term "$C_{max}$" refers to the maximum concentration of a therapeutic agent (e.g., COMPOUND 1) in the blood (e.g., plasma) following administration of the pharmaceutical composition.

The term "$t_{max}$" refers to the time in hours when $C_{max}$ is achieved following administration of the pharmaceutical composition comprising the therapeutic agent (e.g., COMPOUND 1).

As used herein, "solid dosage form" means a pharmaceutical dose(s) in solid form, e.g., tablets, capsules, granules, powders, sachets, reconstitutable powders, dry powder inhalers and chewables.

As used herein, "high-fat meal" or means a high fat and high calorie meal with approximately 50 percent of total caloric content of the meal from fat and the meal being approximately 900 to 1000 calories. The meal may also be approximately 150, 250, and 500-600 calories from protein, carbohydrate, and fat, respectively. An exemplary high-fat meal includes the test meal disclosed in the document Guidance for Industry, Food-Effect Bioavailability and Fed Bioequivalence Studies, U.S. Department of Health and Human Services Food and Drug Administration, Center for Drug Evaluation and Research (CDER), Center for Biologics Evaluation and Research (CBER) issued December 2002. The exemplary high-fat meal contains approximately 50 percent of the total caloric content of the meal as fat and contains approximately 900 to 1000 calories; 500-600 calories from fat. As used herein, the term "fat" is used in its conventional, art-recognized meaning. In certain embodiments a "high-fat meal" means a meal that increases COMPOUND 1 $C_{max}$ by approximately 100% (e.g., by 98%) and/or COMPOUND 1 $AUC_{0-\infty}$ by approximately 25%.

As used herein, "regular meal" or "standard meal" means a meal being approximately 300 to 800 calories.

Compounds

COMPOUND 1 is (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide, a pharmaceutically acceptable salt, solvate, tautomer, stereoisomer, isotopologue, prodrug, or a polymorph thereof. In certain embodiments, COMPOUND 1 is (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide or a pharmaceutically acceptable salt thereof. In some embodiments, COMPOUND 1 is (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide. COMPOUND 1 has the following chemical structure:

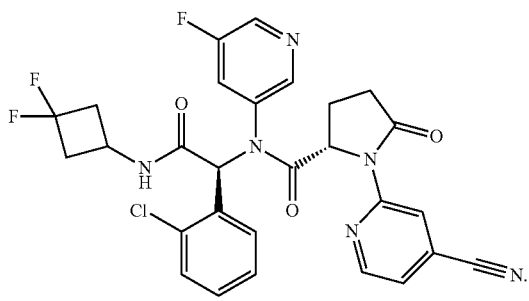 [SMILES: N#Cc1ccnc(N2C(=O)CC[C@H]2C(=O)N(c2cncc(F)c2)[C@H](C(=O)NC2CC(F)(F)C2)c2ccccc2Cl)c1]

COMPOUND 1 may also comprise one or more isotopic substitutions. For example, H may be in any isotopic form ("Isotopologues"), including $^1H$, $^2H$ (D or deuterium), and $^3H$ (T or tritium); C may be in any isotopic form, including $^{12}C$, $^{13}C$, and $^{14}C$; O may be in any isotopic form, including 16O and 18O; and the like. For example, COMPOUND 1 is enriched in a specific isotopic form of H, C and/or O by at least about 60%, 65%, 70%, 75%, 80%, 85%, 90%, 95%, 96%, 97%, 98%, or 99%.

COMPOUND 1 in certain embodiments may also be represented in multiple tautomeric forms, in such instances, one aspect of the invention expressly includes all tautomeric forms of COMPOUND 1 described herein, even though only a single tautomeric form may be represented (e.g., keto-enol tautomers). All such isomeric forms of COMPOUND 1 are expressly included herein. Synthesis of COMPOUND 1 is described in US published application US-2013-0190249-A1 published Jul. 25, 2013, which is incorporated by reference in its entirety.

It may be convenient or desirable to prepare, purify, and/or handle a corresponding salt of COMPOUND 1, for example, a pharmaceutically-acceptable salt. Examples of pharmaceutically acceptable salts are discussed in Berge et al., 1977, "Pharmaceutically Acceptable Salts." *J. Pharm. Sci*. Vol. 66, pp. 1-19.

For example, if COMPOUND 1 is anionic, or has a functional group which may be anionic (e.g., —NH— may be —N—), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If COMPOUND 1 is cationic, or has a functional group that may be cationic (e.g., —NHR may be —$NH_2R^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

COMPOUND 1 for use in the methods and pharmaceutical compositions provided herein therefore includes COMPOUND 1 itself, as well as its pharmaceutically acceptable salts, solvates, tautomers, stereoisomers, isotopologues, prodrugs or polymorphs. COMPOUND 1 provided herein may be modified and converted to a prodrug by appending appropriate functionalities to enhance selected biological properties, e.g., targeting to a particular tissue. Such modifications (i.e., prodrugs) are known in the art and include those which increase biological penetration into a given biological compartment (e.g., blood, lymphatic system, central nervous system), increase oral availability, increase solubility to allow administration by injection, alter metabolism and alter rate of excretion. Examples of prodrugs include esters (e.g., phosphates, amino acid (e.g., valine) esters), carbamates and other pharmaceutically acceptable derivatives, which, upon administration to a subject, are capable of providing active compounds.

It has been found that COMPOUND 1 can exist in a variety of solid forms. In one embodiment, provided herein are solid forms that include neat crystal forms. In another embodiment, provided herein are solid forms that include solvated forms and amorphous forms. The present disclosure provides certain solid forms of COMPOUND 1. In certain embodiments, the present disclosure provides compositions comprising COMPOUND 1 in a form described herein. In some embodiments of provided compositions, COMPOUND 1 is present as a mixture of one or more solid forms; in some embodiments of provided compositions, COMPOUND 1 is present in a single form.

In one embodiment, COMPOUND 1 is a single crystalline form, or any one of the single crystalline forms described herein. Synthesis of crystalline forms of COMPOUND 1 is described in international application publications WO 2015/138837 and WO 2015/138839, both published Sep. 17, 2015, both incorporated by reference herein in their entireties. Also provided are pharmaceutical compositions comprising at least one pharmaceutically acceptable carrier or diluent; and COMPOUND 1, wherein COMPOUND 1 is a single crystalline form, or any one of the crystalline forms being described herein. Also provided are uses of COMPOUND 1, wherein COMPOUND 1 is a single crystalline form, or any one of the single crystalline forms described herein, to prepare a pharmaceutical composition.

Provided herein is an assortment of characterizing information to describe the crystalline forms of COMPOUND 1. It should be understood, however, that not all such information is required for one skilled in the art to determine that such particular form is present in a given composition, but that the determination of a particular form can be achieved using any portion of the characterizing information that one skilled in the art would recognize as sufficient for establishing the presence of a particular form, e.g., even a single distinguishing peak can be sufficient for one skilled in the art to appreciate that such particular form is present.

In one embodiment, at least a particular percentage by weight of COMPOUND 1 is crystalline. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. When a particular percentage by weight of COMPOUND 1 is crystalline, the remainder of COMPOUND 1 is the amorphous form of COMPOUND 1. Non-limiting examples of crystalline COMPOUND 1 include a single crystalline form of COMPOUND 1 or a mixture of different single crystalline forms. In some embodiments, COMPOUND 1 is at least 90% by weight crystalline. In some other embodiments, COMPOUND 1 is at least 95% by weight crystalline.

In another embodiment, a particular percentage by weight of the crystalline COMPOUND 1 is a specific single crystalline form or a combination of single crystalline forms. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In another embodiment, COMPOUND 1 is at least 90% by weight of a single crystalline form. In another embodiment, COMPOUND 1 is at least 95% by weight of a single crystalline form.

In the following description of COMPOUND 1, embodiments of the invention may be described with reference to a particular crystalline form of COMPOUND 1, as characterized by one or more properties as discussed herein. The descriptions characterizing the crystalline forms may also be used to describe the mixture of different crystalline forms that may be present in a crystalline COMPOUND 1. However, the particular crystalline forms of COMPOUND 1 may also be characterized by one or more of the characteristics of the crystalline form as described herein, with or without regard to referencing a particular crystalline form.

The crystalline forms are further illustrated by the detailed descriptions and illustrative examples given below. The XRPD peaks described in Tables 1 to 2 may vary by ±0.2° depending upon the instrument used to obtain the data. The intensity of the XRPD peaks described in Tables 1 to 2 may vary by 10%.

Form 1

Figure 2:
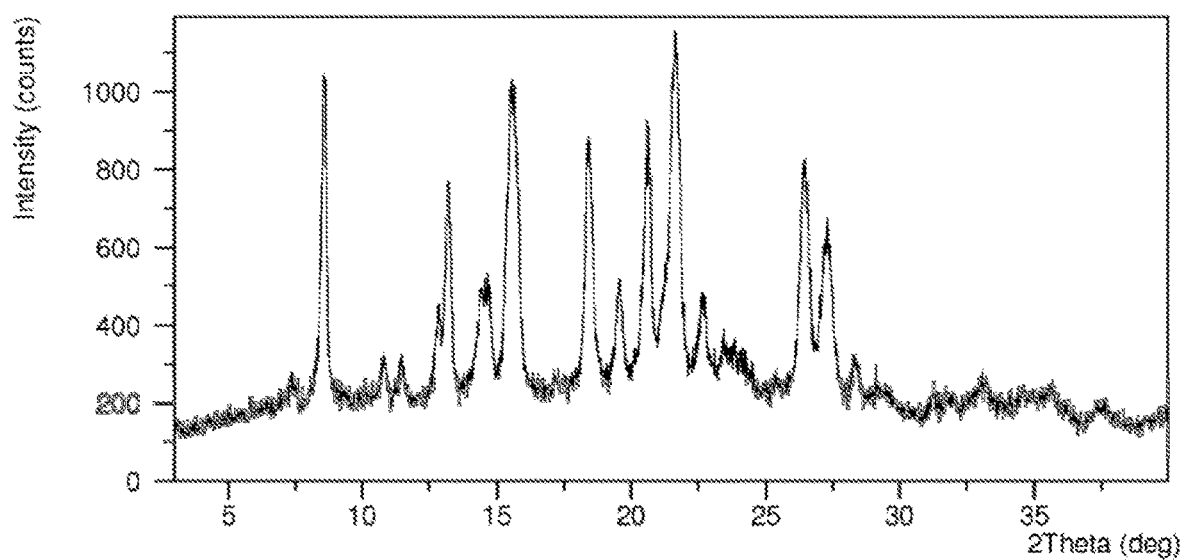
FIG. 2 is an X-ray powder diffractogram (XPRD) of COMPOUND 1 form 1.

In one embodiment, a single crystalline form, Form 1, of COMPOUND 1 is characterized by the X-ray powder diffraction (XRPD) pattern shown in FIG. 2, and data shown in Table 1, obtained using CuKa radiation. In a particular embodiment, the polymorph can be characterized by one or more of the peaks taken from FIG. 2, as shown in Table 1. For example, the polymorph can be characterized by one or two or three or four or five or six or seven or eight or nine of the peaks shown in Table 1.

TABLE 1

| Angle 2-Theta° | Intensity % |
| --- | --- |
| 8.6 | 90.3 |
| 13.2 | 60.0 |
| 15.6 | 85.5 |
| 18.5 | 72.5 |
| 19.6 | 31.5 |
| 20.6 | 71.6 |
| 21.6 | 100.0 |
| 26.4 | 64.2 |
| 27.3 | 45.6 |

In another embodiment, Form 1 can be characterized by the peaks identified at 2θ angles of 8.6, 15.6, 18.5, 20.6, 21.6, and 26.4°. In another embodiment, Form 1 can be characterized by the peaks identified at 2θ angles of 8.6, 15.6, 18.5, and 21.6°.

Figure 3:
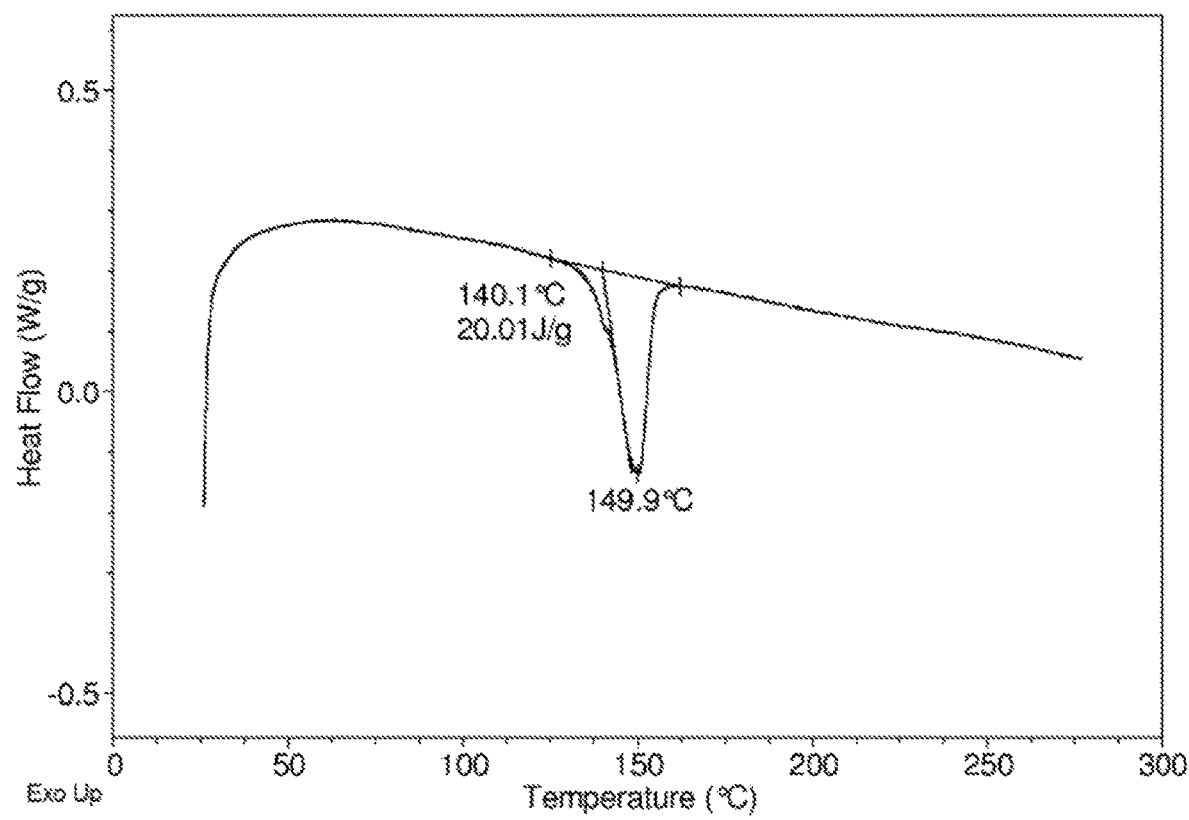
FIG. 3 is a differential scanning calorimetry (DSC) profile of COMPOUND 1 form 1.

In another embodiment, Form 1 can be characterized by the differential scanning calorimetry profile (DSC) shown in FIG. 3. The DSC graph plots the heat flow as a function of temperature from a sample, the temperature rate change being about 10° C./min. The profile is characterized by an endothermic transition with an onset temperature of about 140.1° C. with a melt at about 149.9° C.

Figure 4:
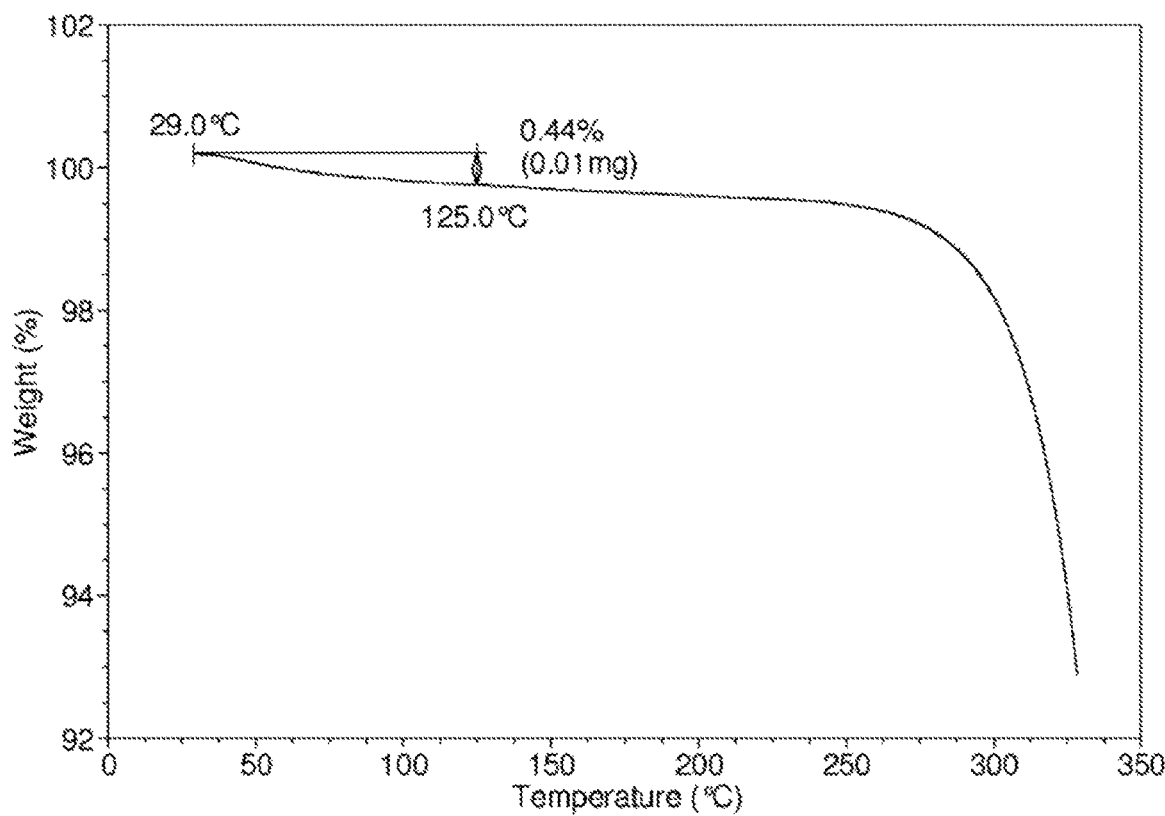
FIG. 4 is a thermal gravimetric analysis (TGA) profile of COMPOUND 1 form 1.

In another embodiment, Form 1 can be characterized by thermal gravimetric analysis (TGA) shown in FIG. 4. The TGA profile graphs the percent loss of weight of the sample as a function of temperature, the temperature rate change being about 10° C./min. The weight loss represents a loss of about 0.44% of the weight of the sample as the temperature is changed from about 29.0° C. to 125.0° C.

Form 2

Figure 5:
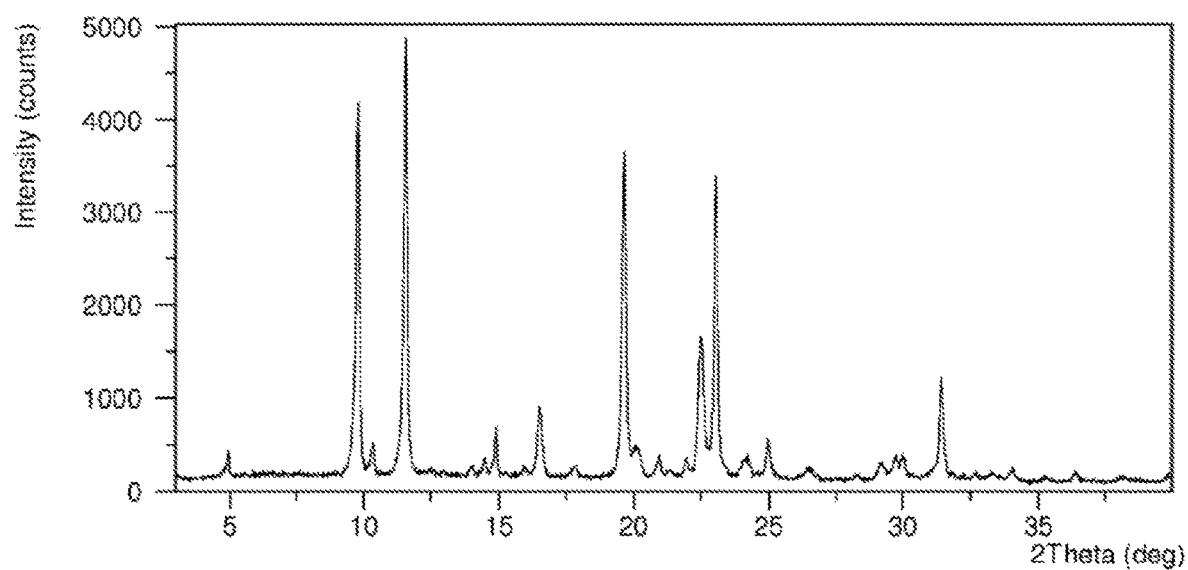
FIG. 5 is an X-ray powder diffractogram (XPRD) of COMPOUND 1 form 2.

In one embodiment, a single crystalline form, Form 2, of the COMPOUND 1 is characterized by the X-ray powder diffraction (XRPD) pattern shown in FIG. 5, and data shown in Table 2, obtained using CuKa radiation. In a particular embodiment, the polymorph can be characterized by one or more of the peaks taken from FIG. 5, as shown in Table 2. For example, the polymorph can be characterized by one or two or three or four or five or six or seven or eight or nine or ten of the peaks shown in Table 2.

TABLE 2

| Angle 2-Theta° | Intensity % |
|---|---|
| 9.8 | 85.6 |
| 11.6 | 100.0 |
| 14.9 | 11.4 |
| 16.5 | 15.3 |
| 19.6 | 75.2 |
| 20.1 | 7.3 |
| 22.5 | 32.6 |
| 23.0 | 69.4 |
| 25.0 | 8.9 |
| 31.4 | 22.0 |

In another embodiment, Form 2 can be characterized by the peaks identified at 2θ angles of 9.8, 11.6, 19.6, 22.5, 23.0, and 31.4°. In another embodiment, Form 2 can be characterized by the peaks identified at 2θ angles of 9.8, 11.6, 19.6, and 23.0°.

Figure 6:
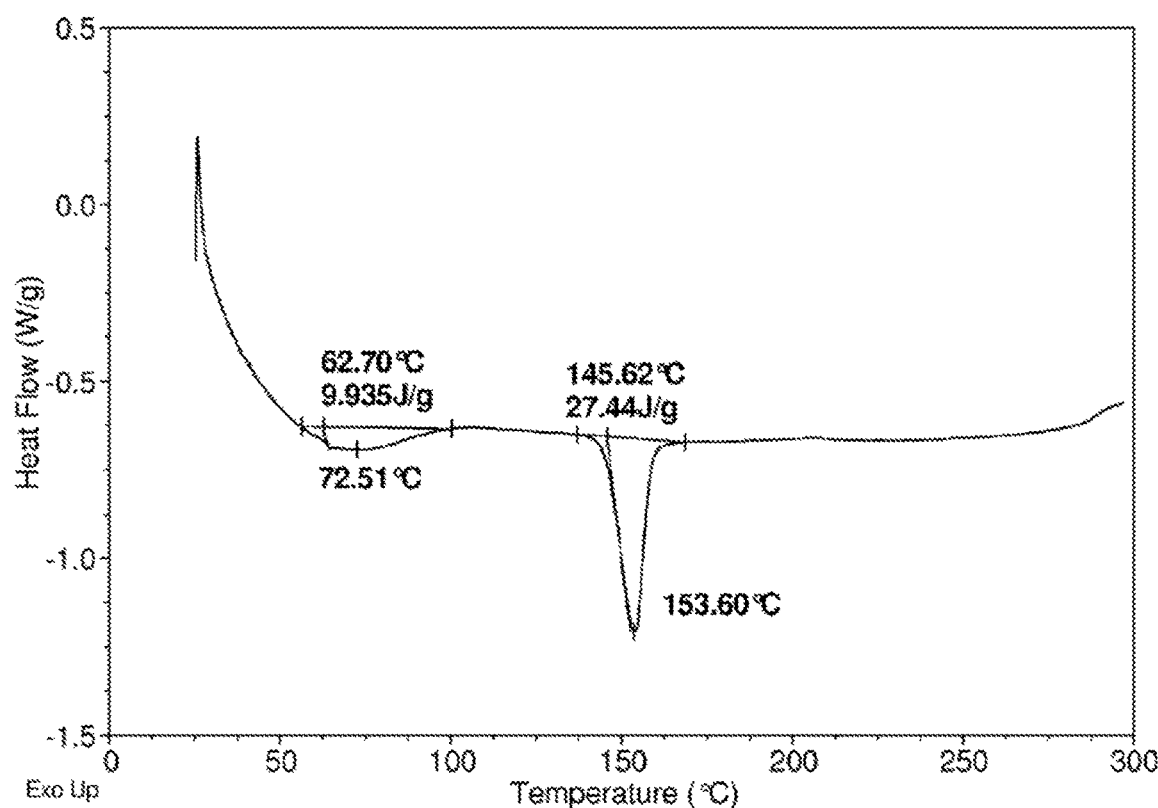
FIG. 6 is a differential scanning calorimetry (DSC) profile of COMPOUND 1 form 2.

In another embodiment, Form 2 can be characterized by the differential scanning calorimetry profile (DSC) shown in FIG. 6. The DSC graph plots the heat flow as a function of temperature from a sample, the temperature rate change being about 10° C./min. The profile is characterized by an endothermic transition with an onset temperature of about 62.7° C. with a melt at about 72.5° C., and an endothermic transition with an onset temperature of about 145.6° C. with a melt at about 153.6° C.

Figure 7:
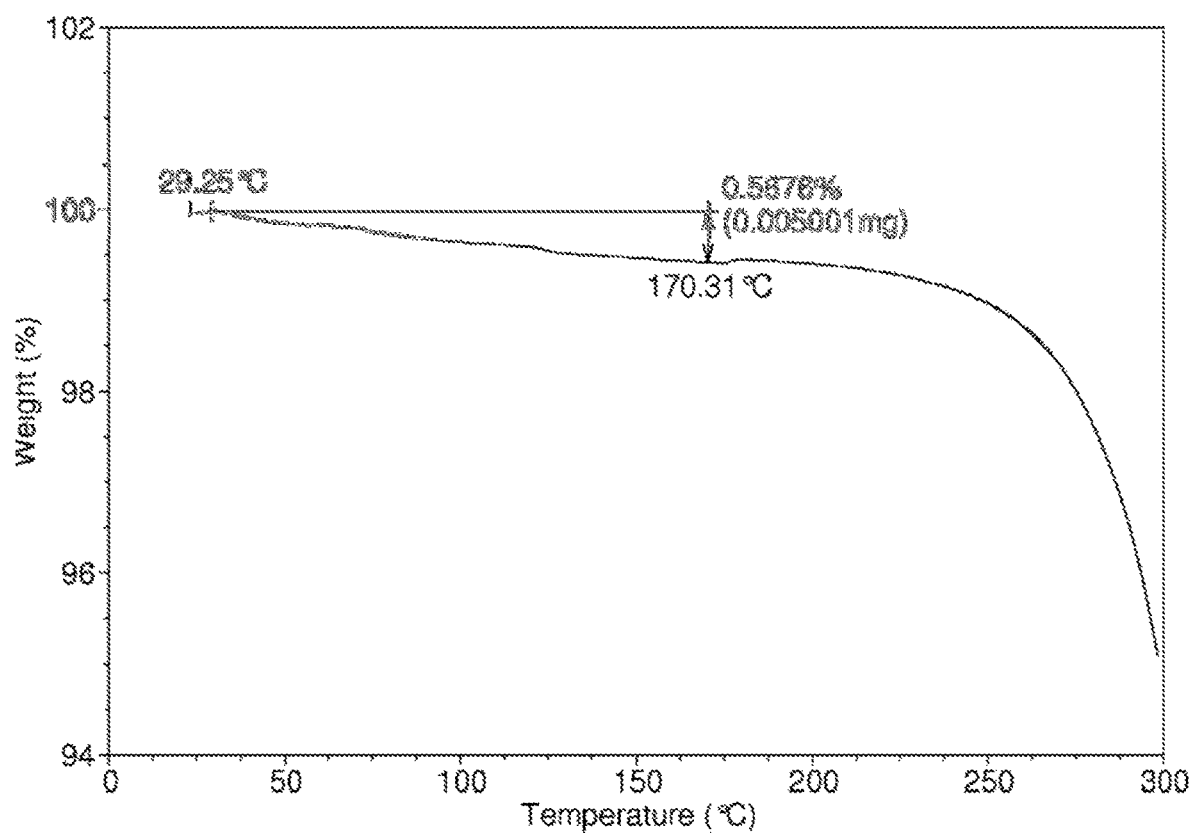
FIG. 7 is a thermal gravimetric analysis (TGA) profile of COMPOUND 1 form 2.

In another embodiment, Form 2 can be characterized by thermal gravimetric analysis (TGA) shown in FIG. 7. The TGA profile graphs the percent loss of weight of the sample as a function of temperature, the temperature rate change being about 10° C./min. The weight loss represents a loss of about 0.57% of the weight of the sample as the temperature is changed from about 29.3° C. to 170.3° C.

Other embodiments are directed to a single crystalline form of COMPOUND 1 characterized by a combination of the aforementioned characteristics of any of the single crystalline forms discussed herein. The characterization may be by any combination of one or more of the XRPD, TGA, and DSC described for a particular polymorph. For example, the single crystalline form of COMPOUND 1 may be characterized by any combination of the XRPD results regarding the position of the major peaks in a XRPD scan; and/or any combination of one or more of parameters derived from data obtained from a XRPD scan. The single crystalline form of COMPOUND 1 may also be characterized by TGA determinations of the weight loss associated with a sample over a designated temperature range; and/or the temperature at which a particular weight loss transition begins. DSC determinations of the temperature associated with the maximum heat flow during a heat flow transition and/or the temperature at which a sample begins to undergo a heat flow transition may also characterize the crystalline form. Weight change in a sample and/or change in sorption/desorption of water per molecule of COMPOUND 1 as determined by water sorption/desorption measurements over a range of relative humidity (e.g., 0% to 90%) may also characterize a single crystalline form of COMPOUND 1.

Compositions and Routes of Administration

In one embodiment, provided herein is a pharmaceutical composition comprising a therapeutically effective amount of a mutant IDH1 inhibitor. In one embodiment, the mutant IDH1 inhibitor is COMPOUND 1.

In one embodiment, the compounds utilized in the methods provided herein may be formulated together with a pharmaceutically acceptable carrier or adjuvant into pharmaceutically acceptable compositions prior to be administered to a subject. In another embodiment, such pharmaceutically acceptable compositions further comprise additional therapeutic agents in amounts effective for achieving a modulation of disease or disease symptoms, including those described herein.

Pharmaceutically acceptable carriers, adjuvants and vehicles that may be used in the pharmaceutical compositions of one aspect of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of COMPOUND 1 described herein.

In one embodiment, the pharmaceutical composition comprises COMPOUND 1 and an excipient. In one embodiment, the pharmaceutical composition that comprises COMPOUND 1 and an excipient is for oral administration. In one embodiment, the excipient is a diluent, a binder, a disintegrant, a wetting agent, a stabilizer, a glidant, or a lubricant.

Oral delivery formats for COMPOUND 1 include, but are not limited to, tablets, capsules, caplets, solutions, suspensions, and syrups, and may also comprise a plurality of granules, beads, powders or pellets that may or may not be encapsulated. Such formats may also be referred to herein as the "drug core" which contains COMPOUND 1.

Particular embodiments herein provide solid oral dosage forms that are tablets or capsules. In certain embodiments, the formulation is a tablet comprising COMPOUND. In certain embodiments, the formulation is a capsule comprising COMPOUND 1. In certain embodiments, the tablets or capsules provided herein optionally comprise one or more excipients, such as, for example, glidants, diluents, lubricants, colorants, disintegrants, granulating agents, binding agents, polymers, and coating agents. In certain embodiments, the formulation is an immediate release tablet. In certain embodiments, the formulation is a controlled release tablet releasing the active pharmaceutical ingredient (API), e.g., substantially in the stomach. In certain embodiments, the formulation is a hard gelatin capsule. In certain embodiments, the formulation is a soft gelatin capsule. In certain embodiments, the capsule is a hydroxypropyl methylcellulose (HPMC) capsule. In certain embodiments, the formulation is an immediate release capsule. In certain embodiments, the formulation is an immediate or controlled release capsule releasing the API, e.g., substantially in the stomach. In certain embodiments, the formulation is a rapidly disintegrating tablet that dissolves substantially in the mouth following administration. In certain embodiments, embodiments herein encompass the use of COMPOUND 1 for the preparation of a pharmaceutical composition for treating a malignancy, characterized by the presence of a mutant allele of IDH1, wherein the composition is prepared for oral administration.

Particular embodiments herein provide pharmaceutical formulations (e.g., oral dosage forms, immediate release oral formulations and/or formulations that release the API substantially in the stomach, e.g., oral dosage forms) comprising COMPOUND 1 that achieve a particular AUC value (e.g., $AUC_{0-t}$ or $AUC_{0-\infty}$) in the subject (e.g., human) to which the formulation is orally administered. Particular embodiments provide oral formulations that achieve an AUC value of at least about 25 ng-hr/mL, at least about 50 ng-hr/mL, at least about 75 ng-hr/mL, at least about 100 ng-hr/mL, at least about 150 ng-hr/mL, at least about 200 ng-hr/mL, at least about 250 ng-hr/mL, at least about 300 ng-hr/mL, at least about 350 ng-hr/mL, at least about 400 ng-hr/mL, at least about 450 ng-hr/mL, at least about 500 ng-hr/mL, at least about 550 ng-hr/mL, at least about 600 ng-hr/mL, at least about 650 ng-hr/mL, at least about 700 ng-hr/mL, at least about 750 ng-hr/mL, at least about 800 ng-hr/mL, at least about 850 ng-hr/mL, at least about 900 ng-hr/mL, at least about 950 ng-hr/mL, at least about 1000 ng-hr/mL, at least about 1100 ng-hr/mL, at least about 1200 ng-hr/mL, at least about 1300 ng-hr/mL, at least about 1400 ng-hr/mL, at least about 1500 ng-hr/mL, at least about 1600 ng-hr/mL, at least about 1700 ng-hr/mL, at least about 1800 ng-hr/mL, at least about 1900 ng-hr/mL, at least about 2000 ng-hr/mL, at least about 2250 ng-hr/mL, at least about 2500 ng-hr/mL, at least about 5000 ng-hr/mL, at least about 10000 ng-hr/mL, at least about 20000 ng-hr/mL, at least about 30000 ng-hr/mL, at least about 40000 ng-hr/mL, at least about 50000 ng-hr/mL, at least about 60000 ng-hr/mL, at least about 70000 ng-hr/mL, at least about 80000 ng-hr/mL, at least about 90000 ng-hr/mL, at least about 100000 ng-hr/mL, at least about 110000 ng-hr/mL, at least about 120000 ng-hr/mL, or at least about 130000 ng-hr/mL. In a preferred embodiment, provided is a pharmaceutical formulation (e.g., an immediate release oral formulation, e.g., an oral dosage form) that achieves an AUC value (e.g., $AUC_{0-t}$ or $AUC_{0-\infty}$) between 110000 hr-ng/mL and 165000 hr-ng/mL, preferably between 120000 hr-ng/mL and 155000 hr-ng/mL in the subject to which the formulation is orally administered. In an embodiment the AUC value is obtained when the pharmaceutical formulation is administered to a subject with or without food, avoiding administration with a high-fat meal. In one embodiment, provided is a pharmaceutical formulation (e.g., an immediate release oral formulation, e.g., an oral dosage form) comprising 500 mg COMPOUND 1 that achieves an AUC value (e.g., $AUC_{0-t}$ or $AUC_{0-\infty}$) between 110000 hr-ng/mL and 165000 hr-ng/mL, preferably between 120000 hr-ng/mL and 155000 hr-ng/mL in the subject to which the formulation is orally administered. In an embodiment the AUC value is obtained when the pharmaceutical formulation is administered to a subject with or without food, avoiding administration with a high-fat meal. In an embodiment the formulation is provided in a single unit dosage form (e.g., tablet, capsule) comprising 500 mg COMPOUND 1. In an embodiment the formulation is provided in 2 unit dosage forms (e.g., tablets, capsules) comprising 250 mg COMPOUND 1 each. In another embodiment the formulation is provided in 4 unit dosage forms (e.g., tablets, capsules) comprising 125 mg COMPOUND 1 each. In another embodiment the formulation is provided in 5 unit dosage forms (e.g., tablets, capsules) comprising 100 mg COMPOUND 1 each.

In particular embodiments, the AUC determination is obtained from a time-concentration pharmacokinetic profile obtained from the blood samples of animals or human volunteers following dosing.

Particular embodiments herein provide pharmaceutical formulations (e.g., immediate release oral formulations and/or formulations that release the API substantially in the stomach, e.g., oral dosage forms) comprising COMPOUND 1 that achieve a particular maximum plasma concentration ("$C_{max}$") in the subject to which the formulation is orally administered. Particular embodiments provide oral formulations that achieve a $C_{max}$ of the COMPOUND 1 of at least about 25 ng/mL, at least about 50 ng/mL, at least about 75 ng/mL, at least about 100 ng/mL, at least about 150 ng/mL, at least about 200 ng/mL, at least about 250 ng/mL, at least about 300 ng/mL, at least about 350 ng/mL, at least about 400 ng/mL, at least about 450 ng/mL, at least about 500 ng/mL, at least about 550 ng/mL, at least about 600 ng/mL, at least about 650 ng/mL, at least about 700 ng/mL, at least about 750 ng/mL, at least about 800 ng/mL, at least about 850 ng/mL, at least about 900 ng/mL, at least about 950 ng/mL, at least about 1000 ng/mL, at least about 1100 ng/mL, at least about 1200 ng/mL, at least about 1300 ng/mL, at least about 1400 ng/mL, at least about 1500 ng/mL, at least about 1600 ng/mL, at least about 1700 ng/mL, at least about 1800 ng/mL, at least about 1900 ng/mL, at least about 2000 ng/mL, at least about 2250 ng/mL, or at least about 2500 ng/mL. Particular embodiments provide oral formulations that achieve a $C_{max}$ of the COMPOUND 1 of no more than 6000 ng/mL, no more than 5500 ng/mL, no more than 5000 ng/mL, no more than 4500 ng/mL, no more than 4000 ng/mL, no more than 3500 ng/mL, no more than 3000 ng/mL, no more than 2500 ng/mL, no more than 2000 ng/mL or no more than 1500 ng/mL. In a preferred embodiment provided is a pharmaceutical formulation (e.g., an immediate release oral formulation, e.g., an oral dosage form) that achieves a $C_{max}$ of COMPOUND 1 between 1500 ng/mL and 3100 ng/mL, preferably between 1800 ng/mL and 2800 ng/mL in the subject to which the formulation is orally administered. In an embodiment the AUC value is obtained when the pharmaceutical formulation is administered to a subject with or without food, avoiding administration with a high-fat meal. In one embodiment, provided is a pharmaceutical formulation (e.g., an immediate release oral formulation, e.g., an oral dosage form) comprising 500 mg COMPOUND 1 that achieves a $C_{max}$ of COMPOUND 1 between 1500 ng/mL and 3100 ng/mL, preferably between 1800 ng/mL and 2800 ng/mL in the subject to which the formulation is orally administered. In an embodiment the AUC value is obtained when the pharmaceutical formulation is administered to a subject with or without food, avoiding administration with a high-fat meal. In an embodiment the formulation is provided in a single unit dosage form (e.g., tablet, capsule) comprising 500 mg COMPOUND 1. In an embodiment the formulation is provided in 2 unit dosage forms (e.g., tablets, capsules) comprising 250 mg COMPOUND 1 each. In another embodiment the formulation is provided in 4 unit dosage forms (e.g., tablets, capsules) comprising 125 mg COMPOUND 1 each. In another embodiment the formulation is provided in 5 unit dosage forms (e.g., tablets, capsules) comprising 100 mg COMPOUND 1 each.

Particular embodiments herein provide pharmaceutical formulations (e.g., immediate release oral formulations and/or formulations that release the API substantially in the stomach) comprising COMPOUND 1 that achieve a particular time to maximum plasma concentration ("Tmax") in the subject to which the formulation is orally administered. Particular embodiments provide oral formulations that achieve a Tmax of COMPOUND 1 of less than about 10 min., less than about 15 min., less than about 20 min., less than about 25 min., less than about 30 min., less than about 35 min., less than about 40 min., less than about 45 min., less than about 50 min., less than about 55 min., less than about 60 min., less than about 65 min., less than about 70 min., less than about 75 min., less than about 80 min., less than about 85 min., less than about 90 min., less than about 95 min., less than about 100 min., less than about 105 min., less than about 110 min., less than about 115 min., less than about 120 min., less than about 130 min., less than about 140 min., less than about 150 min., less than about 160 min., less than about 170 min., less than about 180 min., less than about 190 min., less than about 200 min., less than about 210 min., less than about 220 min., less than about 230 min., or less than about 240 min. In particular embodiments, the Tmax value is measured from the time at which the formulation is orally administered.

Particular embodiments herein provide oral dosage forms comprising COMPOUND 1 wherein the oral dosage forms have an enteric coating. Particular embodiments provide a permeable or partly permeable (e.g., "leaky") enteric coating with pores. In particular embodiments, the permeable or partly permeable enteric-coated tablet releases the COMPOUND 1 in an immediate release manner substantially in the stomach.

Provided herein are dosage forms designed to maximize the absorption and/or efficacious delivery of COMPOUND 1, upon oral administration, e.g., for release substantially in the stomach. Accordingly, certain embodiments herein provide a solid oral dosage form of COMPOUND 1 using pharmaceutical excipients designed for immediate release of the API upon oral administration, e.g., substantially in the stomach. Particular immediate release formulations comprise a specific amount of COMPOUND and optionally one or more excipients. In certain embodiments, the formulation may be an immediate release tablet or an immediate release capsule (such as, e.g., an HPMC capsule).

Provided herein are methods of making the formulations provided herein comprising COMPOUND 1 provided herein (e.g., immediate release oral formulations and/or formulations that release the API substantially in the stomach). In particular embodiments, the formulations provided herein may be prepared using conventional methods known to those skilled in the field of pharmaceutical formulation, as described, e.g., in pertinent textbooks. See, e.g., REMINGTON, THE SCIENCE AND PRACTICE OF PHARMACY, 20th Edition, Lippincott Williams & Wilkins, (2000); ANSEL et al., PHARMACEUTICAL DOSAGE FORMS AND DRUG DELIVERY SYSTEMS, 7th Edition, Lippincott Williams & Wilkins, (1999); GIBSON, PHARMACEUTICAL PREFORMULATION AND FORMULATION, CRC Press (2001).

In particular embodiments, formulations provided herein (e.g., oral dosage forms, immediate release oral formulations, formulations that release the API substantially in the stomach, or rapidly disintegrating formulations that dissolve substantially in the mouth) comprise COMPOUND 1 in a specific amount. In particular embodiments, the specific amount of COMPOUND 1 in the formulation is, e.g., about 10 mg. In one embodiment, the specific amount is about 20 mg. In one embodiment, the specific amount is about 40 mg. In one embodiment, the specific amount is about 60 mg. In one embodiment, the specific amount is about 80 mg. In one embodiment, the specific amount is about 100 mg. In one embodiment, the specific amount is about 120 mg. In one embodiment the specific amount is about 125 mg. In one embodiment, the specific amount is about 140 mg. In one embodiment, the specific amount is about 160 mg. In one embodiment, the specific amount is about 180 mg. In one embodiment, the specific amount is about 200 mg. In one embodiment, the specific amount is about 220 mg. In one embodiment, the specific amount is about 240 mg. In one embodiment, the specific amount is about 260 mg. In one embodiment the specific amount is about 250 mg. In one embodiment, the specific amount is about 280 mg. In one embodiment, the specific amount is about 300 mg. In one embodiment, the specific amount is about 320 mg. In one embodiment, the specific amount is about 340 mg. In one embodiment, the specific amount is about 360 mg. In one embodiment, the specific amount is about 380 mg. In one embodiment, the specific amount is about 400 mg. In one embodiment, the specific amount is about 420 mg. In one embodiment, the specific amount is about 440 mg. In one embodiment, the specific amount is about 460 mg. In one embodiment, the specific amount is about 480 mg. In one embodiment, the specific amount is about 500 mg. In one embodiment, the specific amount is about 600 mg. In one embodiment, the specific amount is about 700 mg. In one embodiment, the specific amount is about 800 mg. In one embodiment, the specific amount is about 900 mg. In one embodiment, the specific amount is about 1000 mg. In one embodiment, the specific amount is about 1100 mg. In one embodiment, the specific amount is about 1200 mg. In one embodiment, the specific amount is about 1300 mg. In one embodiment, the specific amount is about 1400 mg. In one embodiment, the specific amount is about 1500 mg. In one embodiment, the specific amount is about 1600 mg. In one embodiment, the specific amount is about 1700 mg. In one embodiment, the specific amount is about 1800 mg. In one embodiment, the specific amount is about 1900 mg. In one embodiment, the specific amount is about 2000 mg. In one embodiment, the specific amount is about 2100 mg. In one embodiment, the specific amount is about 2200 mg. In one embodiment, the specific amount is about 2300 mg. In one embodiment, the specific amount is about 2400 mg. In one embodiment, the specific amount is about 2500 mg. In one embodiment, the specific amount is about 3000 mg. In one embodiment, the specific amount is about 4000 mg. In one embodiment, the specific amount is about 5000 mg.

In certain embodiments, the formulation is a tablet, wherein the tablet is manufactured using standard, art-recognized tablet processing procedures and equipment. In certain embodiments, the method for forming the tablets is direct compression of a powdered, crystalline and/or granular composition comprising COMPOUND 1 alone or in combination with one or more excipients, such as, for example, carriers, additives, polymers, or the like. In certain embodiments, as an alternative to direct compression, the tablets may be prepared using wet granulation or dry granulation processes. In certain embodiments, the tablets are molded rather than compressed, starting with a moist or otherwise tractable material. In certain embodiments, compression and granulation techniques are used.

In certain embodiments, the formulation is a capsule, wherein the capsules may be manufactured using standard, art-recognized capsule processing procedures and equipments. In certain embodiments, soft gelatin capsules may be prepared in which the capsules contain a mixture of COMPOUND 1 and vegetable oil or non-aqueous, water miscible materials such as, for example, polyethylene glycol and the like. In certain embodiments, hard gelatin capsules may be prepared containing granules of COMPOUND 1 in combination with a solid pulverulent carrier, such as, for example, lactose, saccharose, sorbitol, mannitol, potato starch, corn starch, amylopectin, cellulose derivatives, or gelatin. In certain embodiments, a hard gelatin capsule shell may be prepared from a capsule composition comprising gelatin and a small amount of plasticizer such as glycerol. In certain embodiments, as an alternative to gelatin, the capsule shell may be made of a carbohydrate material. In certain embodiments, the capsule composition may additionally include polymers, colorings, flavorings and opacifiers as required. In certain embodiments, the capsule comprises HPMC.

In certain embodiments, the formulation of COMPOUND 1 is prepared using aqueous solvents without causing significant hydrolytic degradation of the compound. In particular embodiments, the formulation of COMPOUND 1 is a tablet which contains a coating applied to the drug core using aqueous solvents. In certain embodiments, water is employed as the solvent for coating the drug core. In certain embodiments, the oral dosage form of COMPOUND 1 is a tablet containing a film coat applied to the drug core using aqueous solvents. In particular embodiments, water is employed as the solvent for film-coating. In particular embodiments, the tablet containing COMPOUND 1 is film-coated using aqueous solvents without effecting degradation of the pharmaceutical composition. In particular embodiments, water is used as the film coating solvent without effecting degradation of the pharmaceutical composition. In certain embodiments, an oral dosage form comprising COMPOUND 1 and an aqueous film coating effects immediate drug release upon oral delivery. In certain embodiments, the oral dosage form comprising COMPOUND 1 and an aqueous film coating effects controlled drug release to the upper gastrointestinal tract, e.g., the stomach, upon oral administration. In particular embodiments, a tablet with an aqueous-based film coating comprises COMPOUND 1 as the API.

In certain embodiments, provided herein is a controlled release pharmaceutical formulation for oral administration that releases COMPOUND 1 substantially in the stomach, comprising: a) a specific amount of COMPOUND 1; b) a drug release controlling component for controlling the release of COMPOUND 1 substantially in the upper gastrointestinal tract, e.g., the stomach; and c) optionally one or more excipients. In certain embodiments, the oral dosage form comprising COMPOUND 1 is prepared as a controlled release tablet or capsule which includes a drug core comprising the pharmaceutical composition and optional excipients. Optionally, a "seal coat" or "shell" is applied. In certain embodiments, a formulation provided herein comprising COMPOUND 1 provided herein is a controlled release tablet or capsule, which comprises a therapeutically effective amount of COMPOUND 1, a drug release controlling component that controls the release of COMPOUND 1 substantially in the stomach upon oral administration, and optionally, one or more excipients.

Particular embodiments provide a drug release controlling component that is a polymer matrix, which swells upon exposure to gastric fluid to effect the gastric retention of the formulation and the sustained release of COMPOUND 1 from the polymer matrix substantially in the stomach. In certain embodiments, such formulations may be prepared by incorporating COMPOUND 1 into a suitable polymeric matrix during formulation. Examples of such formulations are known in the art. See, e.g., Shell et al., U.S. Patent Publication No. 2002/0051820 (application Ser. No. 09/990, 061); Shell et al., U.S. Patent Publication No. 2003/0039688 (application Ser. No. 10/045,823); Gusler et al., U.S. Patent Publication No. 2003/0104053 (application Ser. No. 10/029, 134), each of which is incorporated herein by reference in its entirety.

In certain embodiments, the drug release controlling component may comprise a shell surrounding the drug-containing core, wherein the shell releases COMPOUND 1 from the core by, e.g., permitting diffusion of COMPOUND 1 from the core and promoting gastric retention of the formulation by swelling upon exposure to gastric fluids to a size that is retained in the stomach. In certain embodiments, such formulations may be prepared by first compressing a mixture of COMPOUND 1 and one or more excipients to form a drug core, and compressing another powdered mixture over the drug core to form the shell, or enclosing the drug core with a capsule shell made of suitable materials. Examples of such formulations are known in the art. See, e.g., Berner et al., U.S. Patent Publication No. 2003/0104062 application Ser. No. 10/213,823), incorporated herein by reference in its entirety.

In certain embodiments, the pharmaceutical formulations provided herein contain COMPOUND 1 and, optionally, one or more excipients to form a "drug core." Optional excipients include, e.g., diluents (bulking agents), lubricants, disintegrants, fillers, stabilizers, surfactants, preservatives, coloring agents, flavoring agents, binding agents, excipient supports, glidants, permeation enhancement excipients, plasticizers and the like, e.g., as known in the art. It will be understood by those in the art that some substances serve more than one purpose in a pharmaceutical composition. For instance, some substances are binders that help hold a tablet together after compression, yet are also disintegrants that help break the tablet apart once it reaches the target delivery site. Selection of excipients and amounts to use may be readily determined by the formulation scientist based upon experience and consideration of standard procedures and reference works available in the art.

In certain embodiments, formulations provided herein comprise one or more binders. Binders may be used, e.g., to impart cohesive qualities to a tablet, and thus ensure that the tablet remains intact after compression. Suitable binders include, but are not limited to, starch (including corn starch and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone, cellulosic polymers (including hydroxypropyl cellulose, hydroxypropylmethylcellulose, methyl cellulose, ethyl cellulose, hydroxyethyl cellulose, carboxymethyl cellulose and the like), veegum, carbomer (e.g., carbopol), sodium, dextrin, guar gum, hydrogenated vegetable oil, magnesium aluminum silicate, maltodextrin, polymethacrylates, povidone (e.g., KOLLIDON, PLASDONE), microcrystalline cellulose, among others. Binding agents also include, e.g., acacia, agar, alginic acid, cabomers, carrageenan, cellulose acetate phthalate, ceratonia, chitosan, confectioner's sugar, copovidone, dextrates, dextrin, dextrose, ethylcellulose, gelatin, glyceryl behenate, guar gum, hydroxyethyl cellulose, hydroxyethylmethyl cellulose, hydroxypropyl cellulose, hydroxypropyl starch, hypromellose, inulin, lactose, magnesium aluminum silicate, maltodextrin, maltose, methylcellulose, poloxamer, polycarbophil, polydextrose, polyethylene oxide, polymethylacrylates, povidone, sodium alginate, sodium carboxymethylcellulose, starch, pregelatinized starch, stearic acid, sucrose, and zein. The binding agent can be, relative to the drug core, in the amount of about 2% w/w of the drug core; about 4% w/w of the drug core, about 6% w/w of the drug core, about 8% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, about 34% w/w of the drug core, about 36% w/w of the drug core, about 38% w/w of the drug core, about 40% w/w of the drug core, about 42% w/w of the drug core, about 44% w/w of the drug core, about 46% w/w of the drug core, about 48% w/w of the drug core, about 50% w/w of the drug core, about 52% w/w of the drug core, about 54% w/w of the drug core, about 56% w/w of the drug core, about 58% w/w of the drug core, about 60% w/w of the drug core, about 62% w/w of the drug core, about 64% w/w of the drug core, about 66% w/w of the drug core; about 68% w/w of the drug core, about 70% w/w of the drug core, about 72% w/w of the drug core, about 74% w/w of the drug core, about 76% w/w of the drug core, about 78% w/w of the drug core, about 80% w/w of the drug core, about 82% w/w of the drug core, about 84% w/w of the drug core, about 86% w/w of the drug core, about 88% w/w of the drug core, about 90% w/w of the drug core, about 92% w/w of the drug core, about 94% w/w of the drug core, about 96% w/w of the drug core, about 98% w/w of the drug core, or more, if determined to be appropriate. In certain embodiments, a suitable amount of a particular binder is determined by one of ordinary skill in the art.

In certain embodiments, formulations provided herein comprise one or more diluents. Diluents may be used, e.g., to increase bulk so that a practical size tablet is ultimately provided. Suitable diluents include dicalcium phosphate, calcium sulfate, lactose, cellulose, kaolin, mannitol, sodium chloride, dry starch, microcrystalline cellulose (e.g., AVICEL), microfine cellulose, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT), potassium chloride, sodium chloride, sorbitol and talc, among others. Diluents also include, e.g., ammonium alginate, calcium carbonate, calcium phosphate, calcium sulfate, cellulose acetate, compressible sugar, confectioner's sugar, dextrates, dextrin, dextrose, erythritol, ethylcellulose, fructose, fumaric acid, glyceryl palmitostearate, isomalt, kaolin, lacitol, lactose, mannitol, magnesium carbonate, magnesium oxide, maltodextrin, maltose, medium-chain triglycerides, microcrystalline cellulose, microcrystalline silicified cellulose, powered cellulose, polydextrose, polymethacrylates, simethicone, sodium alginate, sodium chloride, sorbitol, starch, pregelatinized starch, sucrose, sulfobutylether-β-cyclodextrin, talc, tragacanth, trehalose, and xylitol. Diluents may be used in amounts calculated to obtain a desired volume for a tablet or capsule; in certain embodiments, a diluent is used in an amount of about 5% or more, about 10% or more, about 15% or more, about 20% or more, about 22% or more, about 24% or more, about 26% or more, about 28% or more, about 30% or more, about 32% or more, about 34% or more, about 36% or more, about 38% or more, about 40% or more, about 42% or more, about 44% or more, about 46% or more, about 48% or more, about 50% or more, about 52% or more, about 54% or more, about 56% or more, about 58% or more, about 60% or more, about 62% or more, about 64% or more, about 68% or more, about 70% or more, about 72% or more, about 74% or more, about 76% or more, about 78% or more, about 80% or more, about 85% or more, about 90% or more, or about 95% or more, weight/weight, of a drug core; between about 10% and about 90% w/w of the drug core; between about 20% and about 80% w/w of the drug core; between about 30% and about 70% w/w of the drug core; between about 40% and about 60% w/w of the drug core. In certain embodiments, a suitable amount of a particular diluent is determined by one of ordinary skill in the art.

In certain embodiments, formulations provided herein comprise one or more lubricants. Lubricants may be used, e.g., to facilitate tablet manufacture; examples of suitable lubricants include, for example, vegetable oils such as peanut oil, cottonseed oil, sesame oil, olive oil, corn oil, and oil of theobroma, glycerin, magnesium stearate, calcium stearate, and stearic acid. In certain embodiments, stearates, if present, represent no more than approximately 2 weight % of the drug-containing core. Further examples of lubricants include, e.g., calcium stearate, glycerin monostearate, glyceryl behenate, glyceryl palmitostearate, magnesium lauryl sulfate, magnesium stearate, myristic acid, palmitic acid, poloxamer, polyethylene glycol, potassium benzoate, sodium benzoate, sodium chloride, sodium lauryl sulfate, sodium stearyl fumarate, stearic acid, talc, and zinc stearate. In particular embodiments, the lubricant is magnesium stearate. In certain embodiments, the lubricant is present, relative to the drug core, in an amount of about 0.2% w/w of the drug core, about 0.4% w/w of the drug core, about 0.6% w/w of the drug core, about 0.8% w/w of the drug core, about 1.0% w/w of the drug core, about 1.2% w/w of the drug core, about 1.4% w/w of the drug core, about 1.6% w/w of the drug core, about 1.8% w/w of the drug core, about 2.0% w/w of the drug core, about 2.2% w/w of the drug core, about 2.4% w/w of the drug core, about 2.6% w/w of the drug core, about 2.8% w/w of the drug core, about 3.0% w/w of the drug core, about 3.5% w/w of the drug core, about 4% w/w of the drug core, about 4.5% w/w of the drug core, about 5% w/w of the drug core, about 6% w/w of the drug core, about 7% w/w of the drug core, about 8% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 25% w/w of the drug core, about 30% w/w of the drug core, about 35% w/w of the drug core, about 40% w/w of the drug core, between about 0.2% and about 10% w/w of the drug core, between about 0.5% and about 5% w/w of the drug core, or between about 1% and about 3% w/w of the drug core. In certain embodiments, a suitable amount of a particular lubricant is determined by one of ordinary skill in the art.

In certain embodiments, formulations provided herein comprise one or more disintegrants. Disintegrants may be used, e.g., to facilitate disintegration of the tablet, and may be, e.g., starches, clays, celluloses, algins, gums or cross-linked polymers. Disintegrants also include, e.g., alginic acid, carboxymethylcellulose calcium, carboxymethylcellulose sodium (e.g., AC-DI-SOL, PRIMELLOSE), colloidal silicon dioxide, croscarmellose sodium, crospovidone (e.g., KOLLIDON, POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB) and starch. Additional disintegrants include, e.g., calcium alginate, chitosan, sodium docusate, hydroxypropyl cellulose, and povidone. In certain embodiments, the disintegrant is, relative to the drug core, present in the amount of about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, greater than about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular disintegrant is determined by one of ordinary skill in the art.

In certain embodiments, formulations provided herein comprise one or more stabilizers. Stabilizers (also called absorption enhancers) may be used, e.g., to inhibit or retard drug decomposition reactions that include, by way of example, oxidative reactions. Stabilizing agents include, e.g., d-Alpha-tocopheryl polyethylene glycol 1000 succinate (Vitamin E TPGS), acacia, albumin, alginic acid, aluminum stearate, ammonium alginate, ascorbic acid, ascorbyl palmitate, bentonite, butylated hydroxytoluene, calcium alginate, calcium stearate, calcium carboxymethylcellulose, carrageenan, ceratonia, colloidal silicon dioxide, cyclodextrins, diethanolamine, edetates, ethylcellulose, ethyleneglycol palmitostearate, glycerin monostearate, guar gum, hydroxypropyl cellulose, hypromellose, invert sugar, lecithin, magnesium aluminum silicate, monoethanolamine, pectin, poloxamer, polyvinyl alcohol, potassium alginate, potassium polacrilin, povidone, propyl gallate, propylene glycol, propylene glycol alginate, raffinose, sodium acetate, sodium alginate, sodium borate, sodium carboxymethyl cellulose, sodium stearyl fumarate, sorbitol, stearyl alcohol, sufobutyl-b-cyclodextrin, trehalose, white wax, xanthan gum, xylitol, yellow wax, and zinc acetate. In certain embodiments, the stabilizer is, relative to the drug core, present in the amount of about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular stabilizer is determined by one of ordinary skill in the art.

In certain embodiments, formulations provided herein comprise one or more glidants. Glidants may be used, e.g., to improve the flow properties of a powder composition or granulate or to improve the accuracy of dosing. Excipients that may function as glidants include, e.g., colloidal silicon dioxide, magnesium trisilicate, powdered cellulose, starch, tribasic calcium phosphate, calcium silicate, powdered cellulose, colloidal silicon dioxide, magnesium silicate, magnesium trisilicate, silicon dioxide, starch, tribasic calcium phosphate, and talc. In certain embodiments, the glidant is, relative to the drug core, present in the amount of less than about 1% w/w of the drug core, about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular glidant is determined by one of ordinary skill in the art.

In certain embodiments, formulations provided herein comprise one or more permeation enhancers (also called, e.g., permeability enhancers). In particular embodiments, d-alpha-tocopheryl polyethylene glycol-1000 succinate (Vitamin E TPGS) is used as a permeation enhancer. In particular embodiments, one or more other suitable permeation enhancers are used, including, e.g., any permeation enhancer known in the art.

In one embodiment, the pharmaceutical compositions provided herein may be administered orally, parenterally, by inhalation spray, topically, rectally, nasally, buccally, vaginally or via an implanted reservoir, preferably by oral administration or administration by injection. In one embodiment, the pharmaceutical compositions may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

In one embodiment, the pharmaceutical compositions provided herein may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

In one embodiment, the pharmaceutical compositions provided herein may also be administered in the form of suppositories for rectal administration. These compositions can be prepared by mixing a compound of one aspect of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions provided herein is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of one aspect of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions provided herein may also be topically applied to the lower intestinal tract by rectal suppository formulation or in a suitable enema formulation. Topically-transdermal patches are also included herein.

In one embodiment, the pharmaceutical compositions provided herein may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

In one embodiment, the compositions provided herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. In one embodiment, the pharmaceutical compositions are administered from about 1 to about 6 times per day or alternatively, as a continuous infusion. Such administration can be used as a chronic or acute therapy. The amount of active ingredient that may be combined with the carrier materials to produce a single dosage form varies depending upon the host treated and the particular mode of administration. A typical preparation contains from about 5% to about 95% active compound (w/w). Alternatively, such preparations contain from about 20% to about 80% active compound.

Lower or higher doses than those recited above may be required. Specific dosage and treatment regimens for any particular subject depends upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination provided herein may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

Solid Dispersions of Compound 1

In certain embodiment, COMPOUND 1 is administered in compositions, comprising COMPOUND 1, and one or more polymer(s) as part of a solid dispersion (e.g., an amorphous solid dispersion). In some embodiments, the solid dispersion comprises COMPOUND 1, and one or more polymer(s). In some embodiments, the solid dispersion comprises COMPOUND 1, one or more polymer(s), and one or more surfactant(s). In some embodiments, the solid dispersion comprises COMPOUND 1, and one polymer. In some embodiments, the solid dispersion comprises COMPOUND 1, one polymer, and a surfactant.

In certain embodiment, the solid dispersions provided herein, comprising COMPOUND 1, enhance the solubility of COMPOUND 1 relative to a neat crystalline form of COMPOUND 1 (e.g., Form 1 or Form 2), and thus provide improved exposure upon oral dosing of the solid dispersion to a subject. In one embodiment, the solid dispersion comprises COMPOUND 1, one or more polymer(s), and optionally one or more solubility enhancing surfactant.

For example, the aqueous solubility of Form 1 is about 0.025 mg/mL to about 0.035 mg/mL and the aqueous solubility of Form 2 is about 0.008 mg/mL to about 0.010 mg/mL.

Form 2 has a solubility of about 0.018 mg/mL in fasted state simulated intestinal fluid (FASSIF) at a pH of 6.1 at 4 hours. In comparison, amorphous spray-dried dispersions have a solubility of about 0.05 mg/mL to about 0.50 mg/mL in FASSIF at 3 hours.

In some embodiments, the solid dispersion exhibits at least about 20%, at least about 30%, at least about 40%, at least about 50%, at least about 60%, at least about 70%, at least about 80%, or at least about 90% higher exposure of COMPOUND 1, when administered to a subject as compared to administration of in-situ amorphous COMPOUND 1. In some embodiments, the solid dispersion exhibits at least about 20%, at least about 30%, at least about 40%, at least about 50%, at least about 60%, at least about 70%, at least about 80%, or at least about 90% higher exposure of COMPOUND 1, when administered to a subject as compared to administration of neat crystalline COMPOUND 1.

In rat and monkey pharmacokinetics studies, modest exposure improvement is observed upon administration of solid dispersion oral dosage forms as compared to in-situ amorphous dosing shows. For example, a solid dispersion containing 50% w/w COMPOUND 1 and 50% w/w Polyvinyl Acetate Phthalate (PVAP) has approximately two-fold higher exposure as compared to in-situ amorphous COMPOUND 1 in male Sprague Dawley rats. There is no significant difference in exposure between a solid dispersion containing 70% w/w COMPOUND 1 and 30% w/w oral dosage form as compared to in-situ amorphous COMPOUND 1. In male cynomologus monkeys, the exposure of a solid dispersion containing 50% w/w COMPOUND 1 and 50% w/w hydroxypropylmethylcellulose acetate succinate, also known as hypromellose acetate succinate, (HPMCAS) shows no significant difference as compared to the in-situ amorphous COMPOUND 1. Similarly, a solid dispersion containing 50% w/w COMPOUND 1 and 50% w/w hydroxypropylmethylcellulose also known as hypromellose phthalate (HPMC-Phthalate) shows no significant difference as compared to the in-situ amorphous COMPOUND 1. While in-situ amorphous therapeutic compounds are commonly used for dosing in animal studies, they are not suitable dosage forms for dosing in humans.

In rats, COMPOUND 1 exposure is improved when solid dispersion dosage forms are administered as compared to neat crystalline COMPOUND 1 Form 2.

In some embodiments, at least a portion of COMPOUND 1, in the solid dispersion is in the amorphous state (e.g., at least about 50%, at least about 55%, at least about 60%, at least about 65%, at least about 70%, at least about 75%, at least about 80%, at least about 85%, at least about 90%, at least about 95%, at least about 98%, or at least about 99%). In other embodiments, the solid dispersion is substantially free of crystalline COMPOUND 1.

In some embodiments, the composition is an amorphous solid (e.g., spray dried) dispersion comprising COMPOUND 1, and a polymer. The amorphous solid dispersion can include, e.g., less than about 30%, less than about 20%, less than about 15%, less than about 10%, less than about 5%, less than about 4%, less than about 3%, less than about 2%, or less than about 1% of crystalline COMPOUND 1, e.g., be substantially free of crystalline COMPOUND 1.

In one embodiment, the solid dispersion exhibits a predetermined level of physical and/or chemical stability. E.g., the solid dispersion retains about 50%, about 60%, about 70%, about 80%, about 90%, about 95%, about 98%, or about 99%, of amorphous COMPOUND 1, when stored at 25° C. in a closed water tight container, e.g., an amber glass vial, high density polyethylene (HDPE) container or double polyethylene bags with twisted nylon tie placed in an HDPE container with desiccant.

In some embodiments, the polymer increases the chemical or physical stability (e.g., as measured by a Modulated Differential Scanning Calorimeter) of COMPOUND 1, when stored (e.g., at 2-8° C., e.g., 4° C. or at room temperature) by at least about 10% (e.g., by at least about 20%, by at least about 30%, by at least about 40%, by at least about 50%, by at least about 60%, by at least about 70%, by at least about 80%, or by at least about 90%) compared to amorphous COMPOUND 1, without being in the presence of the polymer.

A solid dispersion generally exhibits a glass transition temperature, where the dispersion makes a transition from a glassy solid to a rubbery composition. In general, the higher the glass transition temperature, the greater the physical stability of the dispersion. The existence of a glass transition temperature generally indicates that at least a large portion of the composition (e.g., dispersion) is in an amorphous state. The glass transition temperature (Tg) of a solid dispersion suitable for pharmaceutical applications is generally at least about 50° C. In some embodiments, higher temperatures are preferred. Therefore, in some embodiments, a solid dispersion disclosed herein has a Tg of at least about 100° C. (e.g., at least about 100° C., at least about 105° C., at least about 110° C., at least about 115° C., at least about 120° C., at least about 125° C., at least about 130° C., at least about 135° C., at least about 140° C., at least about 150° C., at least about 160° C., at least about 170° C., at least about 175° C., at least about 180° C., or at least about 190° C.). In some embodiments, the Tg is up to about 200° C. In some embodiments, the Tg is up to about 130° C. (e.g., at least about 110° C., at least about 111° C., at least about 112° C., at least about 113° C., at least about 114° C., at least about 115° C., at least about 116° C., at least about 117° C., at least about 118° C., at least about 119° C., at least about 120° C., at least about 121° C., at least about 122° C., at least about 123° C., at least about 124° C., at least about 125° C., at least about 1216° C., at least about 127° C., at least about 128° C., at least about 129° C., or at least about 130° C.). Unless otherwise noted, the glass transition temperatures disclosed herein are measured under dry conditions.

In some embodiments the solid dispersion has a higher glass transition temperature than the glass transition temperature of amorphous COMPOUND 1, without being in the presence of the polymer(s). In some embodiments, the solid dispersion has a relaxation rate that is lower than the relaxation rate of amorphous COMPOUND 1, without being in the presence of the polymer(s).

Examples of polymers in the solid dispersion include cellulose derivatives (e.g., hydroxypropylmethylcellulose also known as hypromellose, (HPMC), hydroxypropylmethylcellulose phthalate, also known as hypromellose phthalate (HPMCP), hydroxypropylmethylcellulose acetate succinate, also known as hypromellose acetate succinate, (HPMCAS), hydroxypropylcellulose (HPC)), ethylcellulose, or cellulose acetate phthalate; polyvinylpyrrolidones (PVP); polyethylene glycols (PEG); polyvinyl alcohols (PVA); polyvinyl esters, such as Polyvinyl Acetate Phthalate (PVAP); acrylates, such as polymethacrylate (e.g., Eudragit® E); cyclodextrins (e.g., .beta.-cyclodextrin); Poly (D, L-lactide) (PLA), Poly (D,L-lactide, co-glycolide acid (PLGA); and copolymers and derivatives thereof, including for example polyvinylpyrollidone-vinyl acetate (PVP-VA), Polyvinyl caprolactam-polyvinyl, and acetate-polyethyleneglycol copolymer, Methylacrylate/methacrylic acid copolymer; Soluplus; Copovidone; and mixtures thereof.

In some embodiments, the solid dispersion includes one water-soluble polymer. In some embodiments, the solid dispersion includes one partially water-soluble polymer. In some embodiments, the polymer is a cellulose polymer.

In some embodiments, the polymer is HPMCAS (e.g., HPMCAS of different grades: HPMCAS-M, HPMCAS-MG or HPMCAS-HG). In some embodiments, the polymer is PVAP. In some embodiments, the polymer is HPMC (e.g., HPMC of different grades: HMPC60SH50, HPMCE50 or HPMCE15). In some embodiments, the polymer is HPMCP (e.g., HPMCP of different grades: e.g., HMPCP-HP55).

In some embodiments, the polymer is a pH-dependent enteric polymer. Such pH-dependent enteric polymers include, but are not limited to, cellulose derivatives (e.g., cellulose acetate phthalate (CAP)), HPMCP, HPMCAS, carboxymethylcellulose (CMC) or a salt thereof (e.g., a sodium salt such as (CMC-Na)); cellulose acetate trimellitate (CAT), hydroxypropylcellulose acetate phthalate (HP-CAP), hydroxypropylmethyl-cellulose acetate phthalate (HPMCAP), and methylcellulose acetate phthalate (MCAP), polymethacrylates (e.g., Eudragit S), or mixtures thereof.

In some embodiments, the polymer is hydroxypropylmethylcellulose acetate succinate, also known as hypromellose acetate succinate, (HPMCAS), e.g., HMPCAS-HG.

In another embodiment, the polymer(s) is an insoluble cross-linked polymer, for example a polyvinylpyrrolidone (e.g., Crospovidone). In another embodiment, the polymer(s) is polyvinylpyrrolidone (PVP).

In some embodiments, the one or more polymer(s) is present in the solid dispersion in an amount of between about 10% w/w and 90% w/w (e.g., between about 20% w/w and about 80% w/w; between about 30% w/w and about 70% w/w; between about 40% w/w and about 60% w/w; or between about 15% w/w and about 35% w/w). In some embodiments, the polymer(s) is present in the solid dispersion in an amount of from about 10% w/w to about 80% w/w, for example from about 30% w/w to about 75% w/w, or from about 40% w/w to about 65% w/w, or from about 45% w/w to about 55% w/w, for example, about 46% w/w, about 47% w/w, about 48% w/w, about 49% w/w, about 50% w/w, about 51% w/w, about 52% w/w, about 53% w/w, or about 54% w/w. In some embodiments, the polymer(s) is present in the solid dispersion in an amount of about 48% w/w, about 48.5% w/w, about 49% w/w, about 49.5% w/w, about 50% w/w, about 50.5% w/w, about 51% w/w, about 51.5% w/w, about 52% w/w, or about 52.5% w/w.

In some embodiments, the polymer(s) is present in the solid dispersion in an amount of from about 30% w/w to about 70% w/w. In some embodiments, the polymer(s) is present in the solid dispersion in an amount of from about 35% w/w to about 65% w/w. In some embodiments, the polymer(s) is present in the solid dispersion in an amount of from about 40% w/w to about 60% w/w. In some embodiments, the polymer(s) is present in the solid dispersion in an amount of from about 45% w/w to about 55% w/w. In some embodiments, the polymer(s) is present in the solid dispersion in an amount of about 50% w/w.

In some embodiments, COMPOUND 1, is present in the solid dispersion in an amount of from about 10% w/w and 90% w/w (e.g., between about 20% w/w and about 80% w/w; between about 30% w/w and about 70% w/w; between about 40% w/w and about 60% w/w; or between about 15% w/w and about 35% w/w). In some embodiments, COMPOUND 1, is present in the solid dispersion in an amount of from about 10% w/w to about 80% w/w, for example from about 30% w/w to about 75% w/w, or from about 40% w/w to about 65% w/w, or from about 45% w/w to about 55% w/w, for example, about 46% w/w, about 47% w/w, about 48% w/w, about 49% w/w, about 50% w/w, about 51% w/w, about 52% w/w, about 53% w/w, or about 54% w/w. In some embodiments, COMPOUND 1, is present in the solid dispersion in an amount of about 48% w/w, about 48.5% w/w, about 49% w/w, about 49.5% w/w, about 50% w/w, about 50.5% w/w, about 51% w/w, about 51.5% w/w, about 52% w/w, or about 52.5% w/w.

In some embodiments, COMPOUND 1 is present in the solid dispersion in an amount of from about 30% w/w to about 70% w/w. In some embodiments, COMPOUND 1 is present in the solid dispersion in an amount of from about 35% w/w to about 65% w/w. In some embodiments, COMPOUND 1 is present in the solid dispersion in an amount of from about 40% w/w to about 60% w/w. In some embodiments, COMPOUND 1 is present in the solid dispersion in an amount of from about 45% w/w to about 55% w/w. In some embodiments, COMPOUND 1 is present in the solid dispersion in an amount of about 50% w/w.

In another embodiment, the solid dispersion includes about 20% w/w to about 80% w/w COMPOUND 1, and about 20% w/w to about 80% of polymer(s). In another embodiment, the solid dispersion includes about 25% w/w to about 75% w/w COMPOUND 1, and about 25% w/w to about 75% of polymer(s). In another embodiment, the solid dispersion includes about 30% w/w to about 70% w/w COMPOUND 1, and about 30% w/w to about 70% of polymer(s). In another embodiment, the solid dispersion includes about 35% w/w to about 65% w/w COMPOUND 1, and about 35% w/w to about 65% of polymer(s). In another embodiment, the solid dispersion includes about 40% w/w to about 60% w/w COMPOUND 1, and about 40% w/w to about 60% of polymer(s). In another embodiment, the solid dispersion includes about 45% w/w to about 55% w/w COMPOUND 1, and about 45% w/w to about 55% of polymer(s). In another embodiment, the solid dispersion includes about 50% w/w COMPOUND 1, and about 50% w/w of polymer(s).

In another embodiment, the solid dispersion includes about 45% w/w to about 55% w/w COMPOUND 1, and about 45% w/w to about 55% w/w HPMCAS (e.g., HPMCAS-MG or HPMCAS-HG, or other grades such as LF, MF, HF, or LG) or PVAP. In another embodiment, the solid dispersion includes about 50% w/w COMPOUND 1, and about 50% w/w of HPMCAS.

In some embodiments, the solid dispersion also includes a surfactant or inert pharmaceutically acceptable substance. Examples of surfactants in the solid dispersion include sodium lauryl sulfate (SLS), vitamin E or a derivative thereof (e.g., vitamin E TPGS), Docusate Sodium, sodium dodecyl sulfate, polysorbates (such as Tween 20 and Tween 80), poloxamers (such as Poloxamer 335 and Poloxamer 407), glyceryl monooleate, Span 65, Span 25, Capryol 90, pluronic copolymers (e.g., Pluronic F108, Pluronic P-123), and mixtures thereof. In some embodiments, the surfactant is SLS. In some embodiments, the surfactant is vitamin E or a derivative thereof (e.g., vitamin E TPGS).

In some embodiments, the surfactant is present in the solid dispersion in an amount of from about 0.1% w/w to about 10% w/w, for example from about 0.5% w/w to about 2% w/w, or from about 1% w/w to about 3% w/w, from about 1% w/w to about 4% w/w, or from about 1% w/w to about 5% w/w. In some embodiments, the surfactant is present in the solid dispersion in an amount of about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, or about 1% w/w. In some embodiments, the surfactant is present in the solid dispersion in an amount of about 0.5% w/w, about 1% w/w, about 1.5% w/w, about 2% w/w, about 2.5% w/w, about 3% w/w, about 3.5% w/w, about 4% w/w, about 4.5% w/w, or about 5% w/w.

Processes for Preparing Solid Dispersions

In some embodiments, the solid dispersion may be prepared according to a process described herein. In general, methods that could be used include those that involve rapid removal of solvent or solvent mixture from a mixture or cooling a molten sample. Such methods include, but are not limited to, rotational evaporation, freeze-drying (i.e., lyophilization), vacuum drying, melt congealing, and melt extrusion. One embodiment of this disclosure involves solid dispersion obtained by spray-drying. In one embodiment, the product obtained by spray drying is dried to remove the solvent or solvent mixture.

Preparations disclosed herein, e.g., a pharmaceutical composition, can be obtained by spray-drying a mixture comprising COMPOUND 1, one or more polymer(s), and an appropriate solvent or solvent mixture. Spray drying involves atomization of a liquid mixture containing, e.g., a solid and a solvent or solvent mixture, and removal of the solvent or solvent mixture. The solvent or solvent mixture can also contain a nonvolatile solvent, such as glacial acetic acid. Atomization may be done, for example, through a two-fluid or pressure or electrosonic nozzle or on a rotating disk.

Spray drying converts a liquid feed to a dried particulate form. Spray drying generally involves the atomization of a liquid feed solution into a spray of droplets and contacting the droplets with hot air or gas in a drying chamber. The sprays are generally produced by either rotary (wheel) or nozzle atomizers. Evaporation of moisture from the droplets and formation of dry particles proceed under controlled temperature and airflow conditions.

Optionally, a secondary drying process such as fluidized bed drying or vacuum drying, may be used to reduce residual solvents (and other additives, such as glacial acetic acid) to pharmaceutically acceptable levels. Typically, spray-drying involves contacting a highly dispersed liquid suspension or solution (e.g., atomized solution), and a sufficient volume of hot air or gas (e.g., nitrogen, e.g., pure nitrogen) to produce evaporation and drying of the liquid droplets. The preparation to be spray dried can be any solution, coarse suspension, slurry, colloidal dispersion, or paste that may be atomized using the selected spray-drying apparatus. In a standard procedure, the preparation is sprayed into a current of warm filtered air (or into gas, e.g., nitrogen) that evaporates the solvent and conveys the dried product to a collector (e.g., a cyclone). The spent air or gas is then exhausted with the solvent (or solvent mixture including any additives such as glacial acetic acid), (e.g., then filtered) or alternatively the spent air or gas is sent to a condenser to capture and potentially recycle the solvent or solvent mixture. For example, if a gas (e.g., nitrogen) is used, the gas is then optionally recycled, heated again and returned to the unit in a closed loop system. Commercially available types of apparatus may be used to conduct the spray-drying. For example, commercial spray dryers are manufactured by Buchi Ltd. and Niro (e.g., the PSD line of spray driers manufactured by Niro).

Spray-drying typically employs solids loads of material from about 1% to about 30% or up to about 50% (i.e., therapeutically active compound plus and excipients), preferably at least about 10%. In some embodiments, solids loads of less than 10% may result in poor yields and unacceptably long run-times. In general, the upper limit of solids loads is governed by the viscosity of (e.g., the ability to pump) the resulting solution and the solubility of the components in the solution. Generally, the viscosity of the solution can determine the size of the particle in the resulting powder product.

Techniques and methods for spray-drying may be found in Perry's Chemical Engineering Handbook, 6th Ed., R. H. Perry, D. W. Green & J. O. Maloney, eds., McGraw-Hill Book Co. (1984); and Marshall "Atomization and Spray-Drying" 50, Chem. Eng. Prog. Monogr. Series 2 (1954). In general, the spray-drying is conducted with an inlet temperature of from about 40° C. to about 200° C., for example, from about 70° C. to about 150° C., preferably from about 40° C. to about 60° C., about 50° C. to about 55° C., or about 80° C. to about 110° C., e.g., about 90° C. The spray-drying is generally conducted with an outlet temperature of from about 20° C. to about 100° C., for example from about 25° C. to about 30° C. (e.g., about 26° C.), about 40° C. to about 50° C., about 50° C. to about 65° C., e.g., about 56° C. to about 58° C.

Removal of the solvent or solvent mixture may require a subsequent drying step, such as tray drying, fluid bed drying (e.g., from about room temperature to about 100° C.), vacuum drying, microwave drying, rotary drum drying or biconical vacuum drying (e.g., from about room temperature to about 200° C.).

In one embodiment, the spray-drying is fluidized spray drying (FSD). The steps in FSD can include, for example: preparing a liquid feed solution (e.g., containing COMPOUND 1, and optionally a polymer(s) and/or surfactant(s), dissolved or suspended in solvent(s)); atomizing (e.g., with a pressure nozzle, a rotary atomizer or disk, two-fluid nozzle or other atomizing methods) the feed solution upon delivery into the drying chamber of a spray dryer, e.g., operating in FSD mode; drying the feed solution in the drying chamber with heated air or a heated gas (e.g., nitrogen) to obtain a product, wherein larger particles of product separate out, e.g., drop out, while fines are carried by a stream of air or gas up to the top of the drying chamber (e.g., by natural convection) and to a cyclone, and re-introducing (e.g., at the top of the drying chamber or axially to the middle of the chamber) the fines into the drying chamber, wherein the re-introduced fines can agglomerate with newly formed product to generate an agglomerated product, wherein if the agglomerated product is large enough, it will separate out, if it is not large enough to separate out, the agglomerated product will be carried by convection to the top of the chamber and to the cyclone and re-introduced into the chamber. This process repeats until an agglomerated product that is large enough to drop out is formed. The fines can be re-introduced from the cyclone to the drying chamber via a feed pipe.

In some embodiments, rather than drying the feed solution with heated air or a heated gas, the feed solution can instead be spray congealed, e.g., the chamber is at room temperature (e.g., 21±4° C.) or is cooled, e.g., cooled gas (e.g., nitrogen) is used for the process.

FSD can further include collecting the agglomerated product in a first fluidizing chamber; which can be followed by discharging the agglomerated product from the first fluidizing chamber to a second fluidizing chamber, wherein a post-drying process can occur.

The agglomerated product (e.g., that separates out in the drying chamber) can then be transferred from the second fluidizing chamber to a third fluidizing chamber, where the agglomerated product is cooled. The agglomerated product (e.g., a solid dispersion of an amorphous compound) can then be further processed. For example, the product can be directly compressed. The product can optionally be blended with a surfactant, excipient, or pharmaceutically acceptable carrier, e.g., prior to direct compression. The product can optionally be further processed, e.g., milled, granulated, blended, and/or mixed with a melt granulate, surfactant, excipient, and/or pharmaceutically acceptable carrier.

FSD can be performed in a commercial spray dryer operating in fluidized spray dryer mode (FSD mode). FSD can be accomplished in either open cycle mode or closed cycle mode (e.g., the drying gas, e.g., nitrogen, is recycled).

Examples of suitable spray dryers for use in FSD include dryers from Niro (e.g., the PSD line of spray driers manufactured by Niro: PHARMASD™; Chemical or SD line dryers). FSD can essentially be performed in any spray dryer that is configured to allow for the re-introduction of fines into the drying chamber.

Additional post drying, e.g., in a vacuum or fluidized bed dryer or a double cone or biconical post-dryer or a tumble dryer, can be performed if needed/applicable to remove further solvents. In some embodiments, a post-drying step is performed.

To remove the solvent or solvent mixture, vacuum drying, spray drying, fluidized spray drying, tray drying, lyophilization, rotovapping, and other drying procedures may be applied. Applying any of these methods using appropriate processing parameters, according to this disclosure, would provide COMPOUND 1 in an amorphous state in the final solid dispersion product. Upon use of appropriate conditions (e.g., low outlet temperatures in the spray dryer, use of low boiling point solvents, use of heated gas) that result in a dispersion, e.g., powder, with desirable properties (e.g., median particle size (d50) of 40-200 microns 9 e.g., 40-150 microns), powder bulk density of >0.2 g/ml (e.g., 0.2 to 0.5 g/ml), or >0.25 g/ml, improved powder flowability (e.g., low cohesion forces, low interparticle internal friction); and/or dry powder with low OVIs (Organic Volatile Impurities), e.g., below ICH limits and/or user specifications), the dispersion can be directly compressed into a dosage form.

In some embodiments, the inlet temperature is between about 50° C. and about 200° C., e.g., between about 60° C. and about 150° C., between about 70° C. and about 100° C., between about 60° C. and about 95° C., between about 65° C. and about 85° C., between about 70° C. and about 90° C., between about 85° C. and about 95° C., or between about 70° C. and about 85° C.

In some embodiments, the outlet temperature is between about room temperature (e.g., USP room temperature (e.g., 21±4° C.)) and about 80° C., e.g., between about 25° C. and about 75° C., between about 30° C. and about 65° C., between about 35° C. and about 70° C., between about 40° C. and about 65° C., between about 45° C. and about 60° C., between about 35° C. and about 45° C., between about 35° C. and about 40° C., or between about 37° C. and about 40° C.

In some embodiments, the temperature set points of the fluidized beds (the temperature for each bed being selected independently from the temperature selected for another bed) is between about room temperature (e.g., USP room temperature (e.g., 21±4° C.)) and about 100° C., e.g., between about 30° C. and about 95° C., between about 40° C. and about 90° C., between about 50° C. and about 80° C., between about 60° C. and about 85° C., between about 65° C. and about 95° C., or between about 80° C. and about 95° C.

FSD can be performed on a mixture containing COMPOUND 1. For example, FSD can be performed on a mixture containing COMPOUND 1, and one or more polymer(s), and optionally one or more surfactant(s), and optionally one or more additional excipients(s)) to obtain a solid dispersion of amorphous COMPOUND 1 thereof, e.g., that can be directly compressed into an oral dosage form (e.g., tablet). Alternatively, the dispersion can be blended with one or more excipients prior to compression.

In one embodiment, the process for preparing a solid dispersion of COMPOUND 1 comprises:
a) forming a mixture of COMPOUND 1, one or more polymer(s), and one or more solvent(s); and
b) rapidly removing the solvent(s) from the solution to form a solid amorphous dispersion comprising COMPOUND 1 and the one or more polymer(s). The one or more polymer(s) and one or more solvent(s) may be any of those disclosed herein.

In some embodiments, the solvent is removed by spray drying. In some embodiments the solid dispersion is tray dried using a convection tray dryer. In some embodiments, the solid dispersion is screened.

In one embodiment, COMPOUND 1 is crystalline. In another embodiment, COMPOUND 1 is amorphous.

As would be appreciated by one of skill in the art, spray drying may be done and is often done in the presence of an inert gas such as nitrogen. In certain embodiments, processes that involve spray drying may be done in the presence of a supercritical fluid involving carbon dioxide or a mixture including carbon dioxide.

In another embodiment, the process for preparing a solid dispersion of COMPOUND 1 comprises:
a) forming a mixture of COMPOUND 1, a polymer, and a solvent; and
b) spray-drying the mixture to form a solid dispersion comprising COMPOUND 1 and the polymer.

Post-drying and/or polishing the wet spray dried dispersion to below ICH or given specifications for residual solvents can optionally be performed.

These processes may be used to prepare the pharmaceutical compositions disclosed herein. The amounts and the features of the components used in the processes may be as disclosed herein.

In some embodiments, the solvent comprises one or more volatile solvent(s) to dissolve or suspend COMPOUND 1 and the polymer(s). In some embodiments, the one or more solvent(s) completely dissolves COMPOUND 1 and the polymer(s).

In some embodiments, the one or more solvent(s) is a volatile solvent (e.g., methylene chloride, acetone, methanol, ethanol, chloroform, tetrahydrofuran (THF), or a mixture thereof). Examples of suitable volatile solvents include those that dissolve or suspend the therapeutically active compound either alone or in combination with another co-solvent. In some embodiments, the solvent(s) completely dissolves the therapeutically active compound. In some embodiments, the solvent is acetone. In some embodiments, the solvent is methanol.

In some embodiments, the solvent is a non-volatile solvent (e.g., organic acids such as glacial acetic acid, dimethyl sulfoxide (DMSO), dimethylformamide (DMF), or water). In some embodiments, a non-volatile solvent is a component in a solvent system. For example the non-volatile solvent is present as a component in a solvent from about 1% to about 20% w/w (e.g., from about 3% w/w to about 15% w/w, from about 4% w/w to about 12% w/w, or from about 5% w/w to about 10% w/w).

In some embodiments, the solvent is a mixture of solvents. For example, the solvent can include from about 0% to about 30% acetone and from about 70% to about 100% methanol, or the solvent can include from about 0% to about 40% acetone and from about 60% to about 100% methanol. Other exemplary ratios of methanol to acetone include 80:20, 75:25, 70:30, 60:40, 55:45, and 50:50.

In some embodiments, the solvent is a combination of solvents including at least one non-volatile solvent. For example, the solvent is a combination of components that includes both a volatile solvent and a non-volatile solvent. In some embodiments, the solvent system is a combination of a volatile solvent or combination of solvents such as methanol and acetone with a non-volatile solvent such as glacial acetic acid. For example, the solvent system comprises from about 40% to about 80% methanol, from about 20% to about 35% acetone, and from about 1% to about 15% glacial acetic acid (e.g., from about 50% to about 70% methanol, from about 25% to about 30% acetone, and from about 3% to about 12% glacial acetic acid).

In some embodiments, the solvent system is a combination of a volatile solvent or combination of solvents such as methanol and acetone with a non-volatile solvent such as water. For example, the solvent system comprises from about 40% to about 80% methanol, from about 20% to about 35% acetone, and from about 0.1% to about 15% water (e.g., from about 50% to about 70% methanol, from about 25% to about 30% acetone, and from about 1% to about 5% water).

In certain embodiments, the pharmaceutical compositions of the solid dispersion may be made by a process described herein. For example, a solid dispersion of: (a) COMPOUND 1 and (b) one or more polymer(s), and optionally one or more surfactant(s) and optionally one or more additional excipient(s).

Pharmaceutical Compositions Containing Solid Dispersions of COMPOUND 1

In certain embodiments, provided herein are pharmaceutical compositions, comprising: (a) a solid dispersion, comprising COMPOUND 1 and a polymer; and (b) one or more pharmaceutically acceptable carrier(s). Examples of pharmaceutically acceptable carriers are fillers, disintegrants, wetting agents, glidants, and lubricants.

In some embodiments, the pharmaceutical compositions may be orally administered in any orally acceptable dosage form (oral dosage form) including, but not limited to, capsules, tablets, emulsions and aqueous suspensions, dispersions and solutions.

In some embodiments the pharmaceutical composition is a tablet.

In some embodiments the pharmaceutical composition (e.g., oral dosage form) comprises a directly compressed dosage form of COMPOUND 1.

In some embodiments, the pharmaceutical composition (e.g., oral dosage form) also includes a filler. The filler can be, for example, microcrystalline cellulose, lactose, mannitol, ethyl cellulose, sorbitol, starch, sucrose, calcium phosphate, powdered cellulose, silicified microcrystalline cellulose, isomalt, or mixtures thereof. In some embodiments, the filler is microcrystalline cellulose.

In some embodiments, the filler is present in the pharmaceutical composition (e.g., oral dosage form) in an amount of between about 10% w/w and 50% w/w (e.g., between about 15% w/w and about 45% w/w; between about 20% w/w and about 40% w/w; between about 25% w/w and about 35% w/w; or between about 28% w/w and about 32% w/w). In some embodiments, the filler is present in the pharmaceutical composition (e.g., oral dosage form) in an amount of from about 20% w/w to about 35% w/w, for example from about 25% w/w to about 34% w/w, or from about 26% w/w to about 33% w/w, or from about 27% w/w to about 32% w/w, for example, about 28% w/w, about 28.5% w/w, about 29% w/w, about 29.5% w/w about 30% w/w, about 30.5% w/w, about 31% w/w, or about 31.5% w/w. In some embodiments, the filler is present in the pharmaceutical composition (e.g., oral dosage form) in an amount of about 29% w/w, about 29.1% w/w, about 29.2% w/w, about 29.3% w/w, about 29.4% w/w, about 29.5% w/w, about 29.6% w/w, about 29.7% w/w, about 29.8% w/w, about 29.9% w/w, or about 30% w/w. In some embodiments, the filler is present in the pharmaceutical composition (e.g., oral dosage form) in an amount of between about 25% w/w and about 35% w/w. In some embodiments, the filler is present in the pharmaceutical composition (e.g., oral dosage form) in an amount of about 29.5% w/w.

In some embodiments, the pharmaceutical composition (e.g., oral dosage form) also includes a disintegrant. The disintegrant can be, for example, colloidal silicon dioxide, powdered cellulose, calcium silicate, crospovidone, calcium alginate, methyl cellulose, chitosan, carboxy methyl cellulose, croscarmellose sodium, carboxymethyl starch, sodium alginate, sodium starch glycolate, pregelatinized starch, or mixtures thereof. In some embodiments, the disintegrant is croscarmellose sodium.

In some embodiments, the disintegrant is present in the pharmaceutical composition (e.g., oral dosage form) in an amount of between about 1% w/w and 15% w/w (e.g., between about 3% w/w and about 12% w/w; between about 4% w/w and about 10% w/w; between about 5% w/w and about 7% w/w; or between about 6% w/w and about 7% w/w). In some embodiments, the disintegrant is present in the pharmaceutical composition (e.g., oral dosage form) in an amount of about 3% w/w, about 3.5% w/w, about 4% w/w, about 49.5% w/w about 5% w/w, about 5.5% w/w, about 6% w/w, or about 6.5% w/w, about 7% w/w, about 7.5% w/w, about 8% w/w, about 8.5% w/w, about 9% w/w, about 9.5% w/w, or about 10% w/w. In some embodiments, the disintegrant is present in the pharmaceutical composition (e.g., oral dosage form) in an amount of between about 5% w/w and about 7% w/w. In some embodiments, the disintegrant is present in the pharmaceutical composition in an amount of about 6% w/w.

In some embodiments, the pharmaceutical composition (e.g., oral dosage form) also includes a wetting agent. The wetting agent can be, for example, sodium lauryl sulfate, sodium dodecyl sulfate, polysorbates (such as Tween 20 and Tween 80), poloxamers (such as Poloxamer 335 and Poloxamer 407), glyceryl monooleate, or mixtures thereof. In some embodiments, the wetting agent is sodium lauryl sulfate.

In some embodiments, the wetting agent is present in the pharmaceutical composition (e.g., oral dosage form) in an amount of between about 0.1% w/w and 2% w/w (e.g., between about 0.5% w/w and about 2% w/w; between about 0.5% w/w and about 1.5% w/w; or between about 1% w/w and about 1.5% w/w). In some embodiments, the wetting agent is present in the pharmaceutical composition (e.g., oral dosage form) in an amount of about 0.1% w/w, about 0.2% w/w, about 0.3% w/w, about 0.4% w/w about 0.5% w/w, about 0.6% w/w, about 0.7% w/w, or about 0.8% w/w, about 0.9% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, or about 2% w/w. In some embodiments, the wetting agent is present in the pharmaceutical composition (e.g., oral dosage form) in an amount of between about 0.5% w/w and about 1.5% w/w. In some embodiments, the wetting agent is present in the pharmaceutical composition (e.g., oral dosage form) in an amount of about 1% w/w.

In some embodiments, the pharmaceutical composition (e.g., oral dosage form) also includes a glidant. The glidant can be, for example, silicon dioxide, colloidal silicon dioxide, tribasic calcium phosphate, magnesium stearate, magnesium trisilicate, powdered cellulose, talc, starch, and mixtures thereof. In some embodiments, the glidant is colloidal silicon dioxide.

In some embodiments, the glidant is present in the pharmaceutical composition (e.g., oral dosage form) in an amount of between about 0.1% w/w and 5% w/w (e.g., between about 1% w/w and about 4% w/w; between about 1% w/w and about 3% w/w; or between about 1.5% w/w and about 2.5% w/w). In some embodiments, the glidant is present in the pharmaceutical composition (e.g., oral dosage form) in an amount of about 0.5% w/w, about 1% w/w, about 1.5% w/w, about 2% w/w about 2.5% w/w, about 3% w/w, about 3.5% w/w, or about 4% w/w, about 4.5% w/w, or about 5% w/w. In some embodiments, the glidant is present in the pharmaceutical composition (e.g., oral dosage form) in an amount of about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, 2.1% w/w, about 2.2% w/w, about 2.3% w/w, about 2.4% w/w, about 2.5% w/w, about 2.6% w/w, about 2.7% w/w, about 2.8% w/w, about 2.9% w/w, or about 3% w/w. In some embodiments, the glidant is present in the pharmaceutical composition (e.g., oral dosage form) in an amount of between about 1% w/w and about 3% w/w. In some embodiments, the glidant is present in the pharmaceutical composition (e.g., oral dosage form) in an amount of about 2% w/w.

In some embodiments, the pharmaceutical composition (e.g., oral dosage form) also includes a lubricant. The lubricant can be, for example, magnesium stearate, talc, sodium stearyl fumarate, glyceryl behenate, hydrogenated vegetable oil, zinc stearate, calcium stearate, sucrose stearate, polyvinyl alcohol, magnesium lauryl sulfate, or mixtures thereof. In some embodiments, the lubricant is magnesium stearate.

In some embodiments, the lubricant is present in the pharmaceutical composition (e.g., oral dosage form) in an amount of between about 0.1% w/w and 5% w/w (e.g., between about 1% w/w and about 4% w/w; between about 1% w/w and about 3% w/w; or between about 1% w/w and about 2% w/w). In some embodiments, the lubricant is present in the pharmaceutical composition (e.g., oral dosage form) in an amount of about 0.5% w/w, about 1% w/w, about 1.5% w/w, about 2% w/w about 2.5% w/w, about 3% w/w, about 3.5% w/w, or about 4% w/w, about 4.5% w/w, or about 5% w/w. In some embodiments, the lubricant is present in the pharmaceutical composition in an amount of about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, 2.1% w/w, about 2.2% w/w, about 2.3% w/w, about 2.4% w/w, or about 2.5% w/w. In some embodiments, the lubricant is present in the pharmaceutical composition in an amount of between about 0.5% w/w and about 2.5% w/w. In some embodiments, the lubricant is present in the pharmaceutical composition (e.g., oral dosage form) in an amount of about 1.5% w/w.

In some embodiments, the solid dispersion makes up about 25% to 85% by weight of the total weight of the pharmaceutical composition (e.g., oral dosage form). In some embodiments, the solid dispersion makes up about 50% to about 70% by weight of the total weight of the pharmaceutical composition (e.g., oral dosage form).

In some embodiments, the COMPOUND 1 makes up about 15% to 45% of the total weight of the pharmaceutical composition (e.g., oral dosage form), and the one or more polymer(s) makes up about 15% to 45% of the total weight of the pharmaceutical composition (e.g., oral dosage form).

In some embodiments, the COMPOUND 1 makes up about 20% w/w of the pharmaceutical composition (e.g., oral dosage form), the one or more polymer(s) makes up about 40% w/w of the pharmaceutical composition (e.g., oral dosage form).

In some embodiments, the COMPOUND 1 makes up about 25% w/w of the pharmaceutical composition (e.g., oral dosage form), the one or more polymer(s) makes up about 35% w/w of the pharmaceutical composition (e.g., oral dosage form).

In some embodiments, the COMPOUND 1 makes up about 30% w/w of the pharmaceutical composition (e.g., oral dosage form), the one or more polymer(s) makes up about 30% w/w of the pharmaceutical composition.

In some embodiments, the COMPOUND 1 makes up about 35% w/w of the pharmaceutical composition (e.g., oral dosage form), the one or more polymer(s) makes up about 25% w/w of the pharmaceutical composition (e.g., oral dosage form).

In some embodiments, the solid dispersion makes up from between about 50% w/w to about 70% w/w of the pharmaceutical composition (e.g., oral dosage form), the filler makes up from between about 25% w/w to about 35% w/w of the pharmaceutical composition (e.g., oral dosage form), the disintegrant makes up from between about 5% w/w to about 7% w/w of the pharmaceutical composition (e.g., oral dosage form), the wetting agent makes up from between about 0.5% w/w to about 1.5% w/w of the pharmaceutical composition (e.g., oral dosage form), the glidant makes up from between about 1% w/w to about 3% w/w of the pharmaceutical composition (e.g., oral dosage form), the lubricant makes up from between about 0.5% w/w to about 2.5% w/w of the pharmaceutical composition (e.g., oral dosage form) thereby totaling 100% by weight of the composition (e.g., oral dosage form).

In some embodiments, the solid dispersion makes up about 60% w/w of the pharmaceutical composition (e.g., oral dosage form), the filler makes up about 29.5% w/w of the pharmaceutical composition (e.g., oral dosage form), the disintegrant makes up about 6% w/w of the pharmaceutical composition (e.g., oral dosage form), the wetting agent makes up about 1% w/w of the pharmaceutical composition (e.g., oral dosage form), the glidant makes up about 2% w/w of the pharmaceutical composition (e.g., oral dosage form), the lubricant makes up about 1.5% w/w of the pharmaceutical composition (e.g., oral dosage form).

In some embodiments, the pharmaceutical composition (e.g., oral dosage form) comprises, from between about 25% w/w to about 35% w/w of COMPOUND 1 from between about 25% w/w to about 35% w/w of hypromellose acetate succinate (HPMCAS), from between about 25% w/w to about 35% w/w of microcrystalline cellulose, from between about 5% w/w to about 7% w/w croscarmellose sodium, from between about 0.5% w/w to about 1.5% w/w sodium lauryl sulfate, about from between about 1% w/w to about 3% w/w colloidal silicon dioxide, and from between about 0.5% w/w to about 2.5% w/w of magnesium stearate, thereby totaling 100% by weight of the composition (e.g., oral dosage form).

In some embodiments, the pharmaceutical composition (e.g., oral dosage form) comprises, about 30% w/w of COMPOUND 1 about 30% w/w of hypromellose acetate succinate (HPMCAS), about 29.5% w/w of microcrystalline cellulose, about 6% w/w croscarmellose sodium, about 1% w/w sodium lauryl sulfate, about 2% w/w colloidal silicon dioxide, and about 1.5% w/w of magnesium stearate.

In some embodiments, the solid dispersion, filler, disintegrant, wetting agent, glidant, and lubricant are added intragranularly. In some embodiments, an additional amount of the filler, disintegrant, glidant, and lubricant are added extragranularly.

In some embodiments, the pharmaceutical composition (e.g., oral dosage form) comprises the following intragranularly added components: the solid dispersion makes up from about 50% w/w to about 70% w/w of the pharmaceutical composition (e.g., oral dosage form), the filler makes up from about 18% w/w to about 26% w/w of the pharmaceutical composition, disintegrant makes up from about 2% w/w to about 6% w/w of the pharmaceutical composition (e.g., oral dosage form), wetting agent makes up from about 0.5% w/w to about 1.5% w/w of the pharmaceutical composition (e.g., oral dosage form), glidant makes up from about 0.5% w/w to about 1.5% w/w of the pharmaceutical composition (e.g., oral dosage form), and lubricant makes up from about 0.25% w/w to about 1% w/w of the pharmaceutical composition (e.g., oral dosage form).

In some embodiments, a the pharmaceutical composition (e.g., oral dosage form) comprises the following extragranularly added components: an additional amount of the filler makes up from about 4% w/w to about 12% w/w of the pharmaceutical composition (e.g., oral dosage form), an additional amount of the disintegrant makes up from about 1% w/w to about 3% w/w of the pharmaceutical composition (e.g., oral dosage form), an additional amount of the glidant makes up from about 0.5% w/w to about 1.5% w/w of the pharmaceutical composition (e.g., oral dosage form), and an additional amount of the lubricant makes up from about 0.5% w/w to about 1.5% w/w of the pharmaceutical composition (e.g., oral dosage form), and are added extragranularly.

In some embodiments, the pharmaceutical composition (e.g., oral dosage form) comprises, the following intragranularly added components: the solid dispersion makes up about 60% w/w of the pharmaceutical composition (e.g., oral dosage form), the filler makes up about 21.5% w/w of the pharmaceutical composition (e.g., oral dosage form), disintegrant makes up about 4% w/w of the pharmaceutical composition (e.g., oral dosage form), wetting agent makes up about 1% w/w of the pharmaceutical composition, glidant makes up about 1% w/w of the pharmaceutical composition (e.g., oral dosage form), and lubricant makes up about 0.5% w/w of the pharmaceutical composition (e.g., oral dosage form).

In some embodiments, the pharmaceutical composition (e.g., oral dosage form) comprises the following extragranularly added components: an additional amount of the filler makes up about 8% w/w of the pharmaceutical composition (e.g., oral dosage form), an additional amount of the disintegrant makes up about 2% w/w of the pharmaceutical composition (e.g., oral dosage form), an additional amount of the glidant makes up about 1% w/w of the pharmaceutical composition (e.g., oral dosage form), and an additional amount of the lubricant makes up about 1% w/w of the pharmaceutical composition (e.g., oral dosage form), and are added extragranularly.

In some embodiments, the pharmaceutical composition (e.g., oral dosage form) comprises the following intragranularly added components: the solid dispersion comprising COMPOUND 1 and hypromellose acetate succinate (HPMCAS), makes up from about 50% w/w to about 70% w/w of the pharmaceutical composition (e.g., oral dosage form), microcrystalline cellulose makes up from about 18% w/w to about 26% w/w of the pharmaceutical composition (e.g., oral dosage form), croscarmellose sodium makes up from about 2% w/w to about 6% w/w of the pharmaceutical composition (e.g., oral dosage form), sodium lauryl sulfate makes up from about 0.5% w/w to about 1.5% w/w of the pharmaceutical composition (e.g., oral dosage form), colloidal silicon dioxide makes up from about 0.5% w/w to about 1.5% w/w of the pharmaceutical composition (e.g., oral dosage form), and magnesium stearate makes up from about 0.25% w/w to about 1% w/w of the pharmaceutical composition (e.g., oral dosage form).

In some embodiments, a the pharmaceutical composition (e.g., oral dosage form) comprises the following extragranularly added components: an additional amount of microcrystalline cellulose makes up from about 4% w/w to about 12% w/w of the pharmaceutical composition (e.g., oral dosage form), an additional amount of croscarmellose sodium makes up from about 1% w/w to about 3% w/w of the pharmaceutical composition (e.g., oral dosage form), an additional amount of colloidal silicon dioxide makes up from about 0.5% w/w to about 1.5% w/w of the pharmaceutical composition (e.g., oral dosage form), and an additional amount of magnesium stearate makes up from about 0.5% w/w to about 1.5% w/w of the pharmaceutical composition (e.g., oral dosage form), and are added extragranularly.

In some embodiments, the pharmaceutical composition (e.g., oral dosage form) comprises the following intragranularly added components: the solid dispersion comprising COMPOUND 1 and hypromellose acetate succinate (HPMCAS), makes up about 60% w/w of the pharmaceutical composition (e.g., oral dosage form), microcrystalline cellulose makes up about 21.5% w/w of the pharmaceutical composition (e.g., oral dosage form), croscarmellose sodium makes up about 4% w/w of the pharmaceutical composition (e.g., oral dosage form), sodium lauryl sulfate makes up about 1% w/w of the pharmaceutical composition (e.g., oral dosage form), colloidal silicon dioxide makes up about 1% w/w of the pharmaceutical composition (e.g., oral dosage form), and magnesium stearate makes up about 0.5% w/w of the pharmaceutical composition (e.g., oral dosage form).

In some embodiments, a the pharmaceutical composition (e.g., oral dosage form) comprises the following extragranularly added components: an additional amount of microcrystalline cellulose makes up about 8% w/w of the pharmaceutical composition (e.g., oral dosage form), an additional amount of croscarmellose sodium makes up about 2% w/w of the pharmaceutical composition (e.g., oral dosage form), an additional amount of colloidal silicon dioxide makes up about 1% w/w of the pharmaceutical composition (e.g., oral dosage form), and an additional amount of magnesium stearate makes up about 1% w/w of the pharmaceutical composition (e.g., oral dosage form), and are added extragranularly.

Methods of Use

In certain embodiments, the inhibitory activity of COMPOUND 1 against IDH1 mutants (e.g., IDH1 R132H, IDH1 R132C, IDH1 R132L, IDH1 R132V, IDH1 R132S or IDH1 R132GF) can be tested by methods described in Example A of PCT Publication No. WO 2013/107291 and US Publication No. US 2013/0190249, hereby incorporated by reference in their entireties, or analogous methods.

In one embodiment, provided herein is a method of treating malignancies by administering to a subject a mutant IDH1 inhibitor. In one embodiment, provided herein is a method for treating a hematologic malignancy by administering to a subject a mutant IDH1 inhibitor. In one embodiment, the hematologic malignancy is an advanced hematologic malignancy. In one embodiment the hematologic malignancy is relapsed or refractory In one embodiment, provided herein is a method of treating solid tumors by administering to a subject a mutant IDH1 inhibitor. In one embodiment the solid tumor is an advanced solid tumor. In one embodiment the solid tumor is a relapsed or refractory solid tumor.

In one embodiment, the mutant IDH1 inhibitor is COMPOUND 1.

In one embodiment, provided herein is a method of treating malignancies characterized by the presence of a mutant allele of IDH1, comprising administering to a subject a therapeutically effective amount of COMPOUND 1 with or without food wherein if COMPOUND 1 is administered with food, the food is not a high-fat meal.

In one embodiment, the malignancies are hematologic malignancies, such as acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma (e.g., T-cell lymphoma), each In one embodiment, the hematologic malignancy is an advanced hematologic malignancy. In one embodiment, the hematologic malignancy is relapsed or refractory. In one embodiment, the hematologic malignancy is relapsed or refractory acute myelogenous leukemia (AML).

In one embodiment, provided herein is a method of treating hematologic malignancies, such as acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1, comprising administering to a subject a therapeutically effective amount of COMPOUND 1, a crystalline form or a solid dispersion thereof, with or without food wherein if COMPOUND 1 is administered with food, the food is not a high-fat meal. In one embodiment, the hematologic malignancy is an advanced hematologic malignancy. In one embodiment, the hematologic malignancy is relapsed or refractory. In one embodiment, the hematologic malignancy is relapsed or refractory. In one embodiment, the hematologic malignancy is relapsed or refractory acute myelogenous leukemia (AML).

In one embodiment, provided herein is a method of treating hematologic malignancies, such as acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1, comprising administering to a subject a therapeutically effective amount of COMPOUND 1 with or without food wherein if COMPOUND 1 is administered with food, the food is not a high-fat meal. In one embodiment, the hematologic malignancy is an advanced hematologic malignancy. In one embodiment, the hematologic malignancy is relapsed or refractory. In one embodiment, the hematologic malignancy is relapsed or refractory. In one embodiment, the hematologic malignancy is relapsed or refractory acute myelogenous leukemia (AML).

In one embodiment, provided herein is a method of treating hematologic malignancies, such as acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1, comprising administering to a subject a therapeutically effective amount of COMPOUND 1 as part of a solid dispersion with or without food wherein if COMPOUND 1 is administered with food, the food is not a high-fat meal. In one embodiment, the hematologic malignancy is an advanced hematologic malignancy. In one embodiment, the hematologic malignancy is relapsed or refractory. In one embodiment, the hematologic malignancy is relapsed or refractory. In one embodiment, the hematologic malignancy is relapsed or refractory acute myelogenous leukemia (AML).

In one embodiment, provided herein is a methods of treating hematologic malignancies, such as acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1, comprising administering to a subject a therapeutically effective amount of a single crystalline form of COMPOUND 1 with or without food wherein if the single crystalline form of COMPOUND 1 is administered with food, the food is not a high-fat meal. In one embodiment, the single crystalline form of COMPOUND 1 is any percentage between 90% and 100% pure. In one embodiment, the hematologic malignancy is an advanced hematologic malignancy. In one embodiment, the hematologic malignancy is relapsed or refractory. In one embodiment, the hematologic malignancy is relapsed or refractory acute myelogenous leukemia (AML).

In one embodiment, provided herein is a method of treating hematologic malignancies, such as acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1, comprising administering to a subject a pharmaceutical composition comprising a therapeutically effective amount of COMPOUND 1 (e.g., an oral dosage form comprising a therapeutically effective amount of COMPOUND 1) with or without food wherein if the pharmaceutical composition (e.g., the oral dosage form) comprising COMPOUND 1 is administered with food, the food is not a high-fat meal. In one embodiment, the hematologic malignancy is an advanced hematologic malignancy. In one embodiment, the hematologic malignancy is relapsed or refractory. In one embodiment, the hematologic malignancy is relapsed or refractory. In one embodiment, the hematologic malignancy is relapsed or refractory acute myelogenous leukemia (AML).

In one embodiment, provided herein is a method of treating an hematologic malignancy, such as acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1, comprising administering to a subject a pharmaceutical composition comprising a therapeutically effective amount of a COMPOUND 1 as part of a solid dispersion (e.g., an oral dosage form comprising a therapeutically effective amount COMPOUND 1 as part of a solid dispersion) with or without food wherein if the pharmaceutical composition (e.g., oral dosage form) comprising COMPOUND 1 as part of a solid dispersion is administered with food, the food is not a high-fat meal. In one embodiment, the hematologic malignancy is an advanced hematologic malignancy. In one embodiment, the hematologic malignancy is relapsed or refractory. In one embodiment, the hematologic malignancy is relapsed or refractory. In one embodiment, the hematologic malignancy is relapsed or refractory acute myelogenous leukemia (AML).

In one embodiment, provided herein is a method of treating an hematologic malignancy, such as acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1, comprising administering to a subject a pharmaceutical composition comprising a therapeutically effective amount of a single crystalline form of COMPOUND 1 (e.g., an oral dosage form comprising a therapeutically effective amount of a single crystalline form of COMPOUND 1) with or without food wherein if the pharmaceutical composition (e.g., oral dosage form) comprising the single crystalline form of COMPOUND 1 is administered with food, the food is not a high-fat meal. In one embodiment, the single crystalline form of COMPOUND 1 is any percentage between 90% and 100% pure. In one embodiment, the hematologic malignancy is an advanced hematologic malignancy. In one embodiment, the hematologic malignancy is relapsed or refractory. In one embodiment, the hematologic malignancy is relapsed or refractory. In one embodiment, the hematologic malignancy is relapsed or refractory acute myelogenous leukemia (AML).

In one embodiment, provided herein is a method of treating a solid tumor, such as glioma, melanoma, chondrosarcoma, cholangiocarcinoma, sarcoma, or non-small cell lung cancer, each characterized by the presence of a mutant allele of IDH1, comprising administering to a subject a therapeutically effective amount of COMPOUND 1, a crystalline form or a solid dispersion thereof with or without food wherein if COMPOUND 1 is administered with food, the food is not a high-fat meal. In one embodiment, the solid tumor is an advanced solid tumor. In one embodiment, the solid is relapsed or refractory.

In one embodiment, provided herein is a method of treating a solid tumor, such as glioma, melanoma, chondrosarcoma, cholangiocarcinoma, sarcoma, or non-small cell lung cancer, each characterized by the presence of a mutant allele of IDH1, comprising administering to a subject a therapeutically effective amount of COMPOUND 1 with or without food wherein if COMPOUND 1 is administered with food, the food is not a high-fat meal. In one embodiment, the solid tumor is an advanced solid tumor. In one embodiment, the solid is relapsed or refractory.

In one embodiment, provided herein is a method of treating a solid tumor, such as glioma, melanoma, chondrosarcoma, cholangiocarcinoma (including intrahepatic cholangiocarcinoma (IHCC), prostate cancer, colon cancer, or non-small cell lung cancer (NSCLC), each characterized by the presence of a mutant allele of IDH1, comprising administering to a subject a therapeutically effective amount of COMPOUND 1 as part of a solid dispersion with or without food wherein if COMPOUND 1 as part of a solid dispersion is administered with food, the food is not a high-fat meal. In one embodiment, the solid tumor is an advanced solid tumor. In one embodiment, the solid is relapsed or refractory.

In one embodiment, provided herein is a methods of treating a solid tumor, such as glioma, melanoma, chondrosarcoma, cholangiocarcinoma (including intrahepatic cholangiocarcinoma (IHCC), prostate cancer, colon cancer, or non-small cell lung cancer (NSCLC), each characterized by the presence of a mutant allele of IDH1, comprising administering to a subject a therapeutically effective amount of a single crystalline form of COMPOUND 1 with or without food wherein if the single crystalline form of COMPOUND 1 is administered with food, the food is not a high-fat meal. In one embodiment, the single crystalline form of COMPOUND 1 is any percentage between 90% and 100% pure. In one embodiment, the solid tumor is an advanced solid tumor. In one embodiment, the solid is relapsed or refractory.

In one embodiment, provided herein is a method of treating a solid tumor, such as glioma, melanoma, chondrosarcoma, cholangiocarcinoma (including intrahepatic cholangiocarcinoma (IHCC), prostate cancer, colon cancer, or non-small cell lung cancer (NSCLC), each characterized by the presence of a mutant allele of IDH1, comprising administering to a subject a pharmaceutical composition comprising a therapeutically effective amount of COMPOUND 1 (e.g., an oral dosage form comprising a therapeutically effective amount of COMPOUND 1) with or without food wherein if the pharmaceutical composition (e.g., oral dosage form) of COMPOUND 1 is administered with food, the food is not a high-fat meal. In one embodiment, the solid tumor is an advanced solid tumor. In one embodiment, the solid is relapsed or refractory.

In one embodiment, provided herein is a method of treating a solid tumor, such as glioma, melanoma, chondrosarcoma, cholangiocarcinoma (including intrahepatic cholangiocarcinoma (IHCC), prostate cancer, colon cancer, or non-small cell lung cancer (NSCLC), each characterized by the presence of a mutant allele of IDH1, comprising administering to a subject a pharmaceutical composition comprising a therapeutically effective amount of COMPOUND 1 as part of a solid dispersion (e.g., an oral dosage form comprising a therapeutically effective amount of COMPOUND 1 as part of a solid dispersion) with or without food wherein if the pharmaceutical composition (e.g., oral dosage form) comprising the single crystalline form of COMPOUND 1 is administered with food, the food is not a high-fat meal. In one embodiment, the solid tumor is an advanced solid tumor. In one embodiment, the solid is relapsed or refractory.

In one embodiment, provided herein is a method of treating a solid tumor, such as glioma, melanoma, chondrosarcoma, cholangiocarcinoma (including intrahepatic cholangiocarcinoma (IHCC), prostate cancer, colon cancer, or non-small cell lung cancer (NSCLC), each characterized by the presence of a mutant allele of IDH1, comprising administering to a subject a pharmaceutical composition comprising a therapeutically effective amount of a single crystalline form of COMPOUND 1 (e.g., an oral dosage form comprising a therapeutically effective amount of a single crystalline form of COMPOUND 1) with or without food wherein if the pharmaceutical composition (e.g., oral dosage form) comprising the single crystalline form of COMPOUND 1 is administered with food, the food is not a high-fat meal. In one embodiment, the single crystalline form of COMPOUND 1 is any percentage between 90% and 100% pure. In one embodiment, the solid tumor is an advanced solid tumor. In one embodiment, the solid is relapsed or refractory.

In one embodiment, the malignancy to be treated is characterized by a mutant allele of IDH1, wherein the IDH1 mutation results in a new ability of the enzyme to catalyze the NADPH dependent reduction of a ketoglutarate to R( ) 2 hydroxyglutarate in a patient. In one aspect of this embodiment, the mutant IDH1 has an R132X mutation. In one aspect of this embodiment, the R132X mutation is selected from R132H, R132C, R132L, R132V, R132S and R132G. In another aspect, the R132X mutation is R132H or R132C. In yet another aspect, the R132X mutation is R132H.

A malignancy can be analyzed by sequencing cell samples to determine the presence and specific nature of (e.g., the changed amino acid present at) a mutation at amino acid 132 of IDH1.

Without being bound by theory, applicants believe that mutant alleles of IDH1 wherein the IDH1 mutation results in a new ability of the enzyme to catalyze the NADPH-dependent reduction of α-ketoglutarate to R(−)-2-hydroxyglutarate, and in particular R132H mutations of IDH1, characterize a subset of all types of cancers, without regard to their cellular nature or location in the body. Thus, the compounds, and methods described herein are useful to treat an hematologic malignancy, including an advanced hematologic malignancy, such as acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1 imparting such activity and in particular an IDH1 R132H or R132C mutation. In another aspect, the compounds, and methods described herein are useful to treat a solid tumor, such as glioma, melanoma, chondrosarcoma, cholangiocarcinoma (including intrahepatic cholangiocarcinoma (IHCC), prostate cancer, colon cancer, or non-small cell lung cancer (NSCLC), each characterized by the presence of a mutant allele of IDH1 imparting such activity and in particular an IDH1 R132H or R132C mutation.

In one embodiment the malignancy is a tumor wherein at least 30, 40, 50, 60, 70, 80 or 90% of the tumor cells carry an IDH1 mutation, and in particular an IDH1 R132H or R132C mutation, at the time of diagnosis or treatment.

In one embodiment, the efficacy of treatment of malignancy is monitored by measuring the levels of 2HG in the subject. Typically levels of 2HG are measured prior to treatment, wherein an elevated level is indicated for the use of COMPOUND 1. Once the elevated levels are established, the level of 2HG is determined during the course of and/or following termination of treatment to establish efficacy. In certain embodiments, the level of 2HG is only determined during the course of and/or following termination of treatment. A reduction of 2HG levels during the course of treatment and following treatment is indicative of efficacy. Similarly, a determination that 2HG levels are not elevated during the course of or following treatment is also indicative of efficacy. Typically, 2HG measurements are utilized together with other well-known determinations of efficacy of malignancy treatment, such as reduction in number and size of tumors and/or other cancer-associated lesions, improvement in the general health of the subject, and alterations in other biomarkers that are associated with malignancy treatment efficacy.

2HG can be detected in a sample by the methods of PCT Publication No. WO 2011/050210 and US Publication No. US2012/0121515 hereby incorporated by reference in their entirety, or by analogous methods. In an exemplary method, 2HG can be detected in a sample by LC/MS. The sample is mixed 80:20 with methanol, and centrifuged at 3,000 rpm for 20 minutes at 4 degrees Celsius. The resulting supernatant can be collected and stored at −80 degrees Celsius prior to LC-MS/MS to assess 2-hydroxyglutarate levels. A variety of different liquid chromatography (LC) separation methods can be used. Each method can be coupled by negative electrospray ionization (ESI, −3.0 kV) to triple-quadrupole mass spectrometers operating in multiple reaction monitoring (MRM) mode, with MS parameters optimized on infused metabolite standard solutions. Metabolites can be separated by reversed phase chromatography using 10 mM tributyl-amine as an ion pairing agent in the aqueous mobile phase, according to a variant of a previously reported method (Luo et al. *J Chromatogr A* 1147, 153-64, 2007). One method allows resolution of TCA metabolites: t=0, 50% B; t=5, 95% B; t=7, 95% B; t=8, 0% B, where B refers to an organic mobile phase of 100% methanol. Another method is specific for 2-hydroxyglutarate, running a fast linear gradient from 50%-95% B (buffers as defined above) over 5 minutes. A Synergi Hydro-RP, 100 mm×2 mm, 2.1 μm particle size (Phenomonex) can be used as the column, as described above. Metabolites can be quantified by comparison of peak areas with pure metabolite standards at known concentration. Metabolite flux studies from $^{13}$C-glutamine can be performed as described, e.g., in Munger et al. Nat Biotechnol 26, 1179-86, 2008.

In one embodiment, 2HG is directly evaluated.

In another embodiment, a derivative of 2HG formed in process of performing the analytic method is evaluated. By way of example such a derivative can be a derivative formed in MS analysis. Derivatives can include a salt adduct, e.g., a Na adduct, a hydration variant, or a hydration variant which is also a salt adduct, e.g., a Na adduct, e.g., as formed in MS analysis.

In another embodiment a metabolic derivative of 2HG is evaluated. Examples include species that build up or are elevated, or reduced, as a result of the presence of 2HG, such as glutarate or glutamate that will be correlated to 2HG, e.g., R-2HG.

Exemplary 2HG derivatives include dehydrated derivatives such as the compounds provided below or a salt adduct thereof:

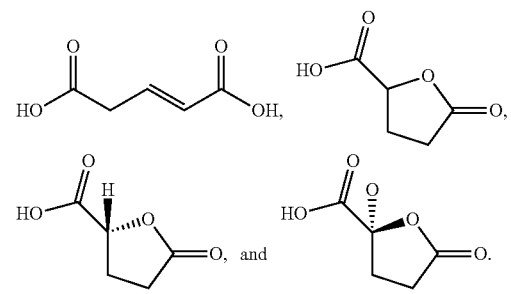

2HG is known to accumulate in the inherited metabolic disorder 2-hydroxyglutaric aciduria. This disease is caused by deficiency in the enzyme 2-hydroxyglutarate dehydrogenase, which converts 2HG to α-KG (Struys, E. A. et al. Am J Hum Genet 76, 358-60 (2005)). Patients with 2-hydroxyglutarate dehydrogenase deficiencies accumulate 2HG in the brain as assessed by MRI and CSF analysis, develop leukoencephalopathy, and have an increased risk of developing brain tumors (Aghili, M., Zahedi, F. & Rafiee, *J Neurooncol* 91, 233-6 (2009); Kolker, S., Mayatepek, E. & Hoffmann, G. F. *Neuropediatrics* 33, 225-31 (2002); Wajner, M., Latini, A., Wyse, A. T. & Dutra-Filho, C. S. *J Inherit Metab Dis* 27, 427-48 (2004)). Furthermore, elevated brain levels of 2HG result in increased ROS levels (Kolker, S. et al. *Eur J Neurosci* 16, 21-8 (2002); Latini, A. et al. *Eur J Neurosci* 17, 2017-22 (2003)), potentially contributing to an increased risk of cancer. The ability of 2HG to act as an NMDA receptor agonist may contribute to this effect (Kolker, S. et al. *Eur J Neurosci* 16, 21-8 (2002)). 2HG may also be toxic to cells by competitively inhibiting glutamate and/or αKG utilizing enzymes. These include transaminases which allow utilization of glutamate nitrogen for amino and nucleic acid biosynthesis, and αKG-dependent prolyl hydroxylases such as those which regulate Hif1-alpha levels.

Thus, according to another embodiment, provided herein is a method of treating 2-hydroxyglutaric aciduria, particularly D-2-hydroxyglutaric aciduria, in a subject by administering to the subject COMPOUND 1.

Treatment methods described herein can additionally comprise various evaluation steps prior to and/or following treatment with COMPOUND 1.

In one embodiment, prior to and/or after treatment with COMPOUND 1 the method further comprises the step of evaluating the growth, size, weight, invasiveness, stage and/or other phenotype of the malignancy.

In one embodiment, prior to and/or after treatment with COMPOUND, the method further comprises the step of evaluating the IDH1 genotype of the malignancy. This may be achieved by ordinary methods in the art, such as DNA sequencing, immuno analysis, and/or evaluation of the presence, distribution or level of 2HG.

In one embodiment, prior to and/or after treatment with COMPOUND 1, the method further comprises the step of determining the 2HG level in the subject. This may be achieved by spectroscopic analysis, e.g., magnetic resonance-based analysis, e.g., MRI and/or MRS measurement, sample analysis of bodily fluid, such as serum or spinal cord fluid analysis, or by analysis of surgical material, e.g., by mass-spectroscopy.

In one embodiment, depending on the disease to be treated and the subject's condition, COMPOUND 1 may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. COMPOUND 1 may be formulated alone or together with one or more active agent(s), in suitable dosage unit with pharmaceutically acceptable excipients, carriers, adjuvants and vehicles, appropriate for each route of administration.

In one embodiment, the amount of COMPOUND 1 administered in the methods provided herein may range, e.g., between about 5 mg/day and about 2,000 mg/day. In one embodiment, the range is between about 10 mg/day and about 2,000 mg/day. In one embodiment, the range is between about 20 mg/day and about 2,000 mg/day. In one embodiment, the range is between about 50 mg/day and about 1,000 mg/day. In one embodiment, the range is between about 100 mg/day and about 1,000 mg/day. In one embodiment, the range is between about 100 mg/day and about 500 mg/day. In one embodiment, the range is between about 150 mg/day and about 500 mg/day. In one embodiment, the range is or between about 150 mg/day and about 250 mg/day. In certain embodiments, particular dosages are, e.g., about 10 mg/day. In one embodiment, the dose is about 20 mg/day. In one embodiment, the dose is about 50 mg/day. In one embodiment, the dose is about 75 mg/day. In one embodiment, the dose is about 100 mg/day. In one embodiment, the dose is about 120 mg/day. In one embodiment, the dose is about 150 mg/day. In one embodiment, the dose is about 200 mg/day. In one embodiment, the dose is about 250 mg/day. In one embodiment, the dose is about 300 mg/day. In one embodiment, the dose is about 350 mg/day. In one embodiment, the dose is about 400 mg/day. In one embodiment, the dose is about 450 mg/day. In one embodiment, the dose is about 500 mg/day. In one embodiment, the dose is about 600 mg/day. In one embodiment, the dose is about 700 mg/day. In one embodiment, the dose is about 800 mg/day. In one embodiment, the dose is about 900 mg/day. In one embodiment, the dose is about 1,000 mg/day. In one embodiment, the dose is about 1,200 mg/day. In one embodiment, the dose is or about 1,500 mg/day. In certain embodiments, particular dosages are, e.g., up to about 10 mg/day. In one embodiment, the particular dose is up to about 20 mg/day. In one embodiment, the particular dose is up to about 50 mg/day. In one embodiment, the particular dose is up to about 75 mg/day. In one embodiment, the particular dose is up to about 100 mg/day. In one embodiment, the particular dose is up to about 120 mg/day. In one embodiment, the particular dose is up to about 150 mg/day. In one embodiment, the particular dose is up to about 200 mg/day. In one embodiment, the particular dose is up to about 250 mg/day. In one embodiment, the particular dose is up to about 300 mg/day. In one embodiment, the particular dose is up to about 350 mg/day. In one embodiment, the particular dose is up to about 400 mg/day. In one embodiment, the particular dose is up to about 450 mg/day. In one embodiment, the particular dose is up to about 500 mg/day. In one embodiment, the particular dose is up to about 600 mg/day. In one embodiment, the particular dose is up to about 700 mg/day. In one embodiment, the particular dose is up to about 800 mg/day. In one embodiment, the particular dose is up to about 900 mg/day. In one embodiment, the particular dose is up to about 1,000 mg/day. In one embodiment, the particular dose is up to about 1,200 mg/day. In one embodiment, the particular dose is up to about 1,500 mg/day.

In one embodiment, the amount of COMPOUND 1 in the pharmaceutical composition or dosage form (e.g., oral dosage form) provided herein may range, e.g., between about 5 mg and about 2,000 mg. In one embodiment, the range is between about 10 mg and about 2,000 mg. In one embodiment, the range is between about 20 mg and about 2,000 mg. In one embodiment, the range is between about 50 mg and about 1,000 mg. In one embodiment, the range is between about 50 mg and about 500 mg. In one embodiment, the range is between about 50 mg and about 250 mg. In one embodiment, the range is between about 100 mg and about 500 mg. In one embodiment, the range is between about 150 mg and about 500 mg. In one embodiment, the range is between about 150 mg and about 250 mg. In certain embodiments, particular amounts are, e.g., about 10 mg. In one embodiment, the particular amount is about 20 mg. In one embodiment, the particular amount is about 50 mg. In one embodiment, the particular amount is about 75 mg. In one embodiment, the particular amount is about 100 mg. In one embodiment, the particular amount is about 120 mg. In one embodiment the particular amount is about 125 mg. In one embodiment, the particular amount is about 150 mg. In one embodiment, the particular amount is about 200 mg. In one embodiment, the particular amount is about 250 mg. In one embodiment, the particular amount is about 300 mg. In one embodiment, the particular amount is about 350 mg. In one embodiment, the particular amount is about 400 mg. In one embodiment, the particular amount is about 450 mg. In one embodiment, the particular amount is about 500 mg. In one embodiment, the particular amount is about 600 mg. In one embodiment, the particular amount is about 700 mg. In one embodiment, the particular amount is about 800 mg. In one embodiment, the particular amount is about 900 mg. In one embodiment, the particular amount is about 1,000 mg. In one embodiment, the particular amount is about 1,200 mg. In one embodiment, the particular amount is or about 1,500 mg. In certain embodiments, particular amounts are, e.g., up to about 10 mg. In one embodiment, the particular amount is up to about 20 mg. In one embodiment, the particular amount is up to about 50 mg. In one embodiment, the particular amount is up to about 75 mg. In one embodiment, the particular amount is up to about 100 mg. In one embodiment, the particular amount is up to about 120 mg. In one embodiment, the particular amount is up to about 150 mg. In one embodiment, the particular amount is up to about 200 mg. In one embodiment, the particular amount is up to about 250 mg. In one embodiment, the particular amount is up to about 300 mg. In one embodiment, the particular amount is up to about 350 mg. In one embodiment, the particular amount is up to about 400 mg. In one embodiment, the particular amount is up to about 450 mg. In one embodiment, the particular amount is up to about 500 mg. In one embodiment, the particular amount is up to about 600 mg. In one embodiment, the particular amount is up to about 700 mg. In one embodiment, the particular amount is up to about 800 mg. In one embodiment, the particular amount is up to about 900 mg. In one embodiment, the particular amount is up to about 1,000 mg. In one embodiment, the particular amount is up to about 1,200 mg. In one embodiment, the particular amount is up to about 1,500 mg.

In one embodiment, COMPOUND 1 can be delivered as a single dose such as, e.g., a single bolus injection, or oral tablets or pills; or over time such as, e.g., continuous infusion over time or divided bolus doses over time. In one embodiment, COMPOUND 1 can be administered repetitively if necessary, for example, until the patient experiences stable disease or regression, or until the patient experiences disease progression or unacceptable toxicity. Stable disease or lack thereof is determined by methods known in the art such as evaluation of patient's symptoms, physical examination, visualization of the tumor that has been imaged using X-ray, CAT, PET, or MRI scan and other commonly accepted evaluation modalities.

In certain embodiments, COMPOUND 1 is administered to a patient in cycles (e.g., daily administration for one week, then a rest period with no administration for up to three weeks). Cycling therapy involves the administration of an active agent for a period of time, followed by a rest for a period of time, and repeating this sequential administration. Cycling therapy can reduce the development of resistance, avoid or reduce the side effects, and/or improves the efficacy of the treatment.

In one embodiment, a method provided herein comprises administering COMPOUND 1 in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or greater than 40 cycles. In one embodiment, the median number of cycles administered in a group of patients is about 1. In one embodiment, the median number of cycles administered in a group of patients is about 2. In one embodiment, the median number of cycles administered in a group of patients is about 3. In one embodiment, the median number of cycles administered in a group of patients is about 4. In one embodiment, the median number of cycles administered in a group of patients is about 5. In one embodiment, the median number of cycles administered in a group of patients is about 6. In one embodiment, the median number of cycles administered in a group of patients is about 7. In one embodiment, the median number of cycles administered in a group of patients is about 8. In one embodiment, the median number of cycles administered in a group of patients is about 9. In one embodiment, the median number of cycles administered in a group of patients is about 10. In one embodiment, the median number of cycles administered in a group of patients is about 11. In one embodiment, the median number of cycles administered in a group of patients is about 12. In one embodiment, the median number of cycles administered in a group of patients is about 13. In one embodiment, the median number of cycles administered in a group of patients is about 14. In one embodiment, the median number of cycles administered in a group of patients is about 15. In one embodiment, the median number of cycles administered in a group of patients is about 16. In one embodiment, the median number of cycles administered in a group of patients is about 17. In one embodiment, the median number of cycles administered in a group of patients is about 18. In one embodiment, the median number of cycles administered in a group of patients is about 19. In one embodiment, the median number of cycles administered in a group of patients is about 20. In one embodiment, the median number of cycles administered in a group of patients is about 21. In one embodiment, the median number of cycles administered in a group of patients is about 22. In one embodiment, the median number of cycles administered in a group of patients is about 23. In one embodiment, the median number of cycles administered in a group of patients is about 24. In one embodiment, the median number of cycles administered in a group of patients is about 25. In one embodiment, the median number of cycles administered in a group of patients is about 26. In one embodiment, the median number of cycles administered in a group of patients is about 27. In one embodiment, the median number of cycles administered in a group of patients is about 28. In one embodiment, the median number of cycles administered in a group of patients is about 29. In one embodiment, the median number of cycles administered in a group of patients is about 30. In one embodiment, the median number of cycles administered in a group of patients is greater than about 30 cycles.

In certain embodiments, treatment cycles comprise multiple doses of COMPOUND 1 administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days).

In one embodiment, COMPOUND 1 is administered orally once a day. In one embodiment, COMPOUND 1 is administered on days 1-28 of each 28-day cycle. In one embodiment, 50 mg of COMPOUND 1 is administered orally once a day. In another embodiment, 100 mg of COMPOUND 1 is administered orally once a day. In yet another embodiment, 200 mg of COMPOUND 1 is administered orally once a day. In yet another embodiment, 250 mg of COMPOUND 1 is administered orally once a day. In yet another embodiment, 500 mg of COMPOUND 1 is administered orally once a day. In one embodiment 500 mg of COMPOUND 1 (e.g., an oral dosage form comprising 500 mg of COMPOUND 1) is administered orally once a day as a single dosage form unit (e.g., tablet) comprising 500 mg of COMPOUND 1. In one embodiment, 500 mg of COMPOUND 1 (e.g., an oral dosage form comprising 500 mg of COMPOUND 1) is administered orally once a day as a two dosage form units (e.g., tablets) comprising 250 mg of COMPOUND 1 each. In one embodiment, 500 mg of COMPOUND 1 (e.g., an oral dosage form comprising 500 mg of COMPOUND 1) is administered orally once a day as a four dosage form units (e.g., tablets) comprising 125 mg of COMPOUND 1 each. In one embodiment, 500 mg of COMPOUND 1 (e.g., an oral dosage form comprising 500 mg of COMPOUND 1) is administered orally once a day as a five dosage form units (e.g., tablets) comprising 100 mg of COMPOUND 1 each. In one embodiment a method provided herein comprises orally administering to the subject a pharmaceutical formulation (e.g., an immediate release oral formulation, e.g., an oral dosage form) that achieves an AUC value (e.g., $AUC_{0-t}$ or $AUC_{0-\infty}$) between 110000 hr-ng/mL and 165000 hr-ng/mL, preferably between 120000 hr-ng/mL and 155000 hr-ng/mL in the subject to which the formulation is orally administered. In an embodiment the AUC value is obtained when the pharmaceutical formulation is administered to a subject with or without food, avoiding administration with a high-fat meal. In one embodiment, a method provided herein comprises orally administering to the subject a pharmaceutical formulation (e.g., an immediate release oral formulation, e.g., an oral dosage form) comprising 500 mg COMPOUND 1 that achieves an AUC value (e.g., $AUC_{0-t}$ or $AUC_{0-\infty}$) between 110000 hr-ng/mL and 165000 hr-ng/mL, preferably between 120000 hr-ng/mL and 155000 hr-ng/mL in the subject to which the formulation is orally administered. In an embodiment the AUC value is obtained when the pharmaceutical formulation is administered to a subject with or without food, avoiding administration with a high-fat meal. In an embodiment the formulation is administered in a single unit dosage form (e.g., tablet, capsule) comprising 500 mg COMPOUND 1. In an embodiment the formulation is administered in 2 unit dosage forms (e.g., tablets, capsules) comprising 250 mg COMPOUND 1 each. In another embodiment the formulation is administered in 4 unit dosage forms (e.g., tablets, capsules) comprising 125 mg COMPOUND 1 each. In another embodiment the formulation is administered in 5 unit dosage forms (e.g., tablets, capsules) comprising 100 mg COMPOUND 1 each.

In one embodiment a method provided herein comprises orally administering to the subject a pharmaceutical formulation (e.g., an immediate release oral formulation, e.g., an oral dosage form) that achieves a $C_{max}$ of COMPOUND 1 between 1500 ng/mL and 3100 ng/mL, preferably between 1800 ng/mL and 2800 ng/mL in the subject to which the formulation is orally administered. In an embodiment the $C_{max}$ value is obtained when the pharmaceutical formulation is administered to a subject with or without food, avoiding administration with a high-fat meal. In one embodiment, a method provided herein comprises orally administering to the subject a pharmaceutical formulation (e.g., an immediate release oral formulation, e.g., an oral dosage form) comprising 500 mg COMPOUND 1 that achieves a $C_{max}$ of COMPOUND 1 between 1500 ng/mL and 3100 ng/mL, preferably between 1800 ng/mL and 2800 ng/mL in the subject to which the formulation is orally administered. In an embodiment the $C_{max}$ value is obtained when the pharmaceutical formulation is administered to a subject with or without food, avoiding administration with a high-fat meal. In an embodiment the formulation is administered in a single unit dosage form (e.g., tablet, capsule) comprising 500 mg COMPOUND 1. In an embodiment the formulation is administered in 2 unit dosage forms (e.g., tablets, capsules) comprising 250 mg COMPOUND 1 each. In another embodiment the formulation is administered in 4 unit dosage forms (e.g., tablets, capsules) comprising 125 mg COMPOUND 1 each. In another embodiment the formulation is administered in 5 unit dosage forms (e.g., tablets, capsules) comprising 100 mg COMPOUND 1 each.

Bioavailability and Food

Food can change the bioavailability of a drug or compound and can have clinically significant consequences. Food can alter bioavailability in an unpredictable manner by various means, including delay gastric emptying, stimulate bile flow, change gastrointestinal (GI) pH, increase splanchnic blood flow, change luminal metabolism of a drug substance, and/or physically and chemically interact with a dosage form or a drug substance. The nutrient and caloric contents of the meal, the meal volume, and the meal temperature can cause physiological changes in the GI tract in a way that affects drug product transit time, luminal dissolution, drug permeability, and systemic availability. Administration of a drug or compound with food may change the bioavailability by affecting either the drug substance or the drug product. It is difficult to determine the mechanism by which food changes the bioavailability of a drug or compound.

The disclosure provides a method of controlling the extent of absorption of COMPOUND 1 as measured by the concentration attained in the blood stream over time in a subject in need of a therapeutic effect thereof. This method comprises orally administering to a subject a therapeutically effective amount of COMPOUND 1 with or without food wherein if COMPOUND 1 is administered with food, the food is not a high-fat meal. The concentration in the blood stream is measured as the plasma concentration (e.g., ng/mL) of COMPOUND 1. Pharmacokinetic parameters involved in determining the plasma concentration include the maximum observed plasma concentration ($C_{max}$), area under the plasma concentration time curve (AUC) from time zero up to the last quantifiable concentration ($AUC_{0-t}$), and AUC from time zero to infinity ($AUC_{0-\infty}$). Administering COMPOUND 1 to a subject with a high-fat meal increases the bioavailability as measured by increased values of one or more of the aforesaid pharmacokinetic parameters, when compared to administration of the drug under fasted (or without food) conditions. In some embodiments, the AUC (e.g., $AUC_{0-t}$, $AUC_{0-\infty}$) value for the formulation of COMPOUND 1 in a tablet administered with a high-fat meal has a percent increase of at least 10% or greater when compared to the AUC (e.g., $AUC_{0-t}$, $AUC_{0-\infty}$) value for the formulation of COMPOUND 1 in a tablet administered without food. In other embodiments, this percent increase is at least 20% or greater; is at least 30% or greater; is at least 40% or greater; is at least 50% or greater is at least 60% or greater; is at least 70% or greater; is at least 80% or greater; is at least 90% or greater, is at least 100% or greater. In some embodiments, this percent increase is between about 50-150%. In some embodiments, this percent increase is between about 70-140%. In some embodiments, this percent increase is between about 80-120%. In some embodiments, this percent increase is between about 90-110%. In some embodiments, this increase is about 100% (e.g., about 98%). In some embodiments, the $C_{max}$ value for the formulation of COMPOUND 1 in a tablet administered with a high-fat meal has a percent increase of at least 10% or greater when compared to the $C_{max}$ value for the formulation of COMPOUND 1 in a tablet administered without food. In some embodiments, this percent increase is at least 15% or greater. In some embodiments, this percent increase is at least 20% or greater.

In some embodiments, this percent increase is at least 20% or greater. In some embodiments this percent increase is at least 25% or greater. In some embodiments this percent increase is between 15-35%. In some embodiments this percent increase is between 20-30%. In some embodiments this percent increase is about 25%.

A high-fat meal may comprise about 50 percent of the total caloric content of the meal as fat and about 900 to 1000 calories. An exemplary high-fat meal includes the test meal disclosed in the document Guidance for Industry, Food-Effect Bioavailability and Fed Bioequivalence Studies, U.S. Department of Health and Human Services Food and Drug Administration, Center for Drug Evaluation and Research (CDER), Center for Biologics Evaluation and Research (CBER) issued December 2002. The exemplary high-fat meal contains approximately 50 percent of the total caloric content of the meal as fat and contains approximately 900 to 1000 calories; 500-600 calories from fat. As used herein, the term "fat" is used in its conventional, art-recognized meaning. For example, a high-fat meal may be two eggs fried in butter, two strips of bacon, two slices of toast with butter, 4 oz. of hash brown potatoes and 8 oz. of whole milk. A regular meal or a standard meal may be a meal such as breakfast, lunch or dinner having calories of 300 to 800 calories. Methods of the disclosure include administering a therapeutically effective amount of COMPOUND 1 substantially contemporaneously with food, wherein the food may be a snack, or less than a meal provided that the meal is not a high-fat meal. For example, COMPOUND 1 may be administered substantially contemporaneously with food, where the food contains about 50 calories. Additionally, COMPOUND 1 may be administered substantially contemporaneously with food, where the food contains about 100 calories. COMPOUND 1 may be administered substantially contemporaneously with food, where the food contains about 200 or about 300 calories. For example, a subject could ingest a food (e.g., snack) such as fruit, granola, crackers, cheese, etc., and then the subject would take (ingest) a therapeutically effective amount of COMPOUND 1.

In another aspect of the disclosure, a subject is administered a therapeutically effective amount of COMPOUND 1 substantially contemporaneously with food (e.g., regular meal, or food containing about 50 to about 300 calories, as discussed herein), where substantially contemporaneously with food means administering the therapeutically effective amount of COMPOUND 1 within 5, 10, 15, 30, 45, 60, 75, or 90 minutes before or after ingesting or eating the food, provided that the food is not a high-fat meal. For example, administering a therapeutically effective amount of COMPOUND 1 within approximately 90 minutes before or after ingesting or eating the food which is not a high-fat meal (e.g., regular meal, or food containing about 50 to about 300 calories, as discussed herein). For example, administering a therapeutically effective amount of COMPOUND 1 within approximately 75 minutes before or after ingesting or eating the food which is not a high-fat meal (e.g., regular meal, or food containing about 50 to about 300 calories, as discussed herein). For example, administering a therapeutically effective amount of COMPOUND 1 within approximately 60 minutes before or after ingesting or eating the food which is not a high-fat meal (e.g., regular meal, or food containing about 50 to about 300 calories, as discussed herein). For example, administering a therapeutically effective amount of COMPOUND 1 within approximately 45 minutes before or after ingesting or eating the food which is not a high-fat meal (e.g., regular meal, or food containing about 50 to about 300 calories, as discussed herein). For example, administering a therapeutically effective amount of COMPOUND 1 within approximately 30 minutes before or after ingesting or eating the food which is not a high-fat meal (e.g., regular meal, or food containing about 50 to about 300 calories, as discussed herein). For example, administering a therapeutically effective amount of COMPOUND 1 within approximately 15 minutes before or after ingesting or eating the food which is not a high-fat meal (e.g., regular meal, or food containing about 50 to about 300 calories, as discussed herein). For example, administering a therapeutically effective amount of COMPOUND 1 within approximately 10 minutes before or after ingesting or eating the food which is not a high-fat meal (e.g., regular meal, or food containing about 50 to about 300 calories, as discussed herein). For example, administering a therapeutically effective amount of COMPOUND 1 within approximately 5 minutes before or after ingesting or eating the food (e.g., regular meal, or food containing about 50 to about 300 calories, as discussed herein).

COMPOUND 1 may be administered any time of day without food. In some embodiments, the therapeutically effective amount of the oral dosage form is administered at least 60 minutes before ingesting food. In some embodiments, the therapeutically effective amount of the oral dosage form is administered at least 90 minutes before ingesting food. In some embodiments, the therapeutically effective amount of the oral dosage form is administered at least 120 minutes before ingesting food. In some embodiments, the therapeutically effective amount of the oral dosage form is administered at least 180 minutes before ingesting food. In further embodiments, the therapeutically effective amount of the oral dosage form is administered at least 60 minutes after ingesting food. In some embodiments, the therapeutically effective amount of the oral dosage form is administered at least 90 minutes after ingesting food. In some embodiments, the therapeutically effective amount of the oral dosage form is administered at least 120 minutes after ingesting food. In some embodiments, the therapeutically effective amount of the oral dosage form is administered at least 180 minutes after ingesting food.

The increased bioavailability of COMPOUND 1 to a subject receiving COMPOUND 1 can be evidenced in any suitable manner. For example, oral administration of COMPOUND 1 with a high-fat meal results in an increased bioavailability of COMPOUND 1 as evidenced by an increase in the AUC (e.g., $AUC_{0-t}$, $AUC_{0-\infty}$) value of COMPOUND 1 as compared to the AUC (e.g., $AUC_{0-t}$, $AUC_{0-\infty}$) value of COMPOUND 1 without food.

Articles of Manufacture

Compositions of the disclosure may also be packaged as articles of manufacture comprising a therapeutically effective amount of COMPOUND 1. Any of the various methods known by persons skilled in the art for packaging tablets, caplets, or other solid dosage forms suitable for oral administration, that will not degrade the components of the present disclosure, are suitable for use in packaging.

In some aspects, an article of manufacture comprises a therapeutically effective amount of COMPOUND 1, packaging material, and a label affixed to or printed on the packaging material. In some aspects, an article of manufacture comprises a therapeutically effective amount of COMPOUND 1, packaging material, and a package insert contained within the packaging material.

In some embodiments, the packaging material comprises at least one container. In some embodiments, the packaging material comprises multiple containers. As used herein, a container is an object that holds the therapeutically effective amount of COMPOUND 1. For example, the container may be a bottle, a blister pack, a box, a carton, a strip package, a cartridge, or a single-dose container. In some embodiments, the container is a bottle that holds a therapeutically effective amount of COMPOUND 1. In some embodiments, a box contains the bottle that holds the therapeutically effective amount of COMPOUND 1. In some embodiments, the container is a blister pack that holds the therapeutically effective amount of COMPOUND 1.

It should be appreciated that the packaging material may comprise a single material or various materials. For example, the packaging material may be comprised of glass, paper, plastic or metal materials. In some embodiments, the packaging material is composed of glass, plastic and metal materials. In some embodiments, the packaging material is composed of glass and plastic. In some embodiments, the packaging material is composed of glass and metal materials. In some embodiments, the packaging material is composed of plastic and metal materials. In some embodiments, the packaging material is composed of glass materials. For example, the packaging material is a glass bottle. In some embodiments, the packaging material is composed of plastic materials. For example, the packaging material is a plastic bottle or a plastic blister pack. In some embodiments, the packaging material is composed of metal materials. For example, the packaging material is a metal (e.g., aluminum) blister pack.

In some embodiments, the container has a closure. Closures are used for the purpose of covering drug containers after filling the container with solid dosage forms comprising COMPOUND 1. Depending on the type of container, closures may have different shapes and sizes. A closure may be rubber, may be a cap or overseal, may be a tamper-evident closure, may be a child-resistant closure, etc. A packaging material of the disclosure may have one, two, three, four or five types of closure. For example, if the container is a glass bottle, the glass bottle may have a rubber seal and a plastic cap.

The packaging material may also have labelling and information related to the pharmaceutical composition printed thereon. Additionally, an article of manufacture may contain a brochure, report, notice, pamphlet, or leaflet containing product information. This form of pharmaceutical information is referred to in the pharmaceutical industry as a "package insert." A package insert may be attached to or included with an article of manufacture. The package insert and any article of manufacture labelling provides information relating to the therapeutically effective amount of COMPOUND 1. The information and labelling provides various forms of information utilized by health-care professionals and patients, describing the therapeutically effective amount of COMPOUND 1, its dosage and various other parameters required by regulatory agencies such as the United States Food and Drug Agencies.

COMPOUND 1 desirably is provided to a subject in an article of manufacture, associated with prescribing information that advises the that the oral dosage form should be taken with or without food, avoiding a high-fat meal. The article of manufacture may also explain that taking the oral dosage with a high-fat meal will increase the bioavailability (e.g., AUC, e.g., $C_{max}$) of COMPOUND 1. COMPOUND 1 preferably is provided to a subject in an article of manufacture, associated with prescribing information that advises the subject that the administration of the dose of COMPOUND 1 with a high-fat meal results in an increase in the extent of absorption of COMPOUND 1 as reflected by an increase in the $AUC_{0-t}$ value of COMPOUND 1 as compared to the administration of the drug under fasted conditions. In some embodiments, COMPOUND 1 is in packaging material with a label affixed to or printed on the packaging material indicating that the therapeutically effective amount of COMPOUND 1 should not be taken within 30 minutes before or after a high-fat meal (e.g., within 45 minutes, 60 minutes, 90 minutes, 120 minutes or 180 minutes before or after a high-fat meal) or a package insert contained within the packaging material indicating that the therapeutically effective amount of COMPOUND 1 should not be taken within 30 minutes before or after a high-fat meal e.g., within 45 minutes, 60 minutes, 90 minutes, 120 minutes or 180 minutes before or after a high-fat meal). The labeling instructions will be consistent with the methods of treatment as described herein. The labeling may be associated with the container by any means that maintain a physical proximity of the two, by way of non-limiting example, they may both be contained in a packaging material such as a box or plastic shrink wrap or may be associated with the instructions being bonded to the container such as with glue that does not obscure the labeling instructions or other bonding or holding means.

EXAMPLES

Example 1. Evaluation of Food Effect on Pharmacokinetics of COMPOUND 1 in Healthy Subjects Design The food effect on COMPOUND 1 PK following administration of a single oral dose of 500 mg of COMPOUND 1 in healthy subjects aged 18-55 years was evaluated in a was a phase 1, open-label, randomized, two-period crossover study.

Safety and tolerability were also evaluated for a single oral dose of 500 mg of COMPOUND 1.

The study was conducted according to the United States Food and Drug Administration (FDA) 2002 Guidance for Industry "Food-Effect Bioavailability and Fed Bioequivalence Studies".

Treatment

Treatments A and B, each comprising a single oral dose of 500 mg of COMPOUND 1, were administered as shown in Table 1.

A (fasted): two 250 mg tablets administered after an overnight fast (approximately 10 hr).

B (fed): two 250 mg tablets administered after a standardized high-fat breakfast, consumed within 30 minutes prior to COMPOUND 1 dosing.

The standardized FDA high-fat content meal contains the equivalent of ~150 protein calories, ~250 carbohydrate calories, and ~500-600 fat calories, and comprises two eggs fried in butter, two strips of bacon, two slices of toast with butter, four ounces of hash brown potatoes (fried with butter), and eight ounces (240 mL) of whole milk.

Of the 30 subjects enrolled, 15 were randomized to sequence AB and 15 were randomized to sequence BA.

TABLE 1

Treatment sequence

| Sequence | Period 1 | Washout period | Period 2 |
|---|---|---|---|
| AB | 500 mg COMPOUND 1 (fasted) | ≥25 days | 500 mg COMPOUND 1 (fed) |
| BA | 500 mg COMPOUND 1 (fed) | ≥25 days | 500 mg COMPOUND 1 (fasted) |

Assessments

Blood samples for the analysis of COMPOUND 1 concentrations were collected predose and 0.5, 1, 2, 3, 4, 6, 9, 12, 24, 48, 72, 120, 168, 240, 336, and 504 hr postdose. Plasma concentrations of COMPOUND 1 were determined using a validated liquid chromatography with tandem mass spectrometry method. PK parameters were calculated using WinNonlin (Pharsight Corporation, Version 6.2.1). Linear mixed model analysis was performed on natural logarithm (ln) transformed maximum observed concentration ($C_{max}$), area under the concentration-time curve from Hour 0 to the last measurable concentration ($AUC_{0-t}$), and area under the concentration-time curve extrapolated to infinity ($AUC_{0-\infty}$). The analyses were performed using the SAS MIXED procedure. The geometric mean ratios (fasted versus fed) and their associated 90% confidence intervals (CIs) for $C_{max}$ and AUCs were calculated to determine whether food had an effect on the PK of COMPOUND 1. Inter-subject variability was determined using the geometric coefficient of variation percent (CV %).

Incidence of adverse events and serious adverse events was assessed.

Results

Following administration in the high-fat and fasted conditions, COMPOUND 1 500 mg was readily absorbed with similar median $T_{max}$ values of 3.00 and 3.-3 hr postdose, respectively (FIG. 1). After reaching $C_{max}$, plasma concentrations slowly declined in a multiphasic manner, with similar mean $T_{1/2}$ values of 53.2 hr in the fed condition and 55.4 hr in the fasted condition. A large increase in $C_{max}$ was observed in the fed compared with the fasted condition, with the extent of exposure (assessed by mean $AUC_{0-t}$ and $AUC_{0-\infty}$) was higher following dosing in the fed versus the fasted condition (Table 2). The inter-subject variability for $AUC_{0-t}$, $AUC_{0-\infty}$, and $C_{max}$ was similar and moderate for both fed and fasted conditions, with CV % values ranging from 31.1% to 31.6% for AUC, and from 21.3% to 24.3% for $C_{max}$.

A single oral dose of 500 mg COMPOUND 1 administered in the fed and fasted conditions appeared to be safe and well tolerated in healthy subjects.

An increase of ~2-fold in mean $C_{max}$ was observed. The lower limit of the 90% CIs for the $C_{max}$ geometric least square (LS)-means ratio (178.7, 218.9) was above 100 when COMPOUND 1 was administered following a high-fat meal compared with the fasted condition (Table 3). The extent of exposure increased by 25.6% and 24.3% as assessed by $AUC_{0-t}$ and $AUC_{0-\infty}$, respectively.

The lower limit of the 90% CIs for the geometric LS-means ratios for $AUC_{0-t}$ (117.2, 134) and $AUC_{0-\infty}$ (116.3, 132.9) was above 100 when COMPOUND 1 was administered following a high-fat meal compared with the fasted condition.

TABLE 2

Plasma PK parameters of COMPOUND 1 following a single oral dose of 500 mg COMPOUND 1 under fasted and fed conditions

| PK parameter | 500 mg COMPOUND 1, fasted n = 29 | 500 mg COMPOUND 1, fed n = 27 |
|---|---|---|
| $AUC_{0-t}$ (hr · ng/mL)[a] | 136,000 (31.6) | 166,000 (31.2) |
| $AUC_{0-\infty}$ (hr · ng/mL)[a] | 143,000 (31.1) | 174,000 (31.2) |
| $C_{max}$ (ng/mL)[a] | 2270 (21.3) | 4490 (24.3) |
| $T_{max}$ (hr)[b] | 3.03 (1.00-24.00) | 3.00 (1.00-6.00) |
| $t_{1/2}$ (hr)[c] | 55.4 (20.5) | 53.2 (18.3) |

[a] Geometric mean (coefficient of variation, %)
[b] Median (min-max)
[c] Arithmetic mean (standard deviation)
$AUC_{0-t}$ = area under the plasma concentration-time curve from Hour 0 up to the last measureable concentration;
$AUC_{0-\infty}$ = area under the plasma concentration-time curve extrapolated to infinity;
$C_{max}$ = maximum observed concentration;
PK = pharmacokinetic;
$t_{1/2}$ = apparent terminal elimination half-life;
$T_{max}$ = time of the maximum concentration An increase of ~2-fold in mean $C_{max}$ was observed. The lower limit of the 90% CIs for the $C_{max}$ geometric least square (LS)-means ratio (178.7, 218.9) was above 100 when COMPOUND 1 was administered following a high-fat meal compared with the fasted condition (Table 3). The extent of exposure increased by 25.6% and 24.3% as assessed by $AUC_{0-t}$ and $AUC_{0-\infty}$, respectively.

The lower limit of the 90% CIs for the geometric LS-means ratios for $AUC_{0-t}$ (117.2, 134) and $AUC_{0-\infty}$ (116.3, 132.9) was above 100 when COMPOUND 1 was administered following a high-fat meal compared with the fasted condition.

TABLE 3

Statistical summary of the effect of food on COMPOUND 1 pharmacokinetics (n = 27)

| Comparison | Parameter | Geometric mean ratio (%) | 90% confidence interval (%) |
|---|---|---|---|
| COMPOUND 1 administered in the fed condition (test) versus in the fasted condition (reference) | $C_{max}$ | 197.8 | 178.7, 218.9 |
| | $AUC_{0-t}$ | 125.6 | 117.2, 134.6 |
| | $AUC_{0-\infty}$ | 124.3 | 116.3, 132.9 |

CONCLUSIONS

Consumption of a high-fat meal prior to dosing had an effect on COMPOUND 1 exposure, with a ~2 fold increase in $C_{max}$ and a ~25% increase in AUC. It is recommended that COMPOUND 1 be administered with or without food; however, high-fat meals at time of dosing should be avoided.

The invention claimed is:

1. A method of treating a malignancy characterized by the presence of a mutant allele of IDH1, comprising administering to a subject a once daily 500 mg oral dose of a mutant isocitrate dehydrogenase 1 (IDH1) inhibitor wherein the mutant IGH1 inhibitor is (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide, having the following formula:

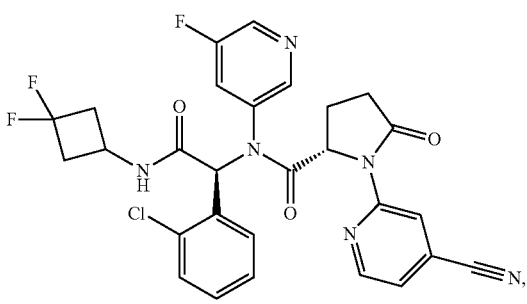 [SMILES: N#Cc1ccnc(N2C(=O)CC[C@H]2C(=O)N(c2cncc(F)c2)[C@H](C(=O)NC2CC(F)(F)C2)c2ccccc2Cl)c1]

or a pharmaceutically acceptable salt thereof (COMPOUND 1) wherein the compound is administered to a subject that has not ingested a high-fat meal.

2. The method of claim 1, wherein the oral dose is administered substantially contemporaneously with food, wherein the food is not a high-fat meal.

3. The method of claim 1 wherein the oral dose is administered without food.

4. The method of claim 1 wherein the oral dose is administered to a subject that has not ingested a high-fat meal for at least 60 minutes before administration of the oral dose.

5. The method of claim 1 wherein the oral dose is administered to the subject at least 60 minutes before ingestion of any high-fat meal.

6. The method of claim 1 wherein the $C_{max}$ of COMPOUND 1 is between 1500 ng/mL and 3100 ng/mL.

7. The method of claim 1 wherein the $AUC_{0-t}$ of COMPOUND 1 is between 110000 hr·ng/mL and 165000 hr·ng/mL.

8. The method of claim 1 wherein the oral dose comprises COMPOUND 1 as part of a solid dispersion.

9. The method of claim 1 wherein the malignancy is a hematologic malignancy.

10. The method of claim 9 wherein the hematologic malignancy is acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma.

11. The method of claim 10, wherein the malignancy is acute myelogenous leukemia (AML).

12. The method of claim 11 wherein the acute myelogenous leukemia (AML) is relapsed or refractory.

13. The method of claim 1 wherein the malignancy is a solid tumor.

14. The method of claim 13 wherein the solid tumor is selected from glioma, intrahepatic cholangiocarcinomas (IHCC), chondrosarcoma, prostate cancer, colon cancer, melanoma, and non-small cell lung cancer (NSCLC).

15. The method of claim 14 wherein the solid tumor is intrahepatic cholangiocarcinoma.

16. The method of claim 13 wherein the solid tumor is advanced.

17. The method of claim 13 wherein the solid tumor is relapsed or refractory.

18. The method of claim 1 wherein the IDH1 mutation is an IDH1 R132X mutation.

19. The method of claim 18, wherein the IDH1 mutation is an IDH1 R132H, R132C, R132L, R132V, R132S or R132GF mutation.

* * * * *